(12) United States Patent
Hong et al.

(10) Patent No.: US 9,419,229 B2
(45) Date of Patent: Aug. 16, 2016

(54) COMPOUND, ORGANIC OPTOELECTRIC DEVICE INCLUDING THE SAME AND DISPLAY DEVICE INCLUDING THE OPTOELECTRIC DEVICE

(71) Applicants: Jin-Seok Hong, Uiwang-si (KR);
 Dong-Min Kang, Uiwang-si (KR);
 Eun-Sun Yu, Uiwang-si (KR);
 Soo-Young Jeong, Uiwang-si (KR);
 Ji-Hun Shin, Uiwang-si (KR);
 Dong-Kyu Ryu, Uiwang-si (KR);
 Han-ill Lee, Uiwang-si (KR); Yu-Na Jang, Uiwang-si (KR)

(72) Inventors: Jin-Seok Hong, Uiwang-si (KR);
 Dong-Min Kang, Uiwang-si (KR);
 Eun-Sun Yu, Uiwang-si (KR);
 Soo-Young Jeong, Uiwang-si (KR);
 Ji-Hun Shin, Uiwang-si (KR);
 Dong-Kyu Ryu, Uiwang-si (KR);
 Han-ill Lee, Uiwang-si (KR); Yu-Na Jang, Uiwang-si (KR)

(73) Assignee: CHEIL INDUSTRIES, INC., Gumi-si, Kyeongsangbuk-do (KR)

( * ) Notice: Subject to any disclaimer, the term of this patent is extended or adjusted under 35 U.S.C. 154(b) by 451 days.

(21) Appl. No.: 14/084,687

(22) Filed: Nov. 20, 2013

(65) Prior Publication Data

US 2014/0374706 A1 Dec. 25, 2014

(30) Foreign Application Priority Data

Jun. 20, 2013 (KR) .................. 10-2013-0071123

(51) Int. Cl.
 *H01L 51/54* (2006.01)
 (Continued)

(52) U.S. Cl.
 CPC .......... *H01L 51/0067* (2013.01); *C07D 235/02* (2013.01); *C07D 239/04* (2013.01);
 (Continued)

(58) Field of Classification Search
 CPC .................. H01L 2251/308; H01L 51/0067;
 H01L 51/0072; H01L 51/0081; H01L 51/0085; C09K 11/06; C07D 487/04; C07D 235/02; C07D 239/04; C07D 401/14
 See application file for complete search history.

(56) References Cited

U.S. PATENT DOCUMENTS 8,329,898 B2 12/2012 Salbeck et al.
2009/0209571 A1* 8/2009 Cote .................... C07D 471/04
 514/287

(Continued)

FOREIGN PATENT DOCUMENTS

KR 10-2008-0084762 A 9/2008

OTHER PUBLICATIONS

Agarwal, A. et al., Indian Journal of Chemistry, vol. 31B, Jan. 1992, pp. 44-49.*

(Continued)

*Primary Examiner* — Dawn Garrett
(74) *Attorney, Agent, or Firm* — Lee & Morse, P.C.

(57) ABSTRACT

Disclosed are a compound for an organic optoelectric device, an organic optoelectric device including the same and a display device including the organic optoelectric device, wherein the compound for an organic optoelectric device is represented by the following Chemical Formula 1,

[Chemical Formula 1]

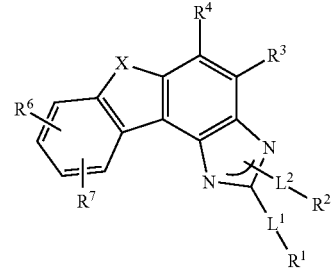

In the above Chemical Formula 1, $R^1$ to $R^7$, X, $L^1$ and $L^2$ are the same as described in the detailed description.

14 Claims, 1 Drawing Sheet

(51) Int. Cl.
  *H01L 51/00* (2006.01)
  *C07D 487/04* (2006.01)
  *C07D 235/02* (2006.01)
  *C07D 239/04* (2006.01)
  *C07D 401/14* (2006.01)
  *C09K 11/06* (2006.01)

(52) U.S. Cl.
  CPC ............ *C07D401/14* (2013.01); *C07D 487/04* (2013.01); *C09K 11/06* (2013.01); *H01L 51/0072* (2013.01); *H01L 51/0081* (2013.01); *H01L 51/0085* (2013.01); *H01L 2251/308* (2013.01)

(56) References Cited

U.S. PATENT DOCUMENTS

| | | |
|---|---|---|
| 2011/0240977 A1 | 10/2011 | Jung et al. |
| 2011/0240978 A1 | 10/2011 | Lim et al. |
| 2011/0266528 A1 | 11/2011 | Langer et al. |
| 2015/0171344 A1* | 6/2015 | Bae .................. C07D 487/04 257/40 |

OTHER PUBLICATIONS

Lancelot, et al., Imidazo [4,5-c]carbazoles: Synthese et Etude des Spectres de Resonance Magnetique Nucleaire, Chem. Pharm. Bull, vol. 32, pp. 452-456, 1984.

* cited by examiner

COMPOUND, ORGANIC OPTOELECTRIC DEVICE INCLUDING THE SAME AND DISPLAY DEVICE INCLUDING THE OPTOELECTRIC DEVICE

CROSS-REFERENCE TO RELATED APPLICATION

Korean Patent Application No. 10-2013-0071123, filed on Jun. 20, 2013, in the Korean Intellectual Property Office, and entitled: "Compound, Organic Optoelectric Device Including The Same and Display Device Including The Optoelectric Device," is incorporated by reference herein in its entirety.

BACKGROUND

1. Field

Embodiments relate to a compound for an organic optoelectric device, an organic optoelectric device including the same, and a display device including the organic optoelectric device.

2. Description of the Related Art

An organic optoelectric device may be a device that converts electrical energy into photo energy, or vice versa.

An organic optoelectric device may be classified as follows in accordance with its driving principles. One is an electronic device where excitons generated by photo energy are separated into electrons and holes, the electrons and holes are transferred to different electrodes, respectively, and electrical energy is generated. The other is a light emitting device to generate photo energy from electrical energy by supplying a voltage or a current to electrodes.

Examples of the organic optoelectric device include an organic photoelectric device, an organic light emitting diode, an organic solar cell, and an organic photo-conductor drum, and the like.

SUMMARY

Embodiments are directed to a compound, represented by the following Chemical Formula 1, for an organic optoelectric device,

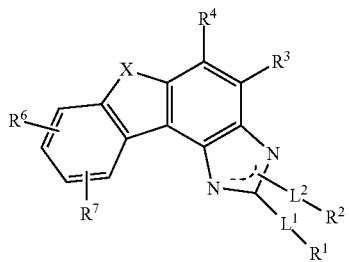

[Chemical Formula 1]

In the above Chemical Formula 1, $R^1$ and $R^2$ may each independently be a substituted or unsubstituted C6 to C30 aryl group, a substituted or unsubstituted C2 to C30 heteroaryl group, or a combination thereof, X may be O, S, $SO_2$ (O=S=O), PO(P=O), $N-L^3-R^5$, CR'R", or SiR'R", $L^1$ to $L^3$ may each independently be a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, a substituted or unsubstituted C2 to C30 heteroarylene group, a substituted or unsubstituted C6 to C30 aryleneamine group, a substituted or unsubstituted C2 to C30 heteroaryleneamine group, a substituted or unsubstituted C1 to C30 alkoxylene group, a substituted or unsubstituted C6 to C30 aryloxylene group, a substituted or unsubstituted C2 to C30 alkenylene group, a substituted or unsubstituted C2 to C30 alkynylene group, or a combination thereof, $R^3$ to $R^7$, R', and R" may each independently be hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthio group, a substituted or unsubstituted C1 to C20 heterocyclothio group, a substituted or unsubstituted C1 to C20 ureide group, a substituted or unsubstituted C3 to C40 silyl group, or a combination thereof, $R^3$ and $R^4$ may each independently be present or may be fused to each other to form a ring, and the dotted line represents a single bond or a double bond.

Embodiments are also directed to an organic optoelectric device, including an anode and a cathode facing each other, and at least one organic layer interposed between the anode and the cathode. The organic layer may include a compound for an organic optoelectric device according to an embodiment.

The organic layer may include an emission layer, and the emission layer may include the compound for an organic optoelectric device.

Embodiments are also directed to a display device including an organic optoelectric device according to an embodiment.

BRIEF DESCRIPTION OF THE DRAWINGS

Features will become apparent to those of skill in the art by describing in detail example embodiments with reference to the attached drawings in which.

DETAILED DESCRIPTION

Figure 1:
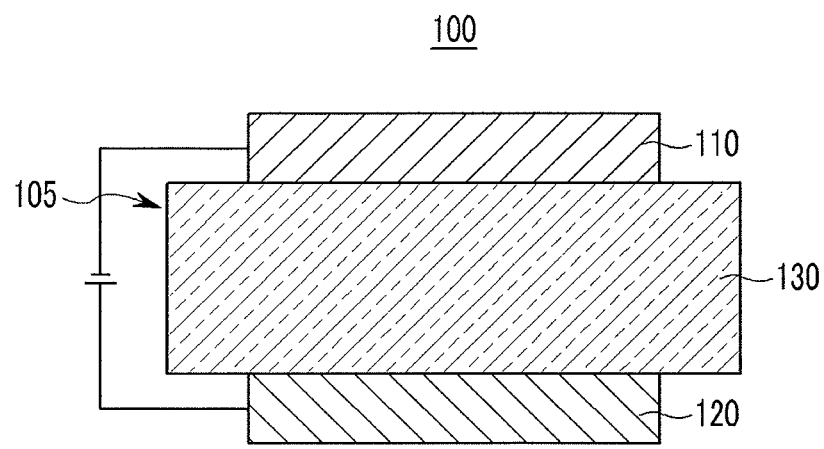
FIGS. 1 and 2 illustrate cross-sectional views of various organic light emitting diodes according to example embodiments.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

As used herein, when a definition is not otherwise provided, the term "substituted" refers to one substituted with a deuterium, a halogen, a hydroxy group, an amino group, a substituted or unsubstituted C1 to C30 amine group, a nitro group, a substituted or unsubstituted C1 to C40 silyl group, a C1 to C30 alkyl group, a C1 to C10 alkylsilyl group, a C3 to C30 cycloalkyl group, a C6 to C30 aryl group, a C1 to C20 alkoxy group, a fluoro group, a C1 to C10 trifluoroalkyl group such as a trifluoromethyl group and the like, or a cyano group, instead of at least one hydrogen of a substituent or a compound.

In addition, two adjacent substituents of the substituted halogen, hydroxy group, amino group, substituted or unsubstituted C1 to C20 amine group, nitro group, substituted or unsubstituted C3 to C40 silyl group, C1 to C30 alkyl group, C1 to C10 alkylsilyl group, C3 to C30 cycloalkyl group, C6 to C30 aryl group, C1 to C20 alkoxy group, fluoro group, C1 to C10 trifluoroalkyl group such as a trifluoromethyl group and the like, or cyano group may be fused with each other to form a ring. Specifically, the substituted C6 to C30 aryl group may be fused with another adjacent substituted C6 to C30 aryl group to form a substituted or unsubstituted fluorene ring.

In the specification, a moiety represented by a dotted line in a chemical structure indicates a single bond or a double bond. Specifically, in the chemical structure represented by Chemical Formula 1, the dotted line represented through —N—C—N— of a benzimidazole-like moiety indicates that when a moiety of one —N—C— moiety is a double bond, a moiety of the other —N—C— moiety is a single bond.

In the present specification, when specific definition is not otherwise provided, the term "hetero" refers to one including 1 to 3 hetero atoms selected from N, O, S, and P, and remaining carbons in one functional group.

In the present specification, when a definition is not otherwise provided, the term "alkyl group" may refer to an aliphatic hydrocarbon group. The alkyl group may refer to "a saturated alkyl group" without any double bond or triple bond.

The alkyl group may be a C1 to C20 alkyl group. More specifically, the alkyl group may be a C1 to C10 alkyl group or a C1 to C6 alkyl group. For example, a C1 to C4 alkyl group includes 1 to 4 carbon atoms in an alkyl chain, and may be selected from methyl, ethyl, propyl, iso-propyl, n-butyl, iso-butyl, sec-butyl, and t-butyl.

Specific examples of the alkyl group may be a methyl group, an ethyl group, a propyl group, an isopropyl group, a butyl group, an isobutyl group, a t-butyl group, a pentyl group, a hexyl group, a cyclopropyl group, a cyclobutyl group, a cyclopentyl group, a cyclohexyl group, and the like.

In the present specification, the term "aryl group" refers to a substituent including all element of the cycle having p-orbitals which form conjugation, and may be monocyclic or fused ring polycyclic (i.e., rings sharing adjacent pairs of carbon atoms) functional group.

As used herein, the term "heteroaryl group" may refer to aryl group including 1 to 3 hetero atoms selected from N, O, S, and P, and remaining carbons in an aryl group. The heteroaryl group may be a fused ring where each ring may include the 1 to 3 heteroatoms.

More specifically, the substituted or unsubstituted C6 to C30 aryl group and/or the substituted or unsubstituted C2 to C30 heteroaryl group may be a substituted or unsubstituted phenyl group, a substituted or unsubstituted naphthyl group, a substituted or unsubstituted anthracenyl group, a substituted or unsubstituted phenanthryl group, a substituted or unsubstituted naphthacenyl group, a substituted or unsubstituted pyrenyl group, a substituted or unsubstituted biphenylyl group, a substituted or unsubstituted p-terphenyl group, a substituted or unsubstituted m-terphenyl group, a substituted or unsubstituted chrysenyl group, a substituted or unsubstituted triphenylenyl group, a substituted or unsubstituted perylenyl group, a substituted or unsubstituted indenyl group, a substituted or unsubstituted furanyl group, a substituted or unsubstituted thiophenyl group, a substituted or unsubstituted pyrrolyl group, a substituted or unsubstituted pyrazolyl group, a substituted or unsubstituted imidazolyl group, a substituted or unsubstituted triazolyl group, a substituted or unsubstituted oxazolyl group, a substituted or unsubstituted thiazolyl group, a substituted or unsubstituted oxadiazolyl group, a substituted or unsubstituted thiadiazolyl group, a substituted or unsubstituted pyridyl group, a substituted or unsubstituted pyrimidinyl group, a substituted or unsubstituted pyrazinyl group, a substituted or unsubstituted triazinyl group, a substituted or unsubstituted benzofuranyl group, a substituted or unsubstituted benzothiophenyl group, a substituted or unsubstituted benzimidazolyl group, a substituted or unsubstituted indolyl group, a substituted or unsubstituted quinolinyl group, a substituted or unsubstituted isoquinolinyl group, a substituted or unsubstituted quinazolinyl group, a substituted or unsubstituted quinoxalinyl group, a substituted or unsubstituted naphthyridinyl group, a substituted or unsubstituted benzoxazinyl group, a substituted or unsubstituted benzthiazinyl group, a substituted or unsubstituted acridinyl group, a substituted or unsubstituted phenazinyl group, a substituted or unsubstituted phenothiazinyl group, a substituted or unsubstituted phenoxazinyl group, a substituted or unsubstituted fluorenyl group, a substituted or unsubstituted dibenzofuranyl group, a substituted or unsubstituted dibenzothiophenyl group, a substituted or unsubstituted carbazole group, or a combination thereof, but are limited thereto.

In the specification, hole characteristics refer to characteristics that hole formed in the anode is easily injected into the emission layer and transported in the emission layer due to conductive characteristics according to HOMO level. More specifically, it is similar to electron-repelling characteristics.

In addition, electron characteristics refer to characteristics that electron formed in the cathode is easily injected into the emission layer and transported in the emission layer due to conductive characteristics according to LUMO level. More specifically, it is similar to electron-withdrawing characteristics.

According to an example embodiment, a compound represented by the following Chemical Formula 1 for an organic optoelectric device is provided.

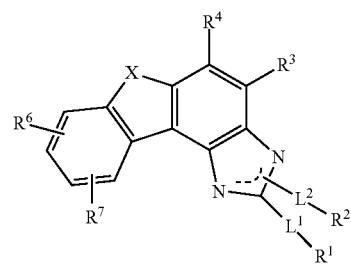

[Chemical Formula 1]

In the present example embodiment, in the above Chemical Formula 1, $R^1$ or $R^2$ are each independently a substituted or unsubstituted C6 to C30 aryl group, a substituted or unsubstituted C2 to C30 heteroaryl group, or a combination thereof, X is O, S, $SO_2$ (O=S=O), PO(P=O), N-$L^3$-$R^5$, CR'R", or SiR'R", $L^1$ to $L^3$ are each independently a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, or a substituted or unsubstituted C2 to C30 heteroarylene group, a substituted or unsubstituted C6 to C30 aryleneamine group, a substituted or unsubstituted C2 to C30 heteroaryleneamine group, a substituted or unsubstituted C1 to C30 alkoxylene group, a substituted or unsubstituted C6 to C30 aryloxylene group, a substituted or unsubstituted C2 to C30 alkenylene group, a substituted or unsubstituted C2 to C30 alkynylene group, or a combination thereof, $R^3$ to $R^7$, R', and R" are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 aryloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthio group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof, $R^3$ and $R^4$ are each independently present or are fused to each other to form a ring, and the dotted line represents a single bond or a double bond.

The compound for an organic optoelectric device according to an example embodiment has hole characteristics and electron characteristics simultaneously, and may transfer holes and electrons effectively.

In an example embodiment, the above Chemical Formula 1 may be represented by the following Chemical Formula 2 or Chemical Formula 3.

[Chemical Formula 2]

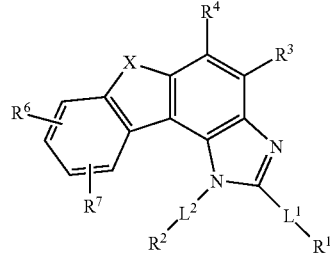

-continued

[Chemical Formula 3]

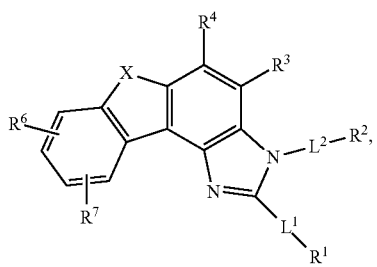

In the present example embodiment, in the above Chemical Formula 2 or 3, $R^1$ or $R^2$ are each independently a substituted or unsubstituted C6 to C30 aryl group, a substituted or unsubstituted C2 to C30 heteroaryl group, or a combination thereof, X is O, S, $SO_2$ (O=S=O), PO(P=O), or N-$L^3$-$R^5$, $L^1$ to $L^3$ are each independently a single bond, a substituted or unsubstituted C1 to C30 alkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, $R^3$ to $R^7$ are each independently hydrogen, deuterium, a halogen, a cyano group, a hydroxyl group, an amino group, a substituted or unsubstituted C1 to C20 amine group, a substituted or unsubstituted C1 to C20 alkyl group, a substituted or unsubstituted C6 to C30 aryl group, a substituted or unsubstituted C2 to C30 heteroaryl group, a substituted or unsubstituted C3 to C40 silyloxy group, a substituted or unsubstituted C3 to C40 silyl group, or a combination thereof, $R^3$ and $R^4$ are each independently present or are fused to each other to form a ring.

The compound represented by the above Chemical Formula 1 may have various energy bandgaps by introducing various substituents.

The compound may have an appropriate energy level depending on the substituents and, thus, may fortify hole transport capability or electron transport capability of an organic optoelectric device, and bring about excellent effects on efficiency and driving voltage, and may have excellent electrochemical and thermal stability and, thus, may improve life-span characteristics during the operation of the organic optoelectric device.

In the above Chemical Formula 1, $R^3$ and $R^4$ may be fused to each other to form a ring, and the ring may be a substituted or unsubstituted indolyl group, a substituted or unsubstituted phenyl group, a substituted or unsubstituted naphthyl group, a substituted or unsubstituted anthracenyl group, a substituted or unsubstituted phenanthryl group, or a substituted or unsubstituted quinolinyl group.

In the compound for an organic optoelectric device according to an example embodiment having a fused ring of $R^3$ and $R^4$, hole and electron transport capability may be fortified.

In an example embodiment, the above Chemical Formula 1 including $R^3$ and $R^4$ fused to each other may be represented by the following Chemical Formula 4 or 5.

[Chemical Formula 4]

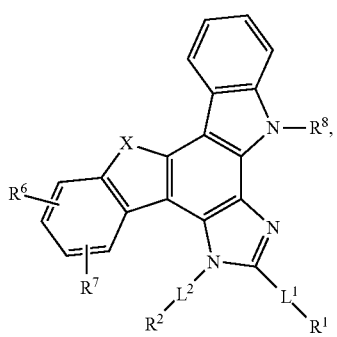

[Chemical Formula 5]

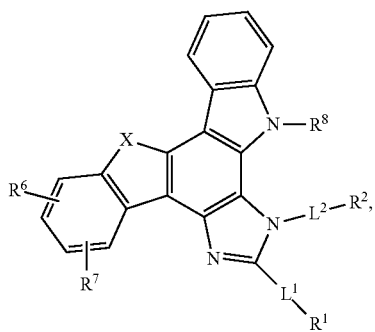

In the present example embodiment, in the above Chemical Formula 4 or 5, $R^1$, $R^2$, and $R^8$ are each independently a substituted or unsubstituted C6 to C30 aryl group, a substituted or unsubstituted C2 to C30 heteroaryl group, or a combination thereof, X is O, S, $SO_2$ (O=S=O), PO(P=O), or $N-L^3-R^5$, $L^1$ to $L^3$ are each independently a single bond, a substituted or unsubstituted C1 to C30 alkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, and $R^5$ to $R^7$ are each independently hydrogen, deuterium, a halogen, a cyano group, a hydroxyl group, an amino group, a substituted or unsubstituted C1 to C20 amine group, a substituted or unsubstituted C1 to C20 alkyl group, a substituted or unsubstituted C6 to C30 aryl group, a substituted or unsubstituted C2 to C30 heteroaryl group, a substituted or unsubstituted C3 to C40 silyloxy group, a substituted or unsubstituted C3 to C40 silyl group, or a combination thereof.

In the compound according to an example embodiment represented by Chemical Formula 4 or 5, hole characteristics may be fortified and efficiency of a device using the same may increase.

The $R^8$ may be a substituted or unsubstituted phenyl group, a substituted or unsubstituted biphenyl group, a substituted or unsubstituted pyridyl group, a substituted or unsubstituted pyrimidyl group, a substituted or unsubstituted triazinyl group, or a substituted or unsubstituted triphenylene group.

For example, the $R^8$ may be one of the substituted or unsubstituted functional groups listed in the following Group I.

[Group I]

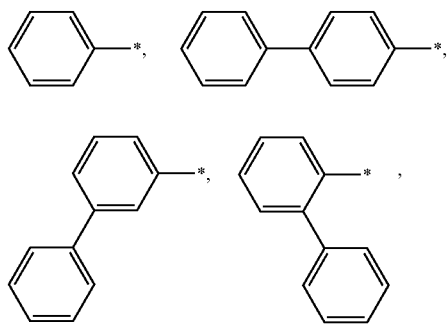

The $R^8$ may help provide electron transfer characteristics, and the compound for an organic optoelectric device having the same may have decreased hole characteristics and may have characteristics appropriate for an emission layer.

The above Chemical Formula 1 may be represented by one of the following Chemical Formulae 6 to 8.

[Chemical Formula 6]

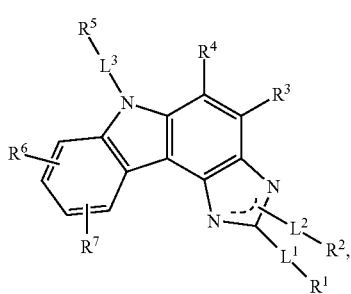

[Chemical Formula 7]

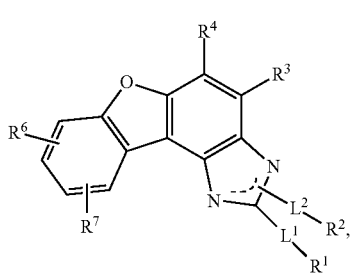

[Chemical Formula 8]

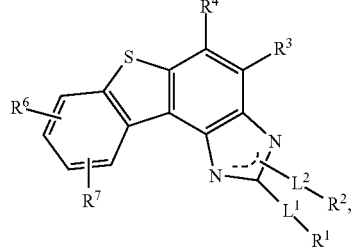

In the present example embodiment, in the above Chemical Formulae 6 to 8, $R^1$ or $R^2$ are each independently a substituted or unsubstituted C6 to C30 aryl group, a substituted or unsubstituted C2 to C30 heteroaryl group, or a combination thereof, $L^1$ to $L^3$ are each independently a single bond, a substituted or unsubstituted C1 to C30 alkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, $R^3$ to $R^7$ are each independently hydrogen, deuterium, a halogen, a cyano group, a hydroxyl group, an amino group, a substituted or unsubstituted C1 to C20 amine group, a substituted or unsubstituted C1 to C20 alkyl group, a substituted or unsubstituted C6 to C30 aryl group, a substituted or unsubstituted C2 to C30 heteroaryl group, a substituted or unsubstituted C3 to C40 silyloxy group, a substituted or unsubstituted C3 to C40 sayl group, or a combination thereof, $R^3$ and $R^4$ are each independently present or are fused to each other to form a ring, and the dotted line represents a single bond or a double bond.

According to the present example embodiment, the selected X may provide a compound having appropriate anode characteristics, and may transfer holes and electrons effectively.

In an example embodiment, the $R^3$ to $R^5$ are each independently hydrogen, deuterium, or one of the substituted or unsubstituted functional groups listed in Group II, and at least one of $R^3$ to $R^5$ may be a substituted or unsubstituted functional group listed in the following Group II,

[Group II]

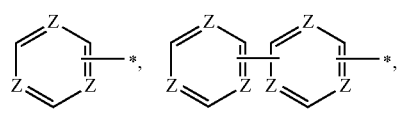

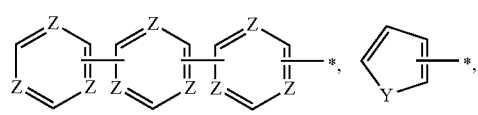

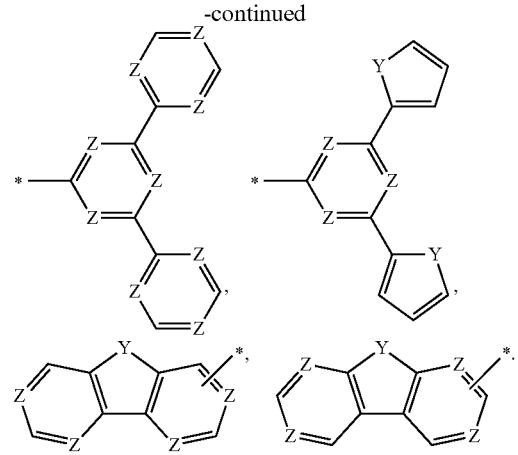

According to the present example embodiment, in the Group II, each Z is independently N or CR, each Y is independently O, S, SO, $SO_2$, NR', CR'R" or SiR'R", wherein R, R' and R" are each independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C2 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthio group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and

* is a linking point, and may be positioned at one of an element constituting the functional group.

According to the present example embodiment, the $R^3$ to $R^5$ as above may transport electrons effectively.

In an example embodiment, the $R^3$ to $R^5$ are each independently hydrogen, deuterium, or one of substituted or unsubstituted functional groups represented by the following Group III, and at least one of $R^3$ to $R^5$ is a substituted or unsubstituted functional group represented by the following Group III,

[Group III]
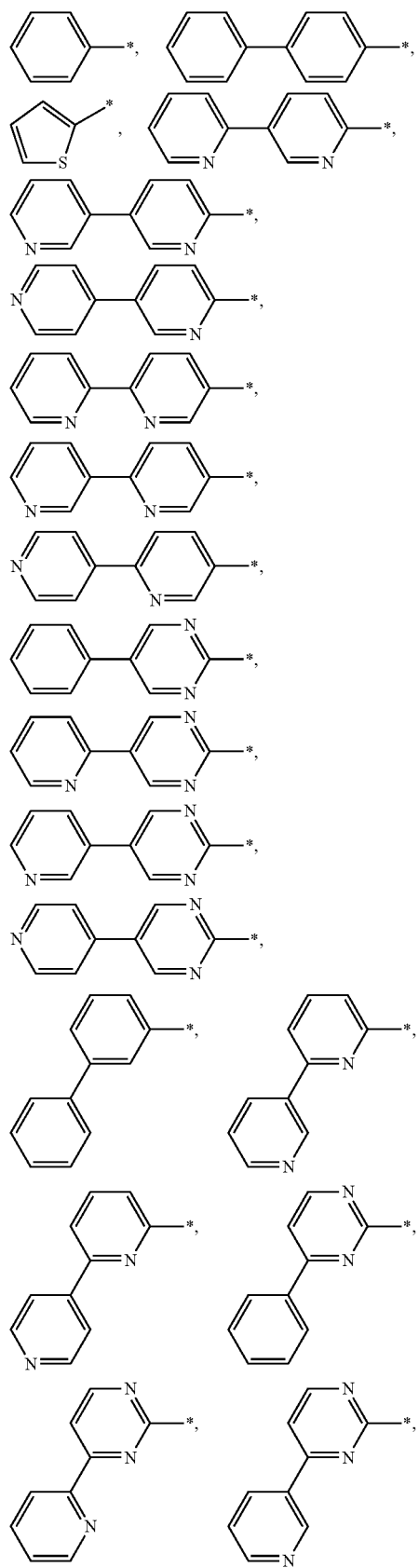
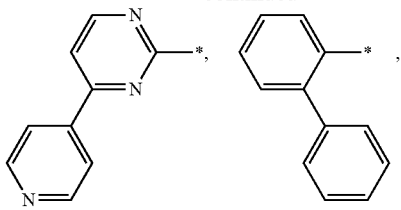
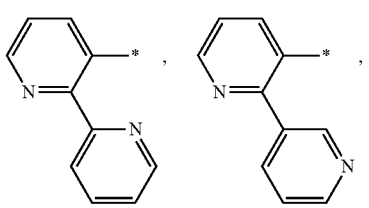
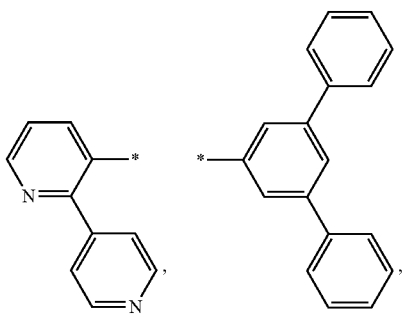
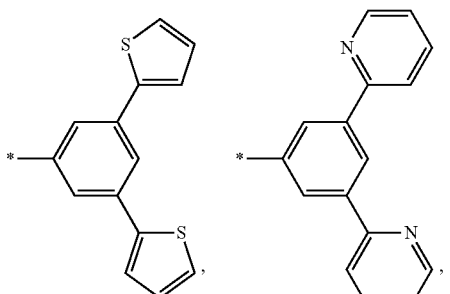
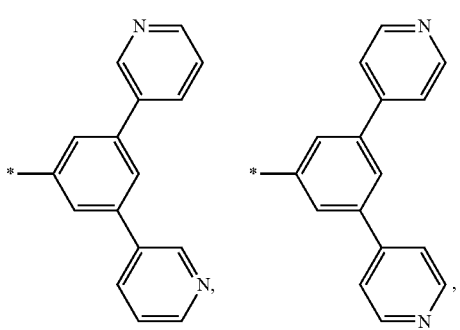
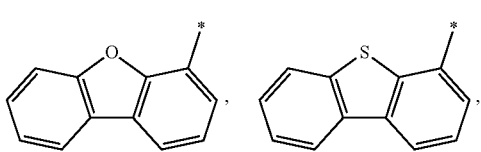

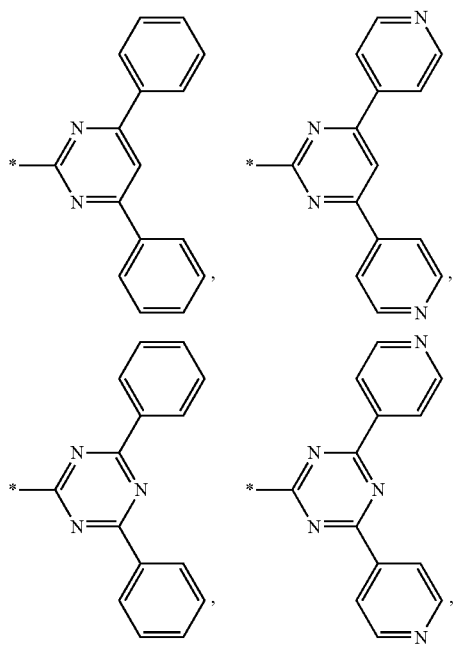
In the Group III, * indicates a linking point.
According to the present example embodiment, the $R^3$ to $R^5$ as above may transport electrons effectively.
Examples of compounds according to example embodiments may include, e.g.,
[3-1]
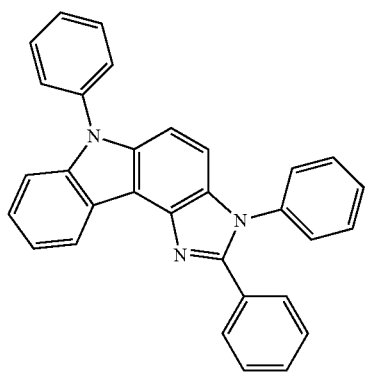
[3-2]
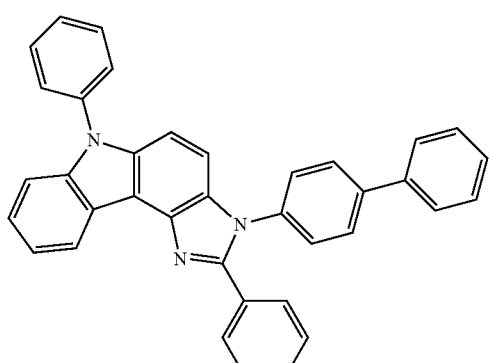
[3-3]
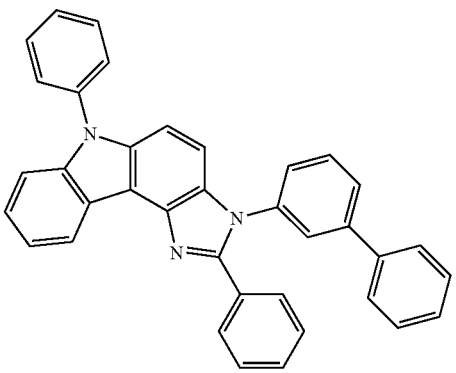
[3-4]
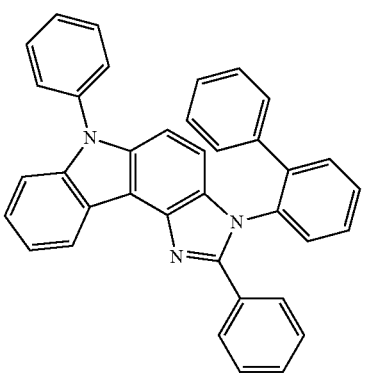
[3-5]
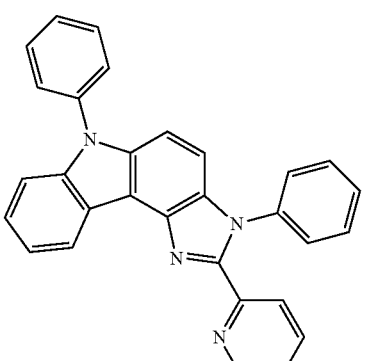
[3-6]
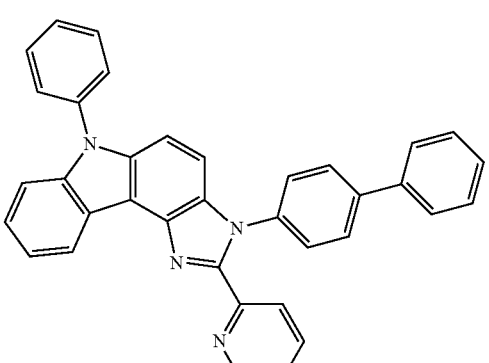

[3-7]
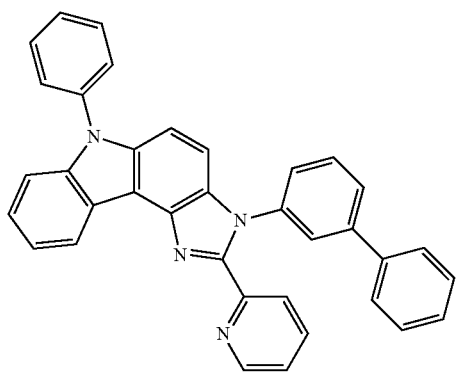
[3-11]
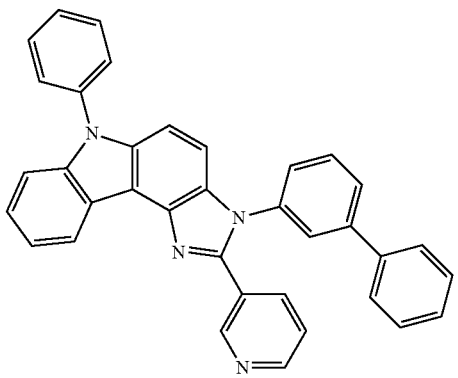
[3-8]
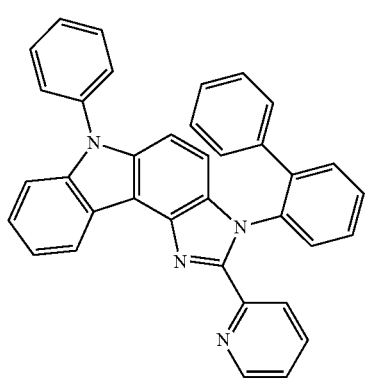
[3-12]
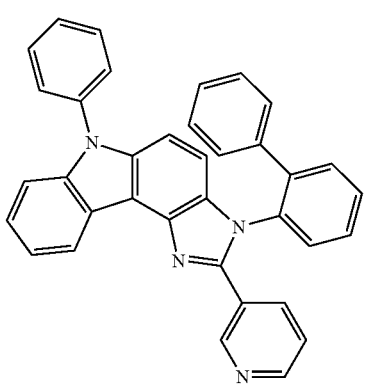
[3-9]
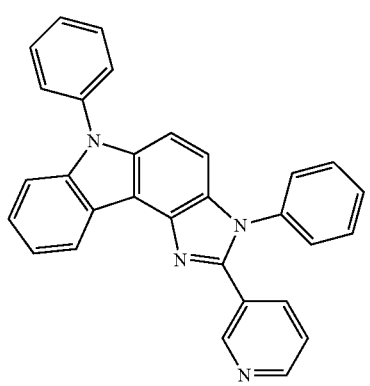
[3-13]
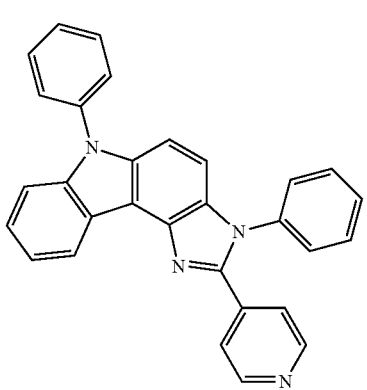
[3-10]
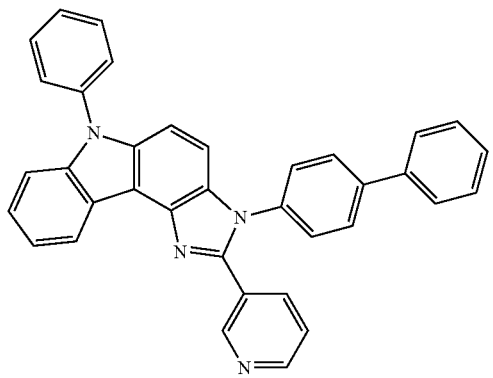
[3-14]
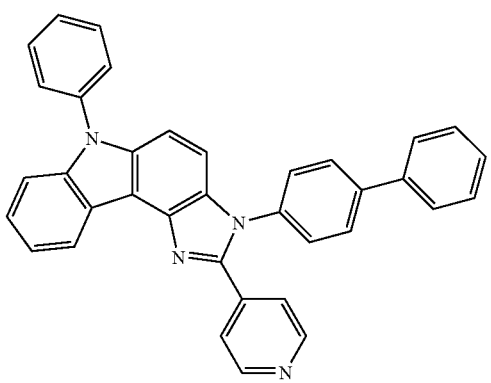

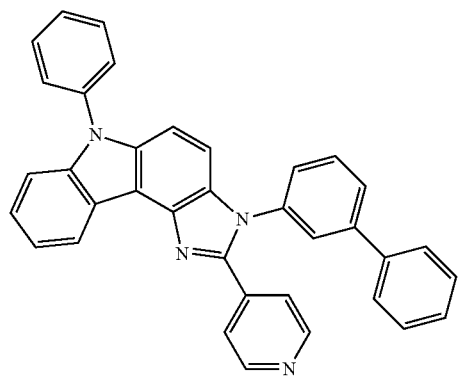
[3-15]
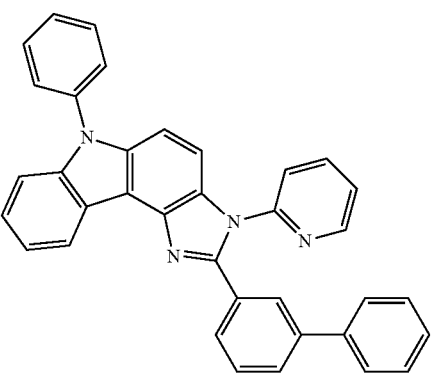
[3-19]
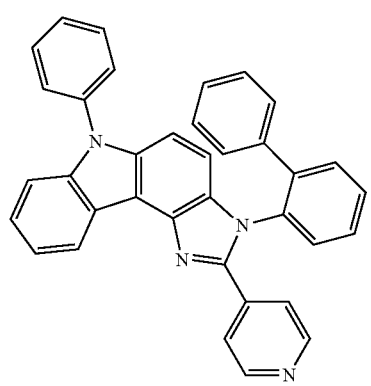
[3-16]
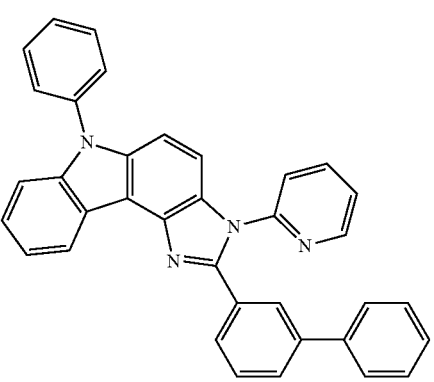
[3-20]
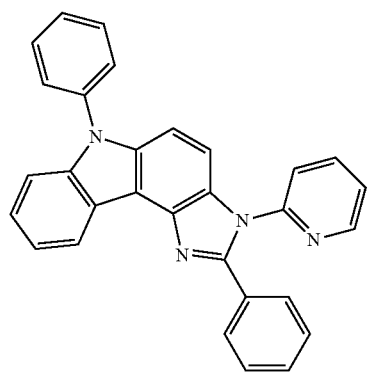
[3-17]
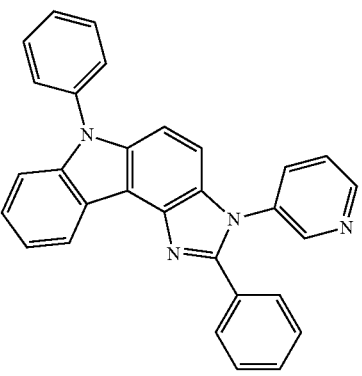
[3-21]
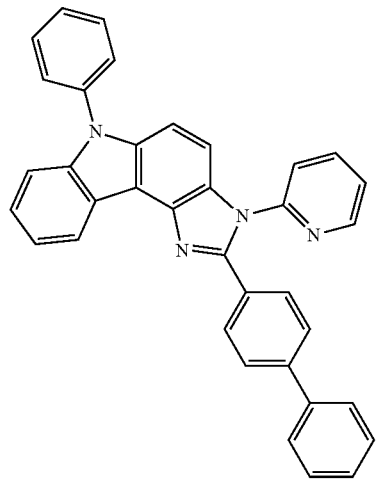
[3-18]
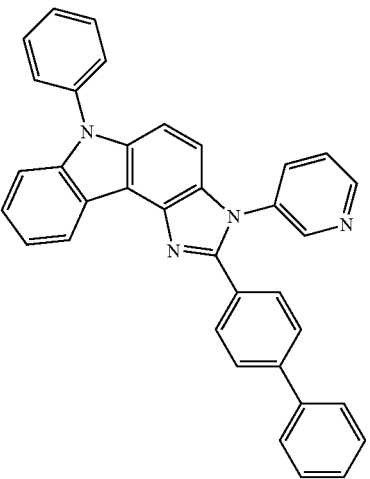
[3-22]

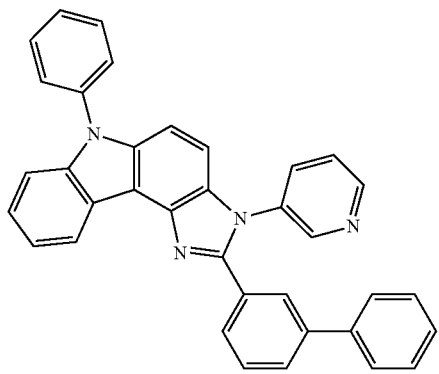
[3-23]
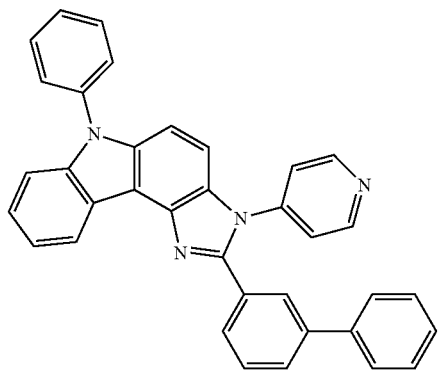
[3-27]
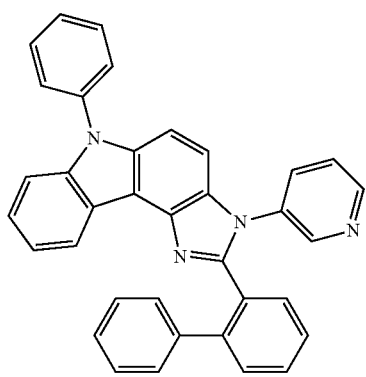
[3-24]
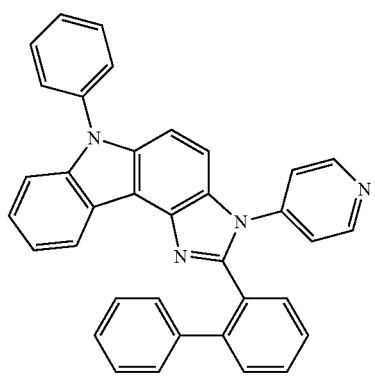
[3-28]
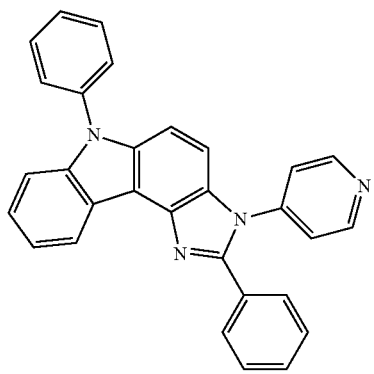
[3-25]
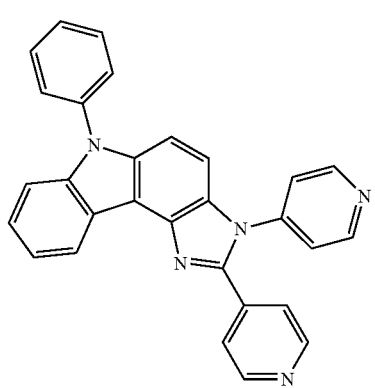
[3-29]
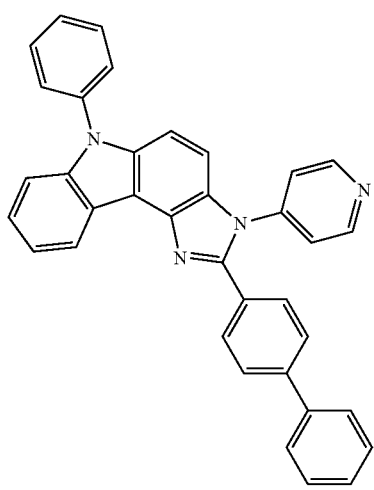
[3-26]
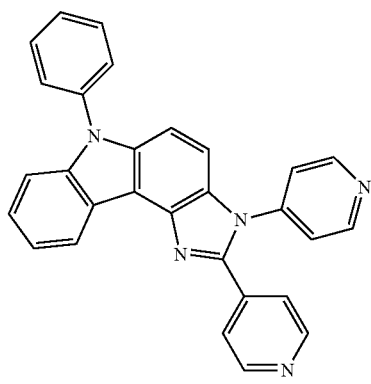
[3-30]

[3-31]
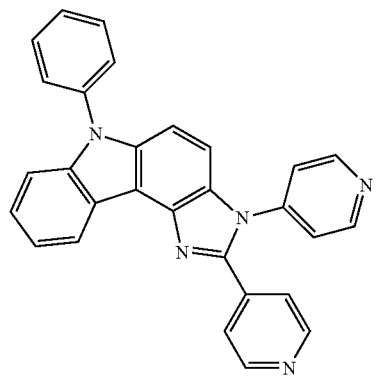
[3-32]
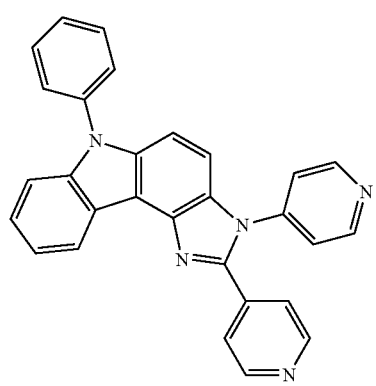
[3-33]
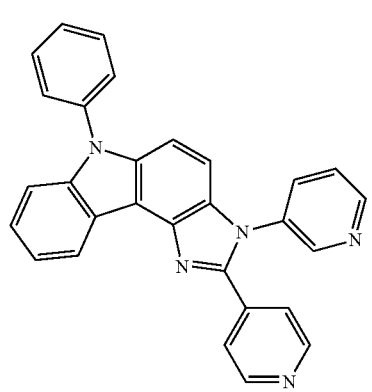
[3-34]
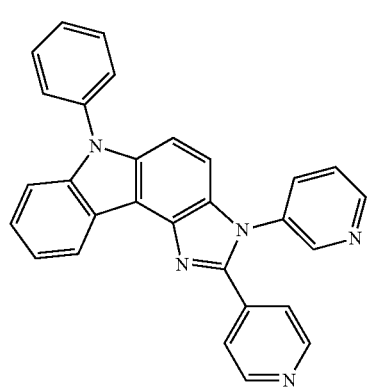
[3-35]
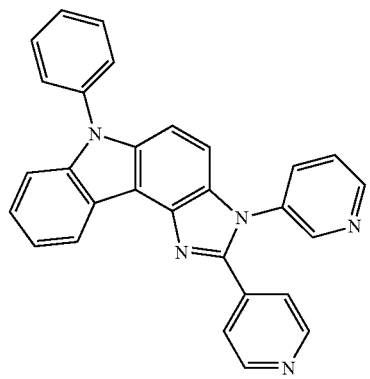
[3-36]
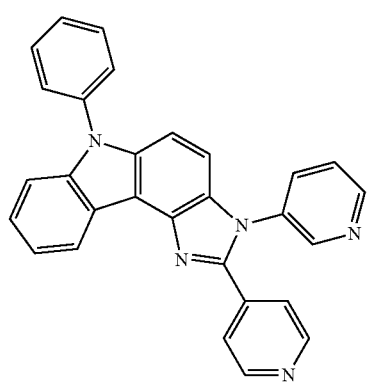
[3-37]
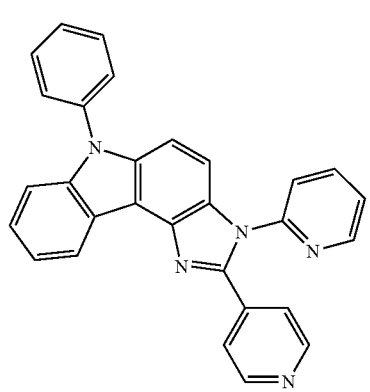
[3-38]
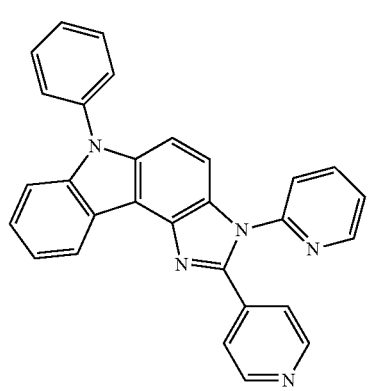

[3-39]
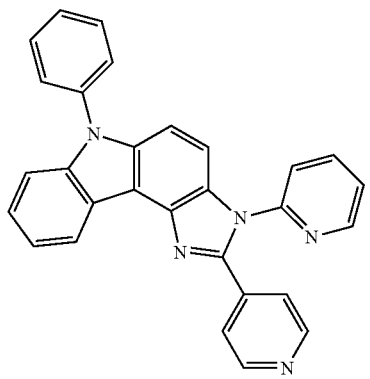
[3-43]
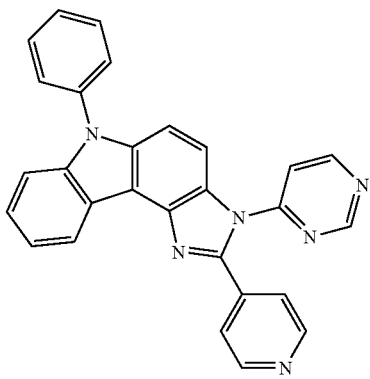
[3-40]
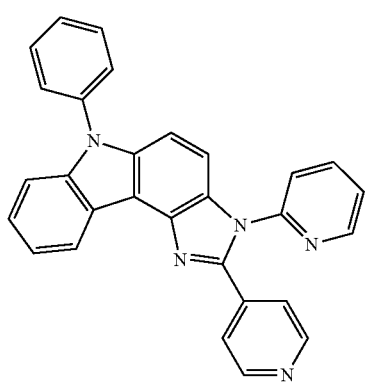
[3-44]
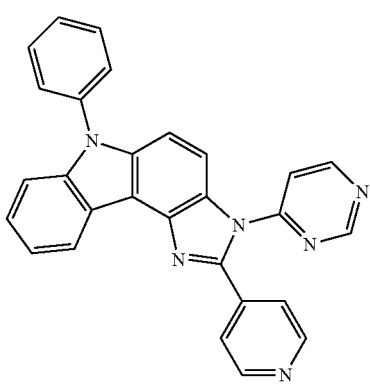
[3-41]
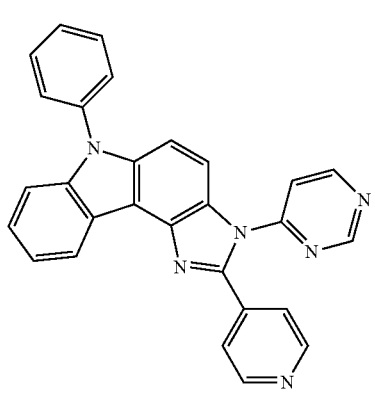
[3-45]
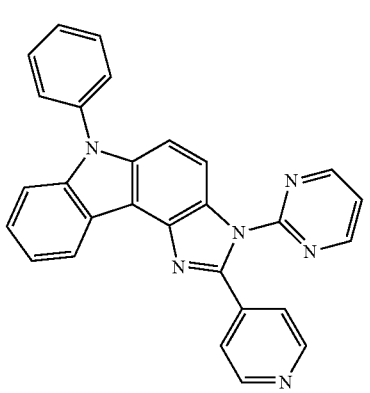
[3-42]
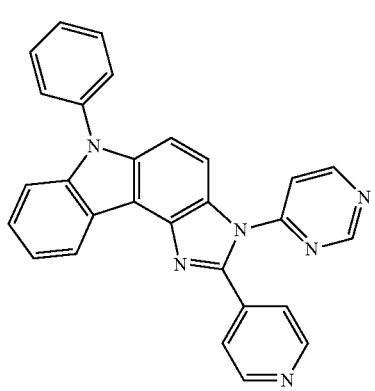
[3-46]
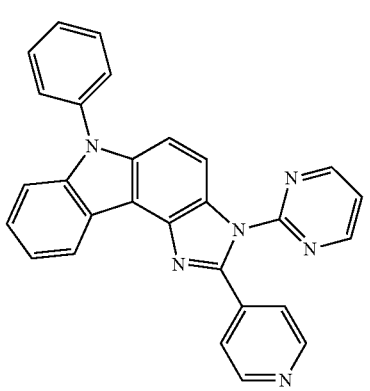

[3-47]
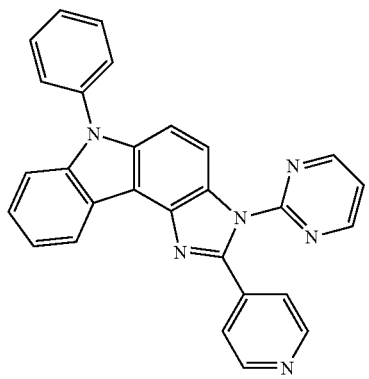
[3-48]
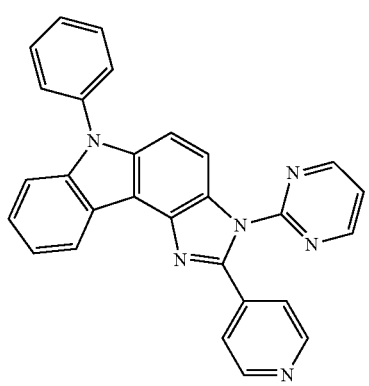
[3-49]
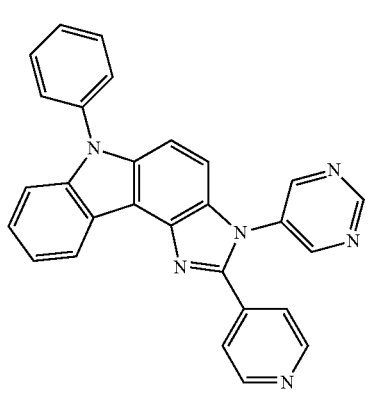
[3-50]
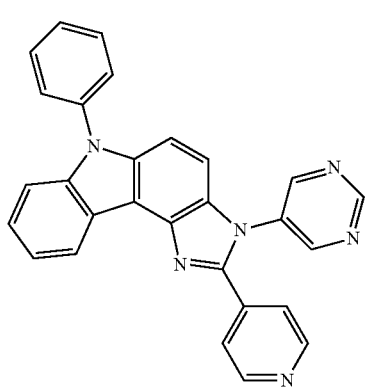
[3-51]
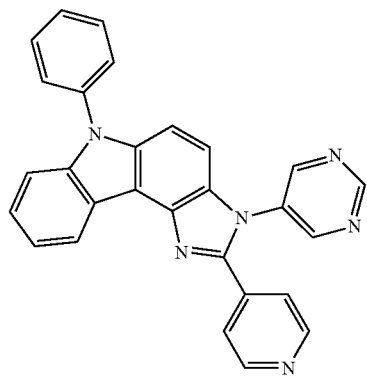
[3-52]
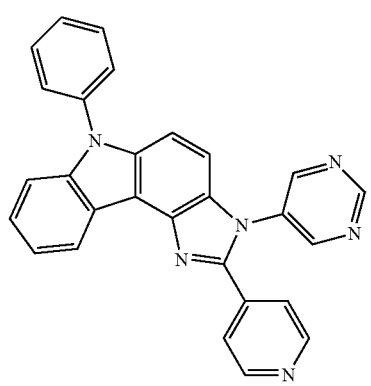
[3-53]
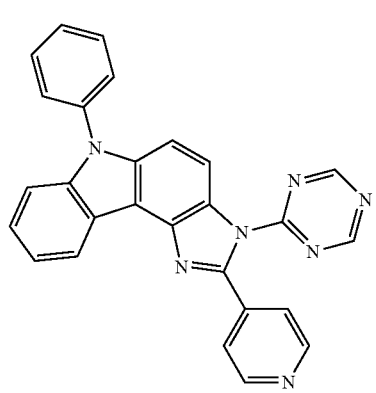
[3-54]
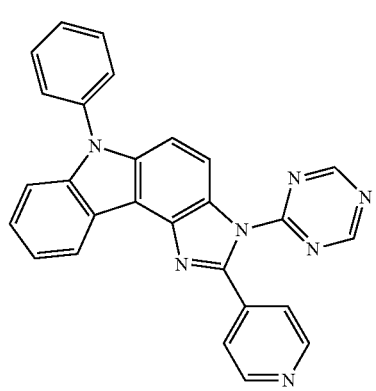

-continued
[3-55]
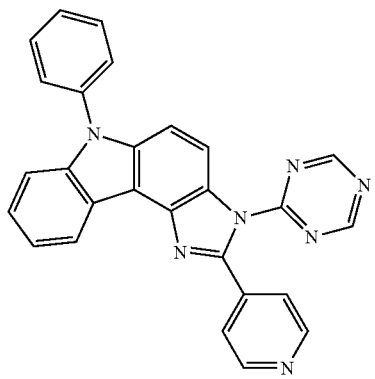
[3-56]
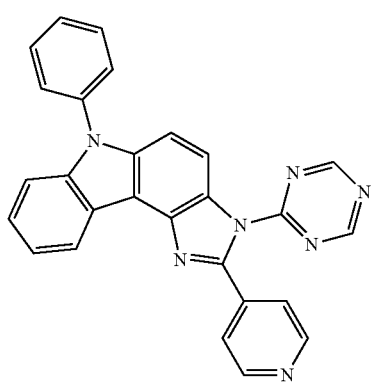
[3-57]
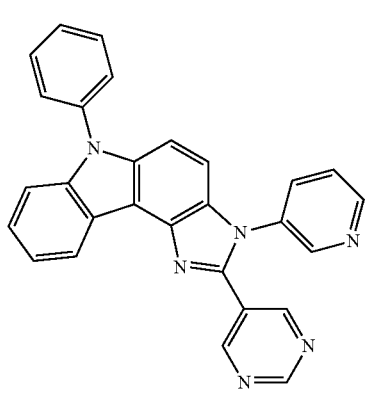
[3-58]
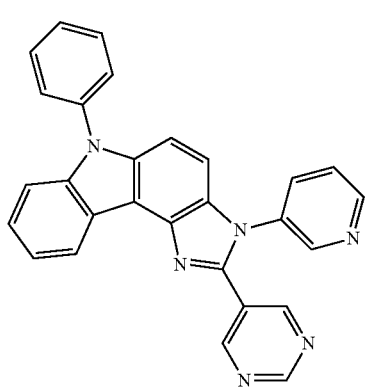
-continued
[3-59]
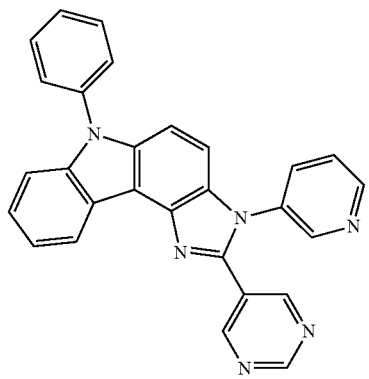
[3-60]
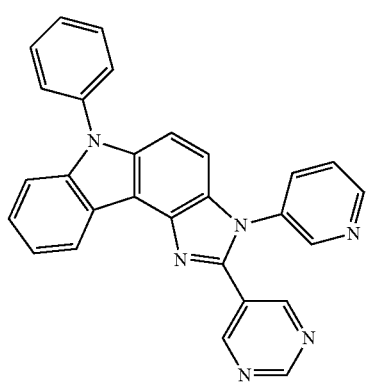
[3-61]
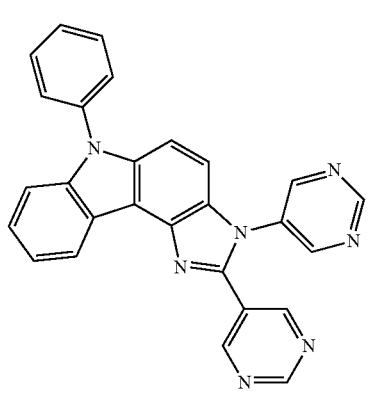
[3-62]
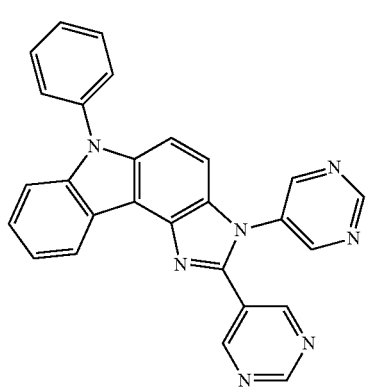

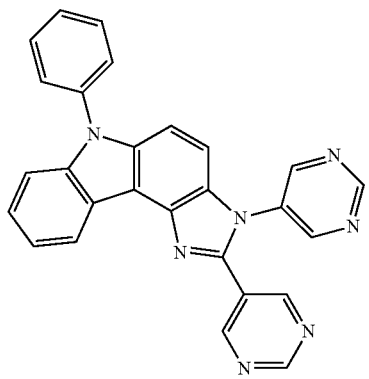
[3-63]
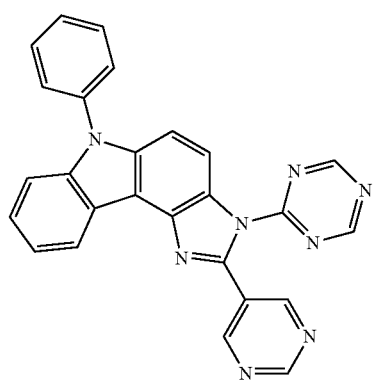
[3-67]
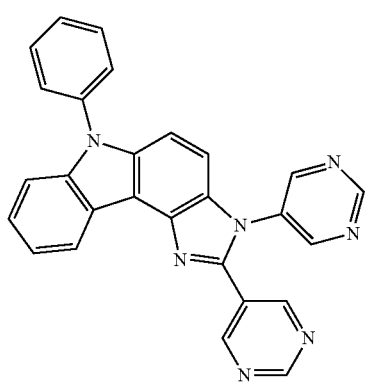
[3-64]
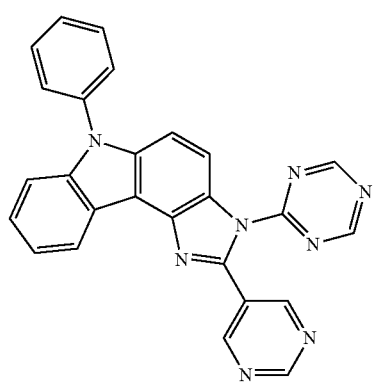
[3-68]
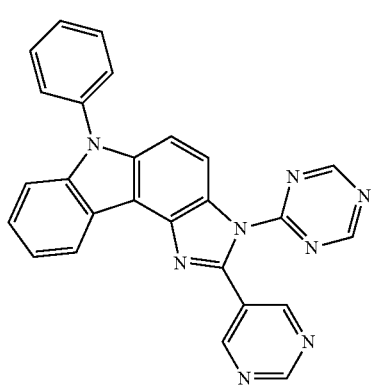
[3-65]
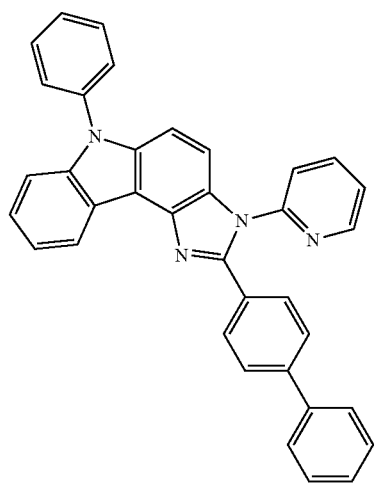
[3-69]
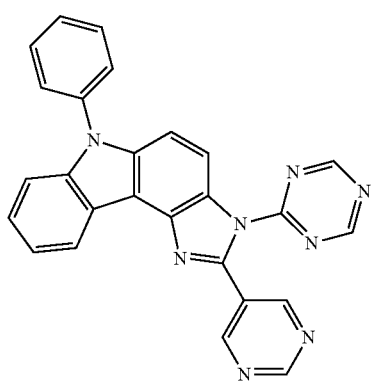
[3-66]
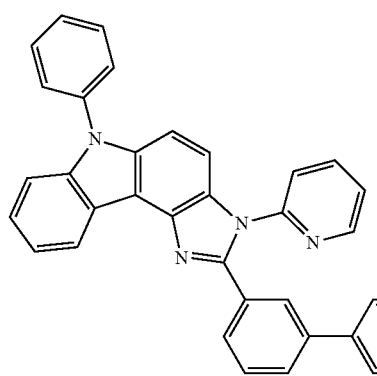
[3-70]

[3-71]
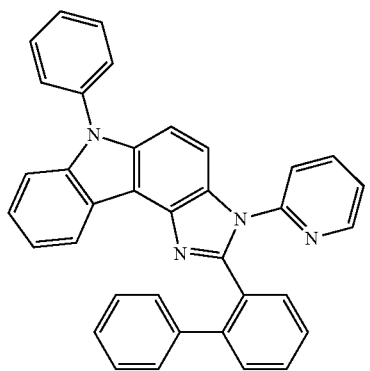
[3-74]
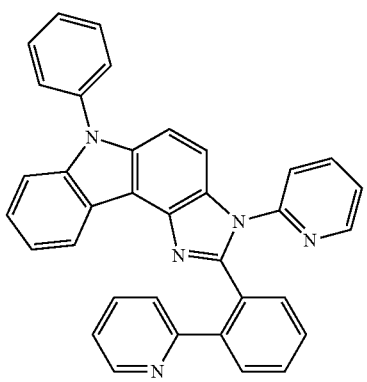
[3-72]
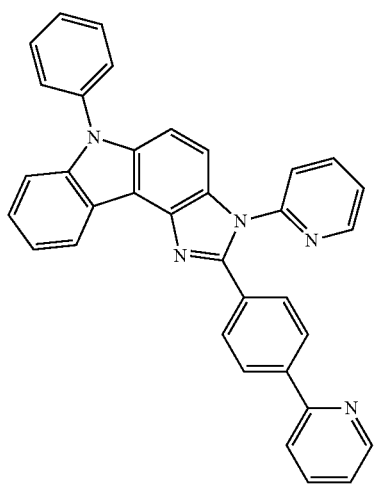
[3-75]
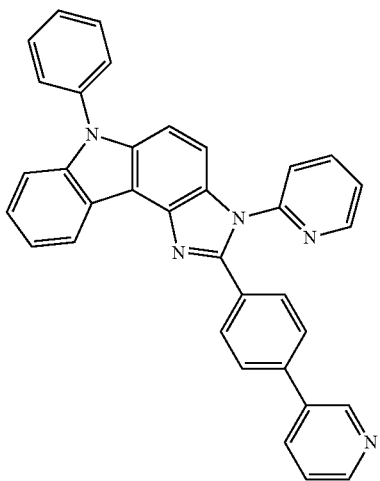
[3-76]
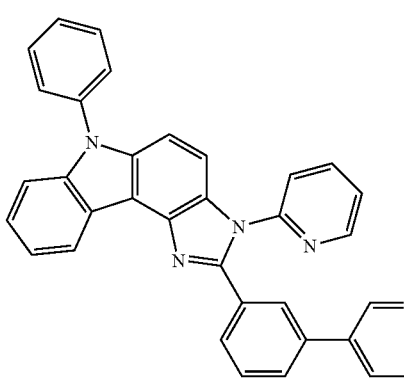
[3-73]
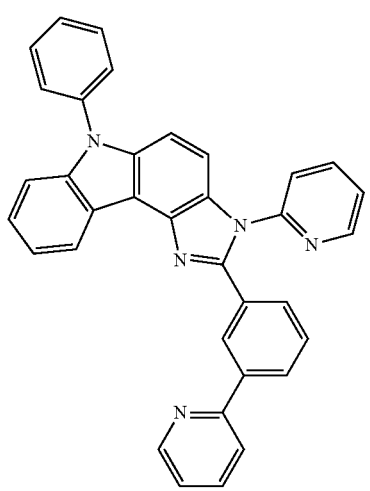
[3-77]
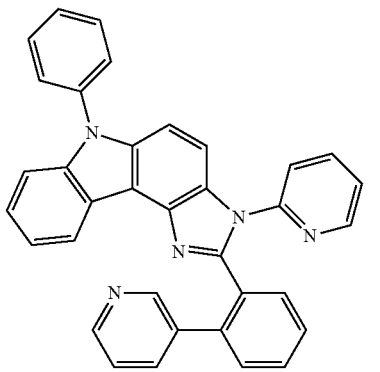

33
-continued
[3-78]
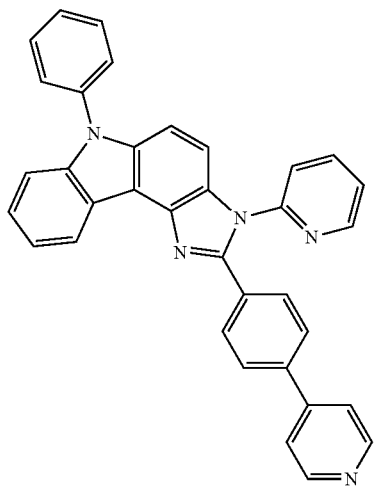
[3-79]
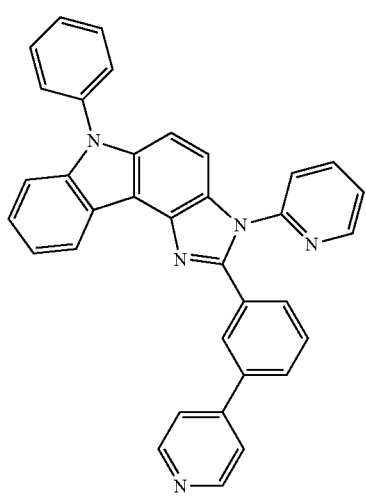
[3-80]
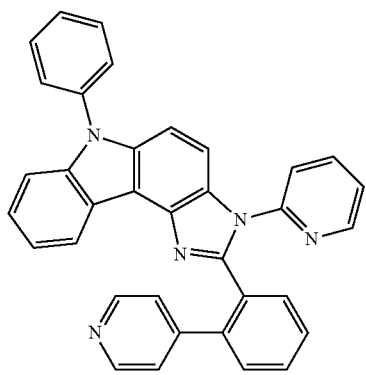
34
-continued
[3-81]
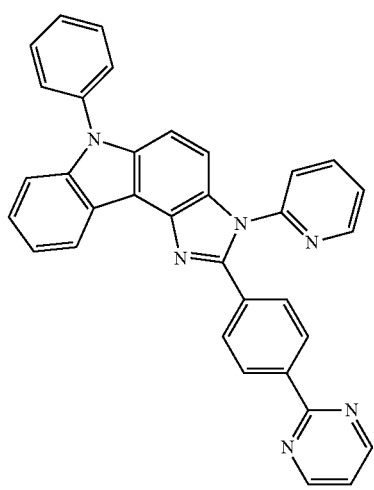
[3-82]
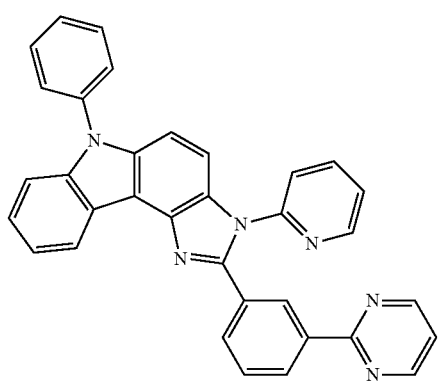
[3-83]
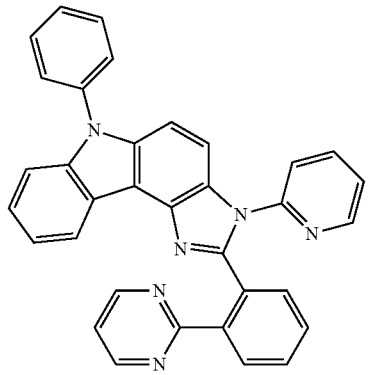

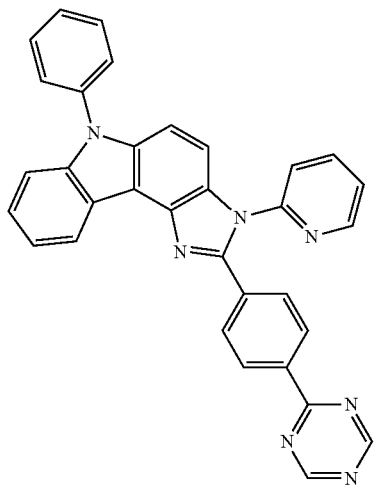
[3-84]
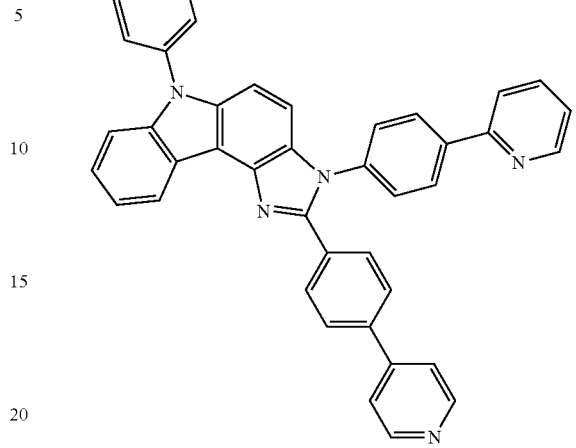
[3-87]
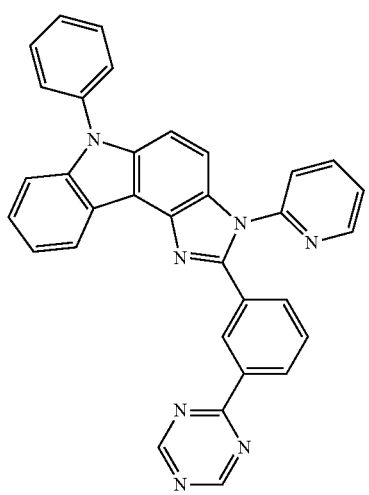
[3-85]
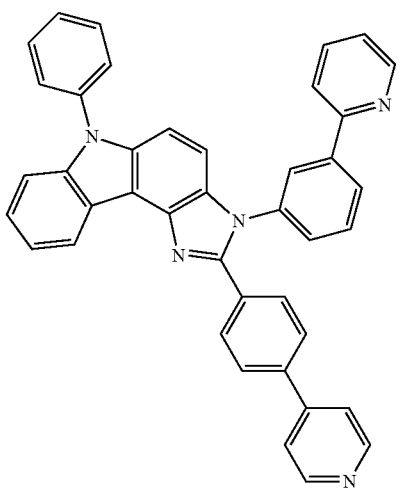
[3-88]
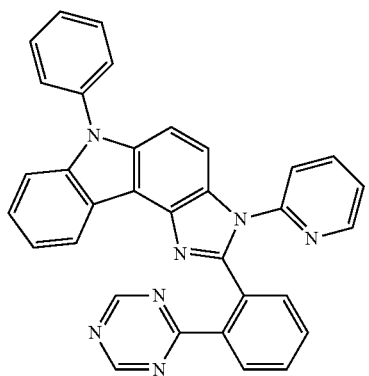
[3-86]
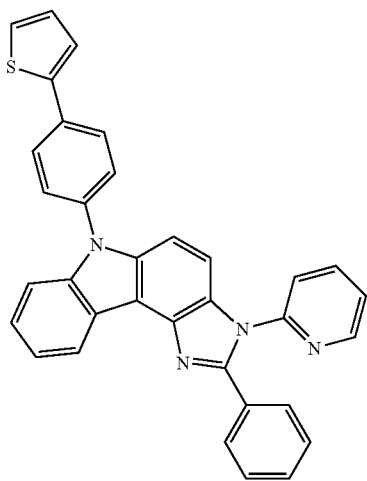
[3-89]

[3-90]
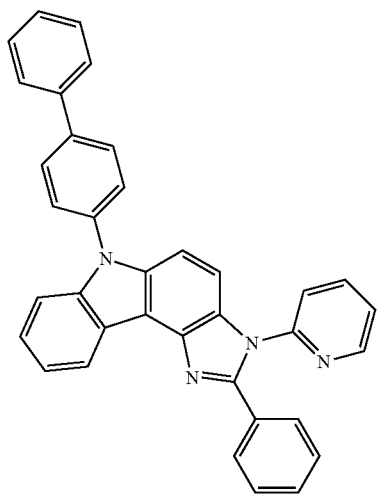
[3-93]
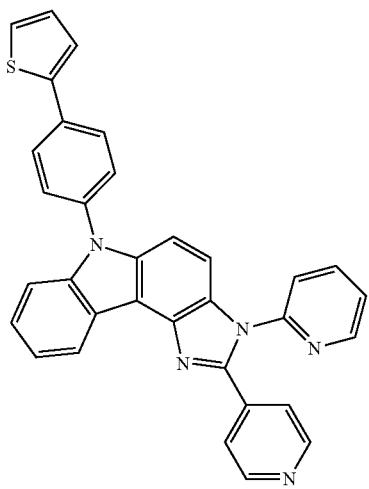
[3-91]
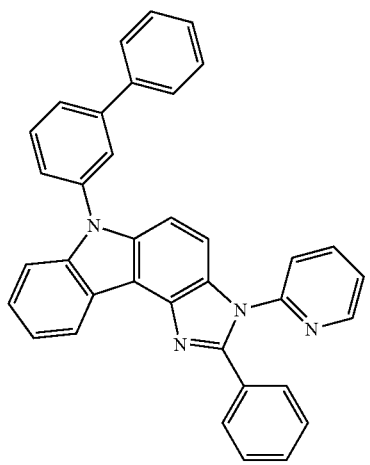
[3-94]
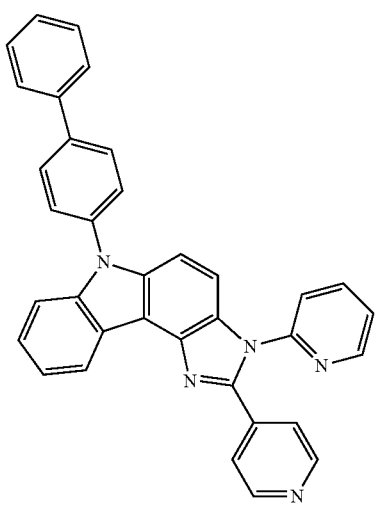
[3-92]
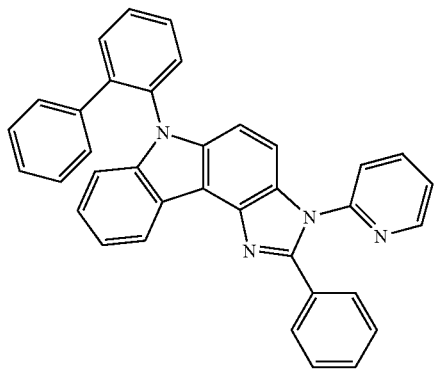
[3-95]
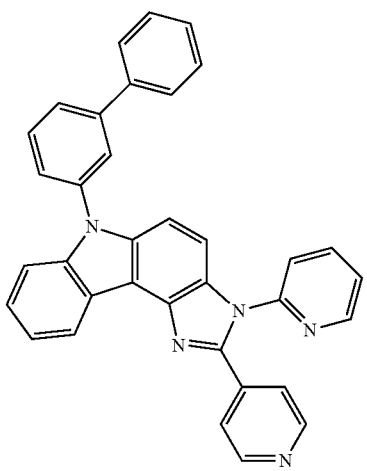

-continued
[3-96]
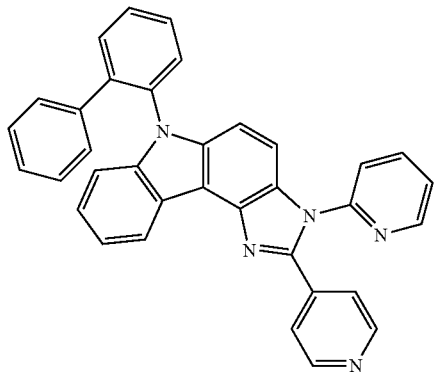
[3-97]
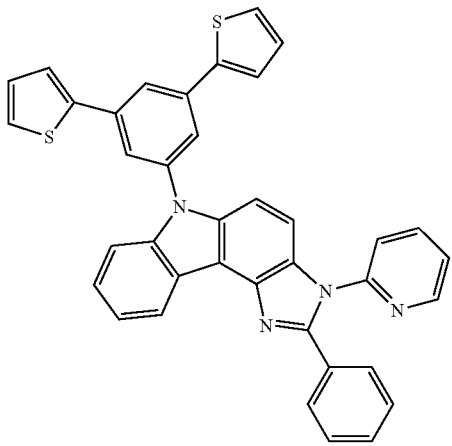
[3-98]
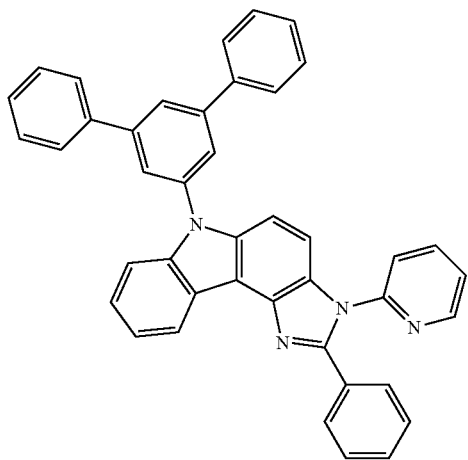
-continued
[3-99]
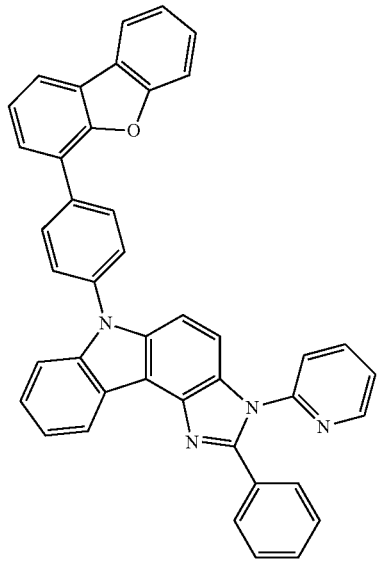
[3-100]
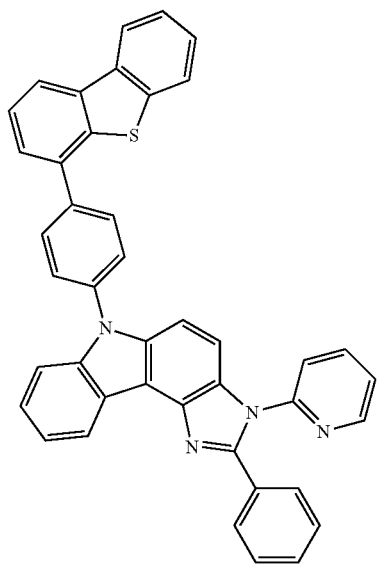
[3-101]
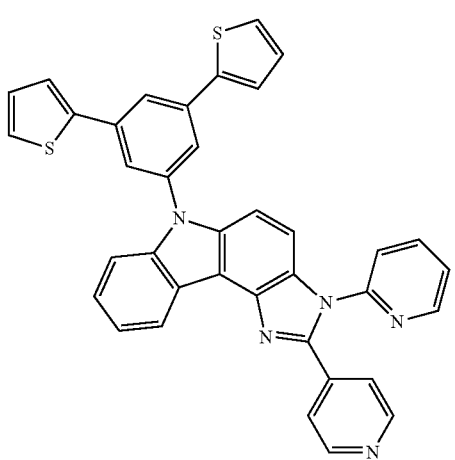

[3-102]
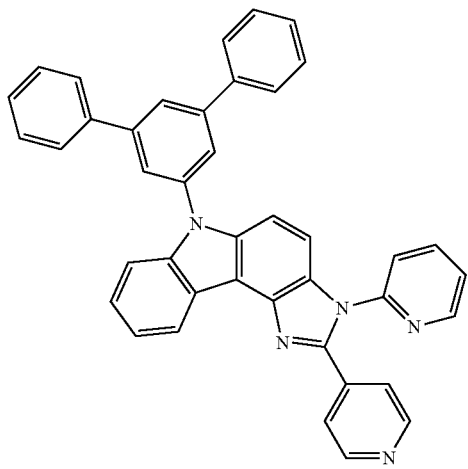
[3-103]
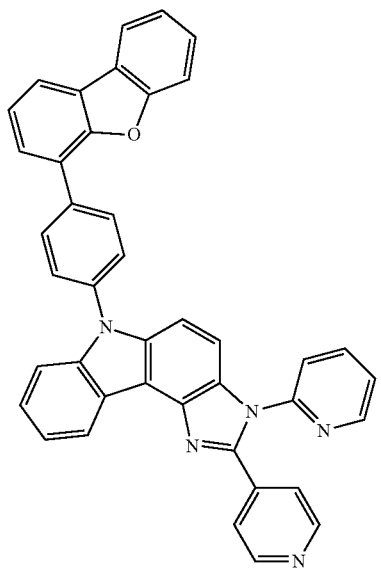
[3-104]
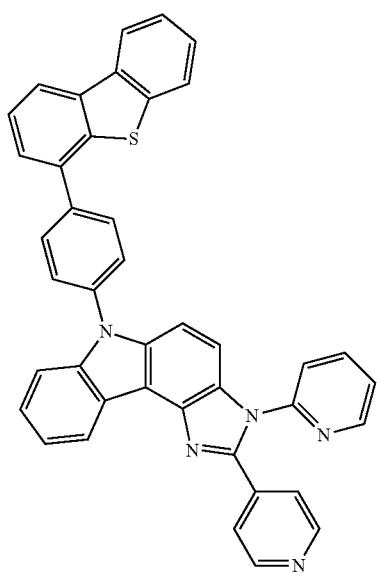
[3-105]
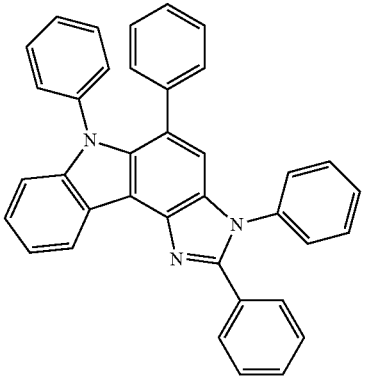
[3-106]
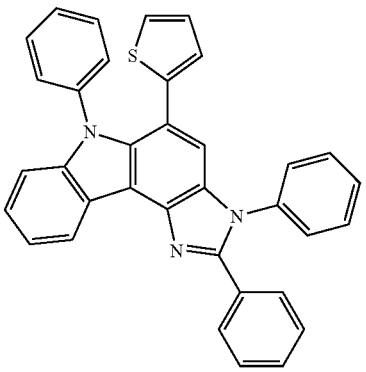
[3-107]
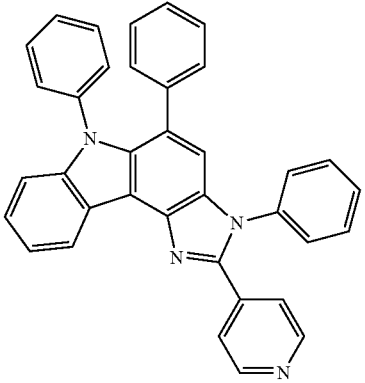
[3-108]
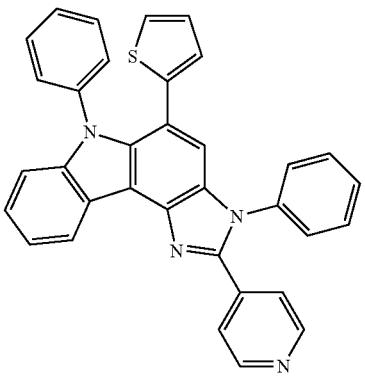

-continued
[3-109]
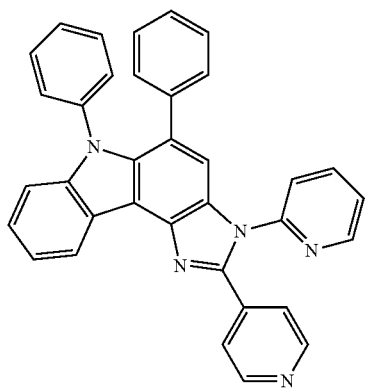
[3-110]
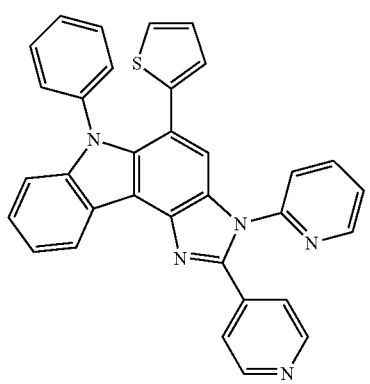
[3-111]
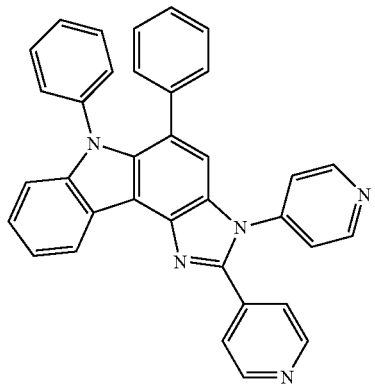
[3-112]
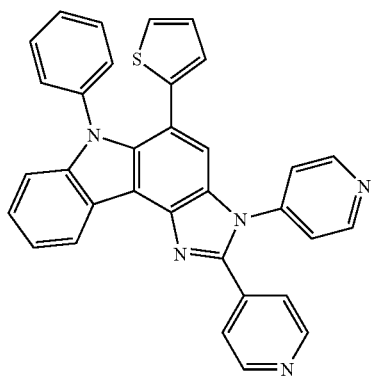
-continued
[3-113]
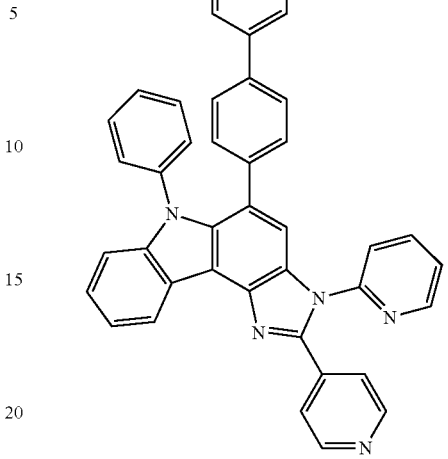
[3-114]
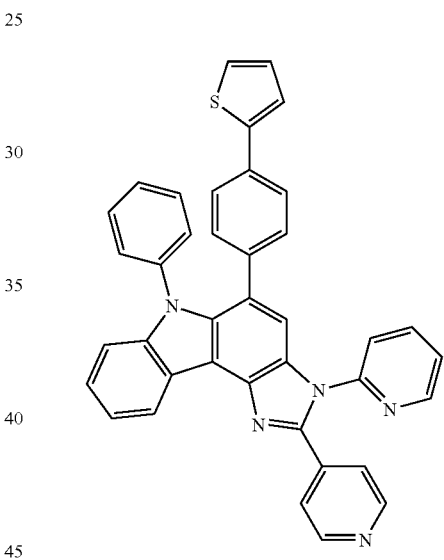
[3-115]
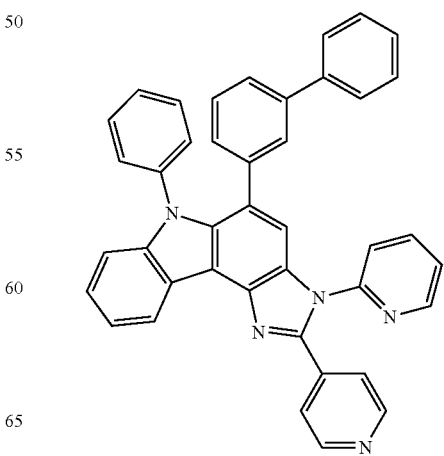

[3-116]
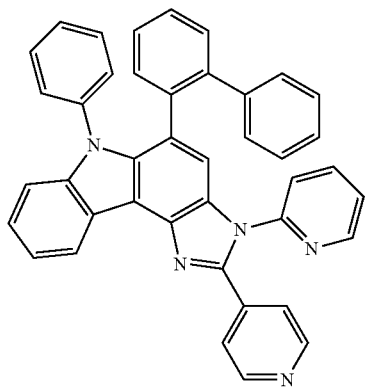
[3-120]
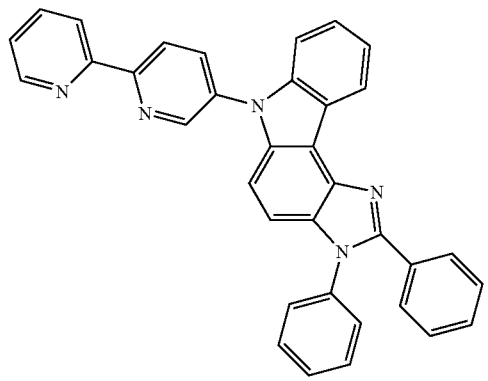
[3-117]
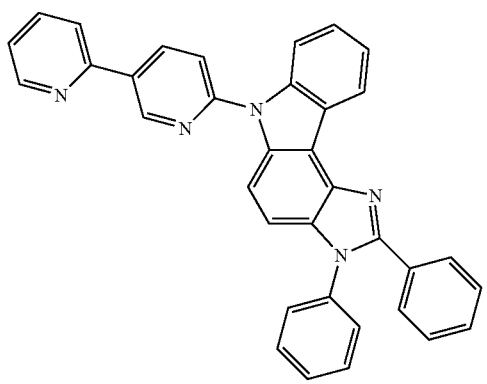
[3-121]
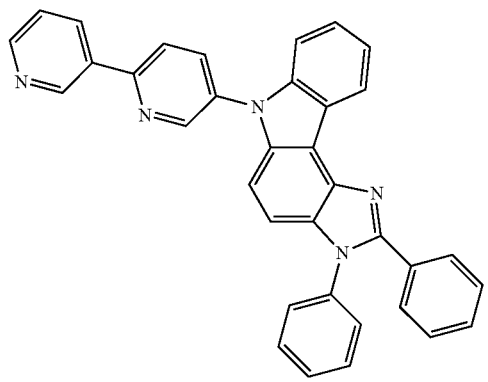
[3-118]
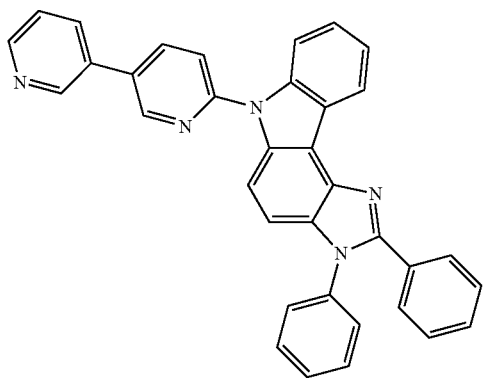
[3-122]
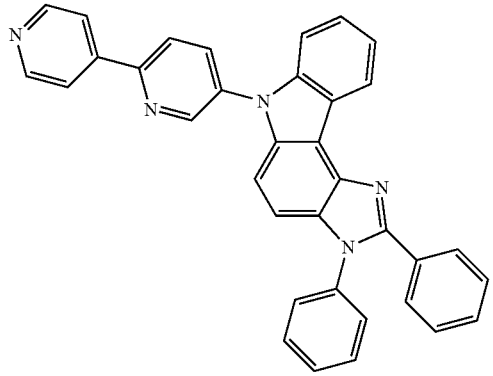
[3-119]
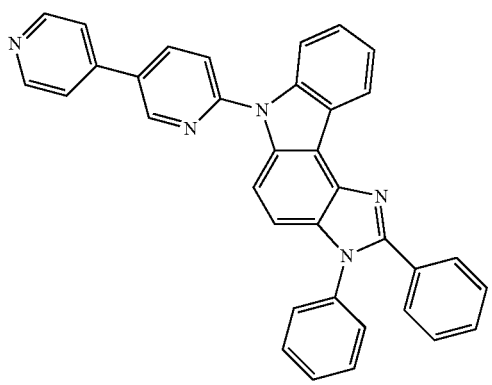
[3-123]
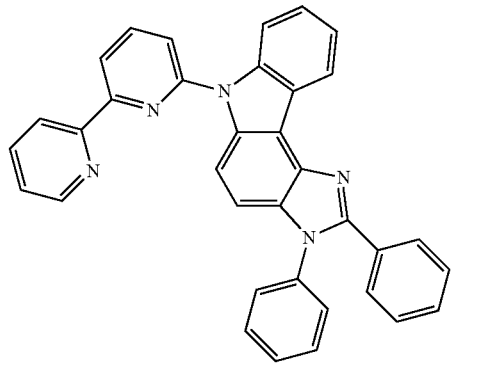

[3-124]
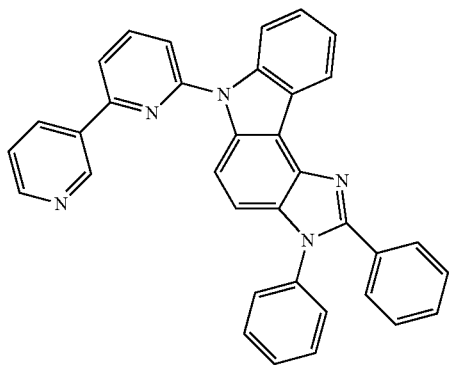
[3-128]
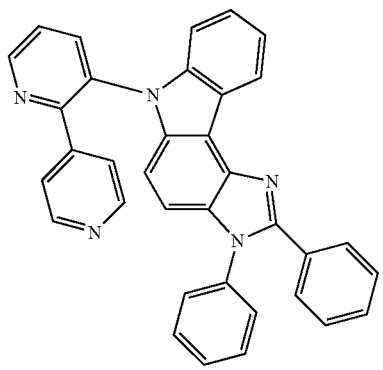
[3-125]
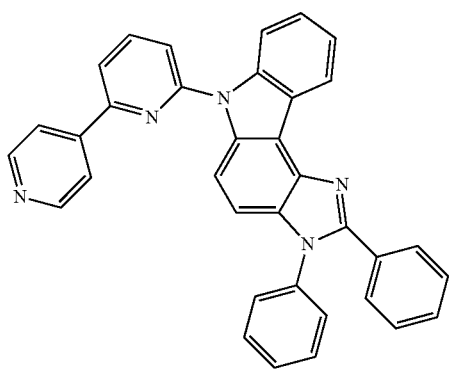
[3-129]
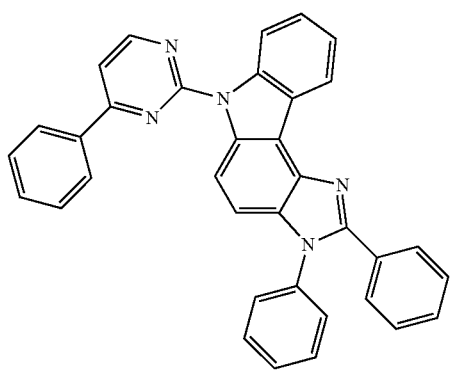
[3-126]
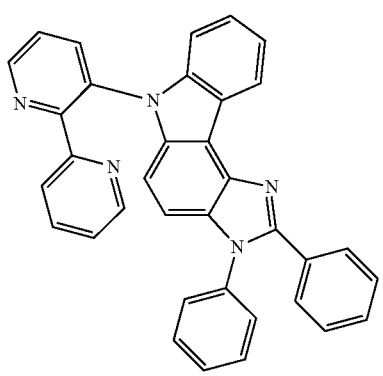
[3-130]
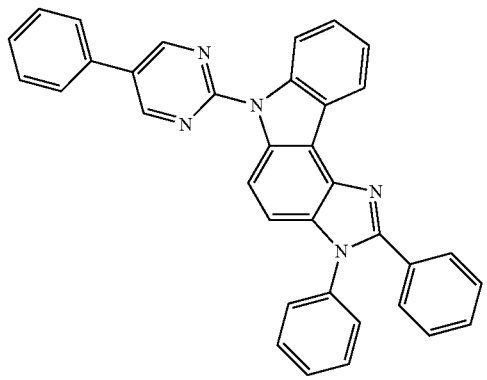
[3-127]
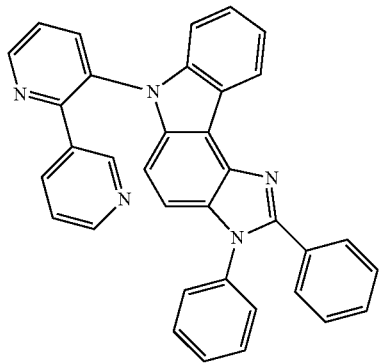
[3-131]
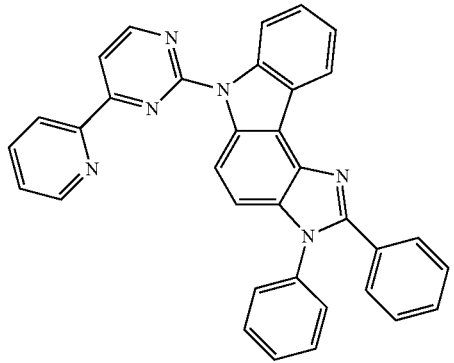

-continued
[3-132]
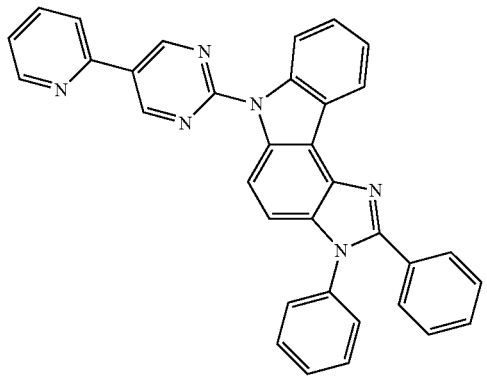
[3-136]
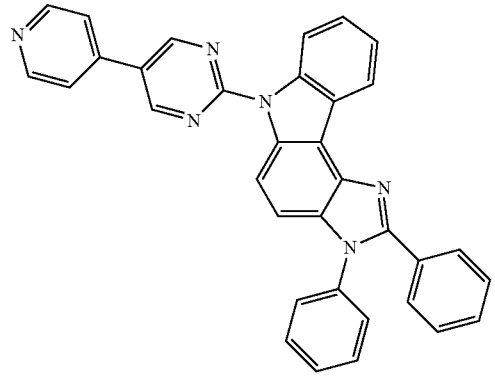
[3-133]
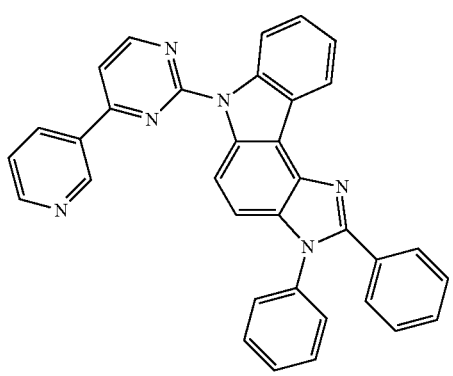
[3-137]
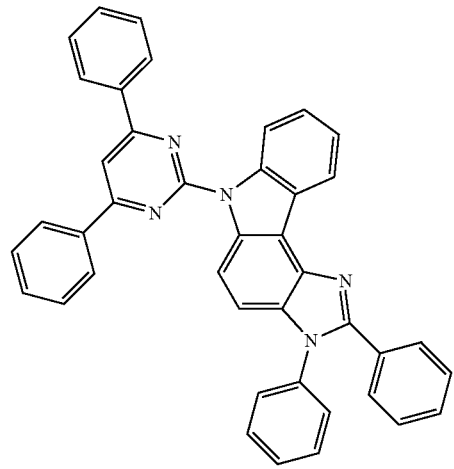
[3-134]
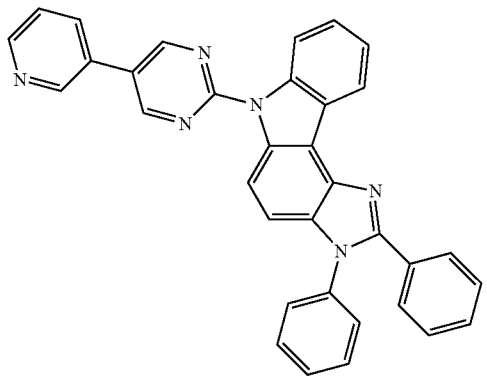
[3-135]
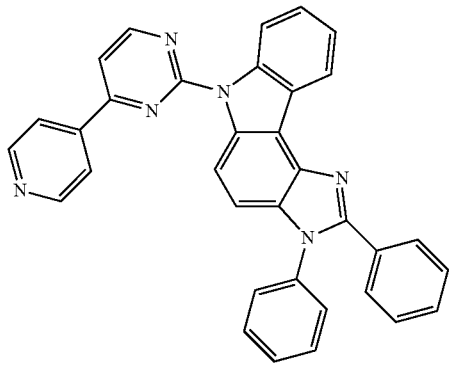
[3-138]
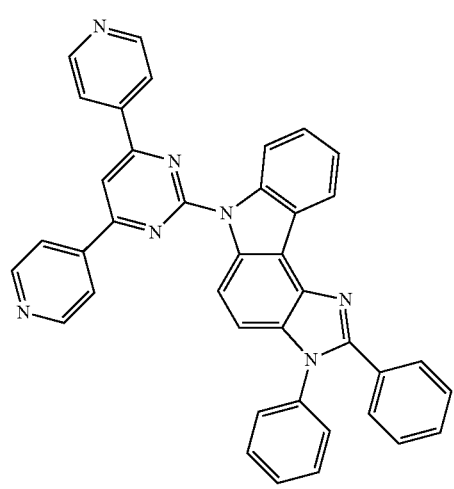

[3-139]
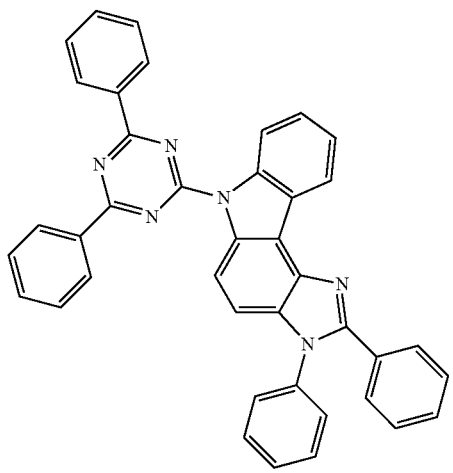
[3-142]
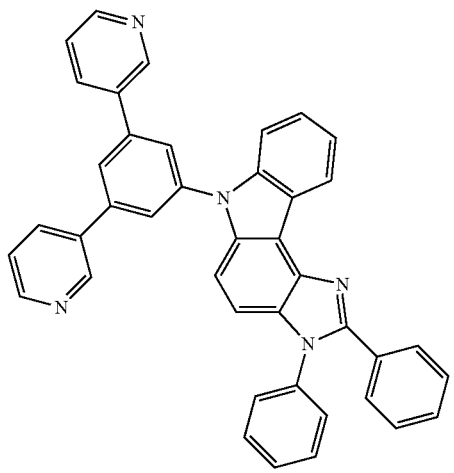
[3-140]
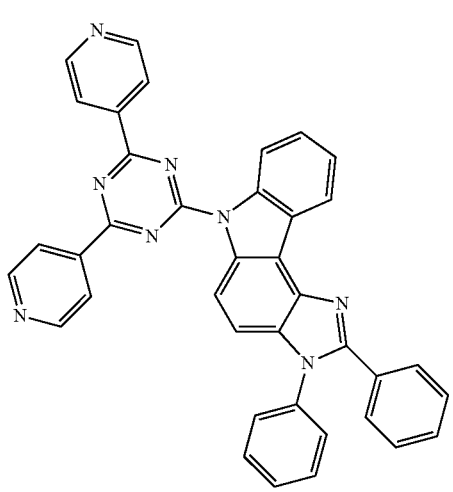
[3-143]
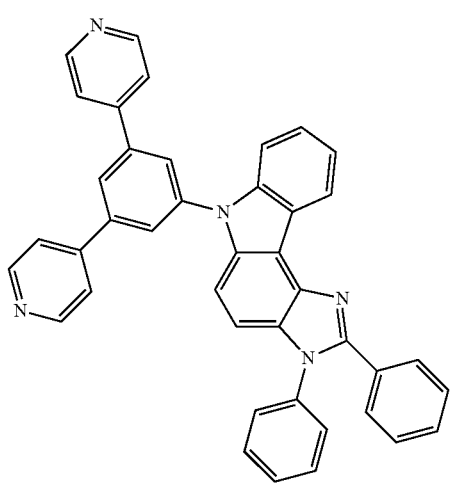
[3-141]
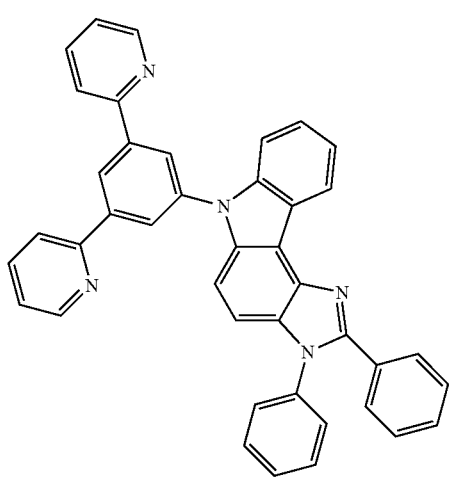
[3-144]
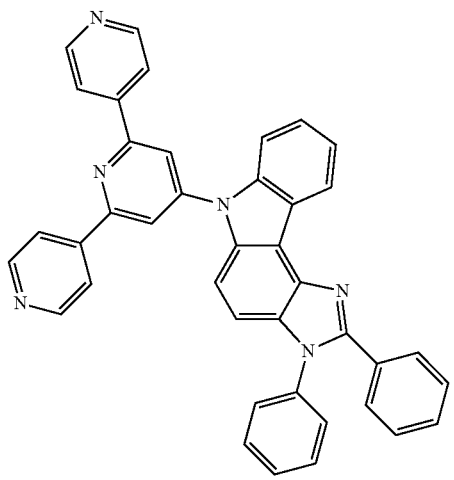

[3-145]
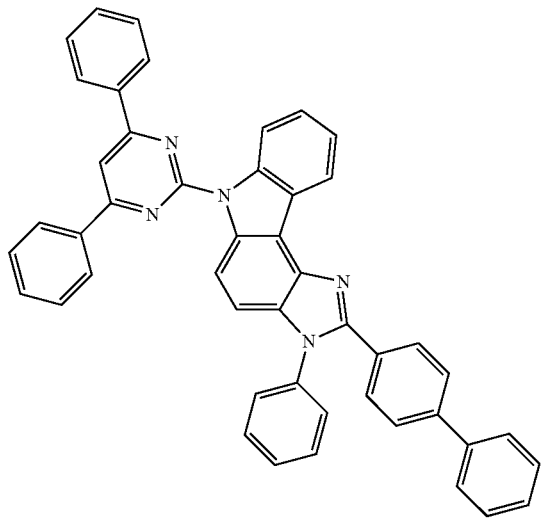
[3-146]
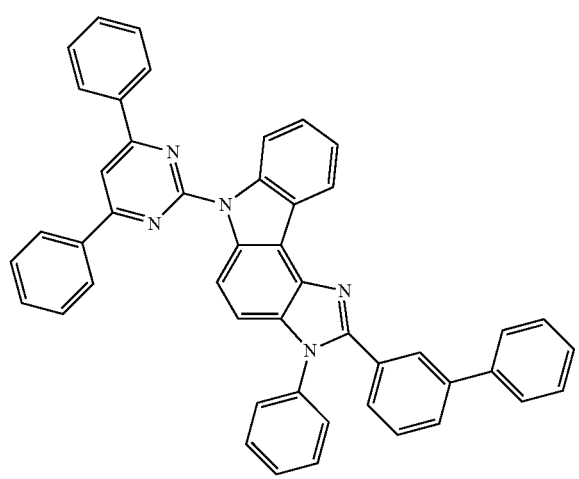
[3-147]
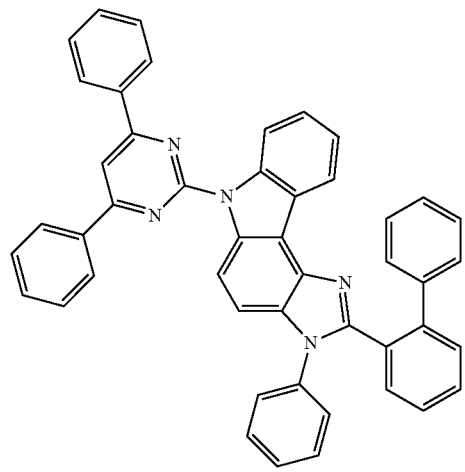
[3-148]
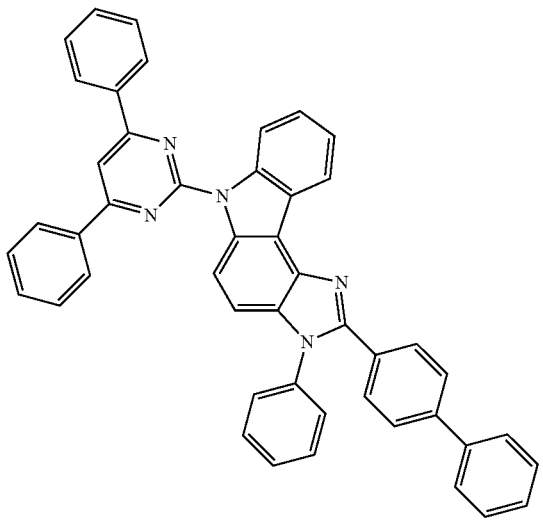
[3-149]
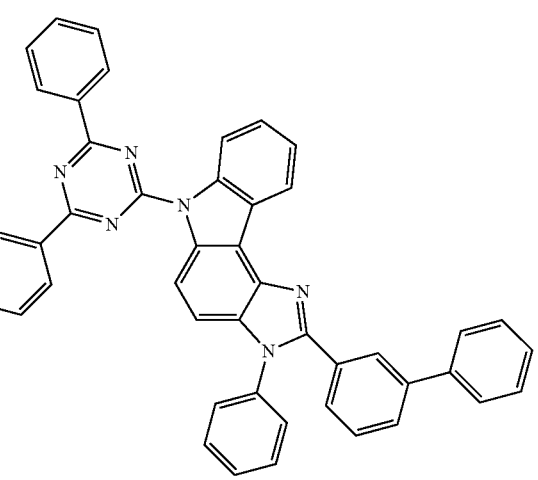
[3-150]
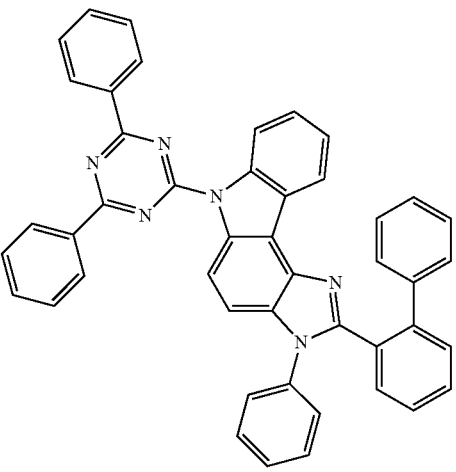

[3-151]
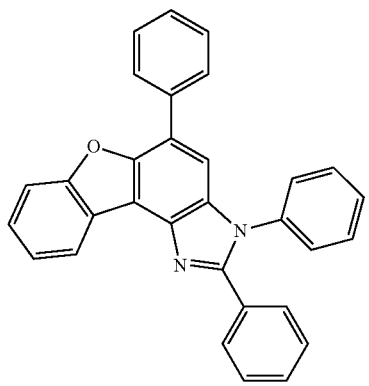
[3-152]
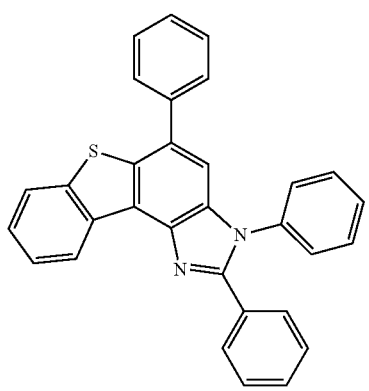
[3-153]
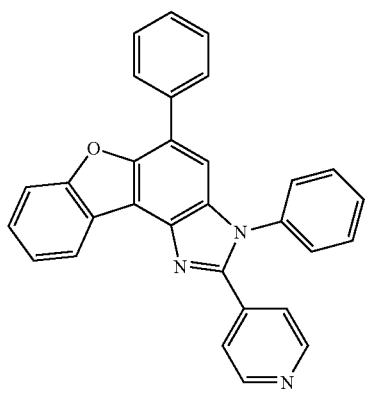
[3-154]
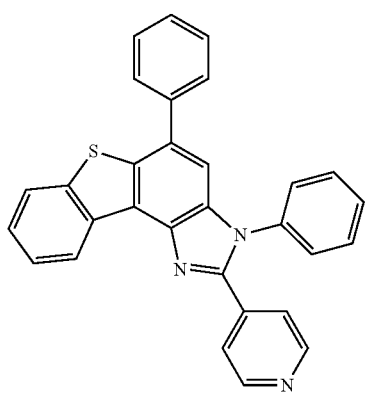
[3-155]
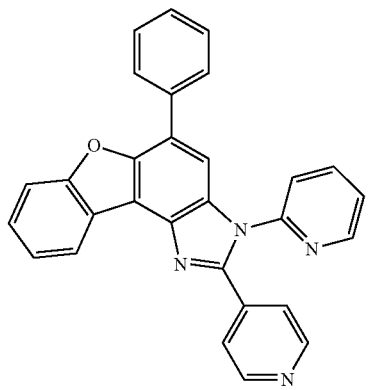
[3-156]
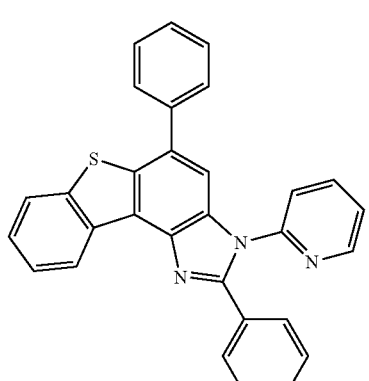
[3-157]
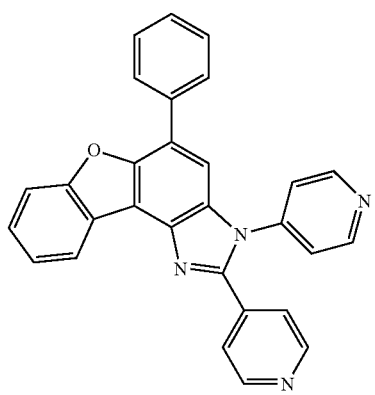
[3-158]
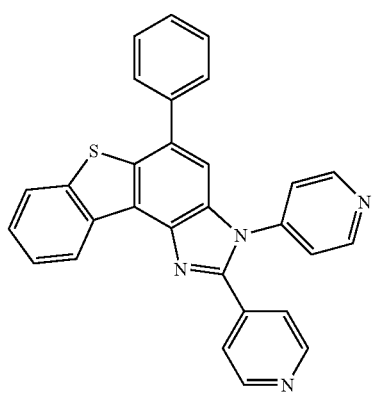

[5-1]
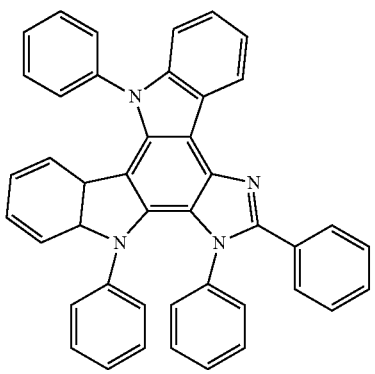
[5-2]
[5-3]
[5-4]
[5-5]
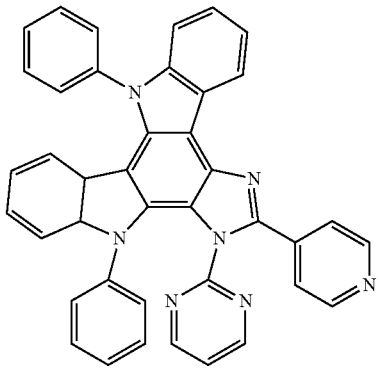
[5-6]
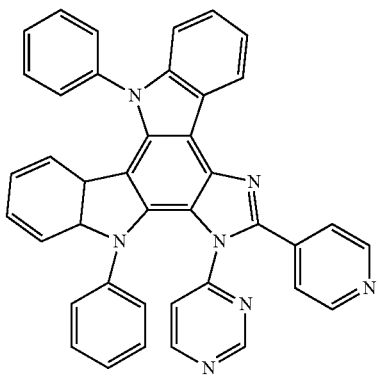
[5-7]
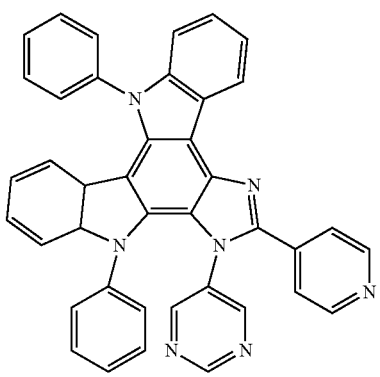
[5-8]
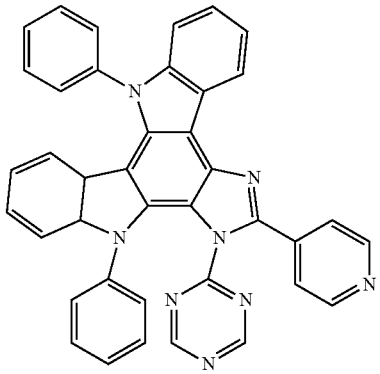

[5-9]
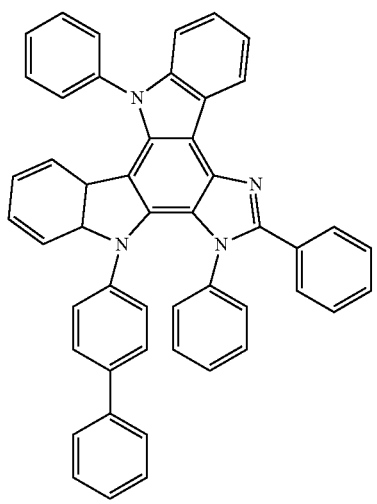
[5-10]
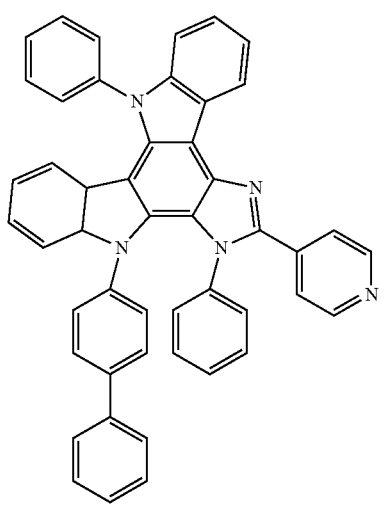
[5-11]
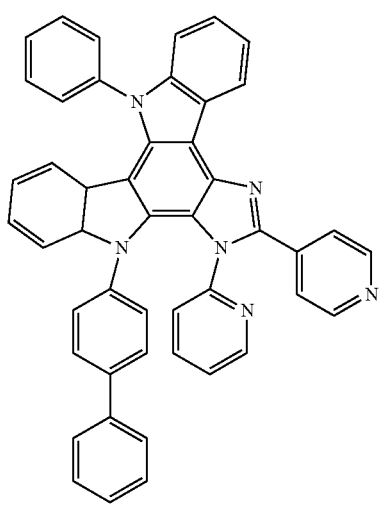
[5-12]
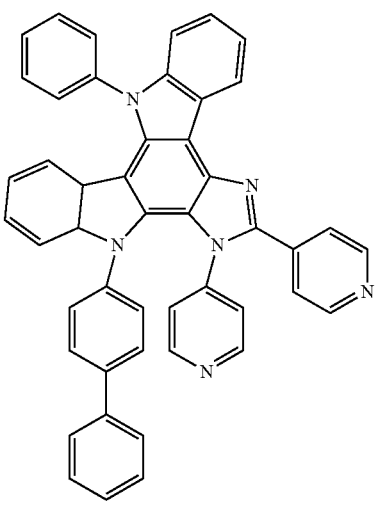
[5-13]
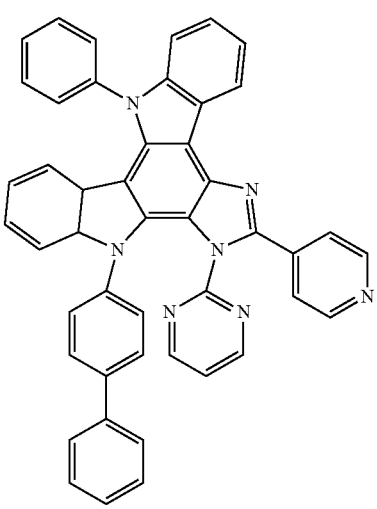
[5-14]
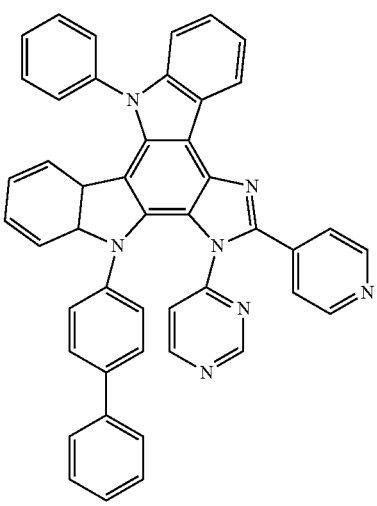

[5-15]
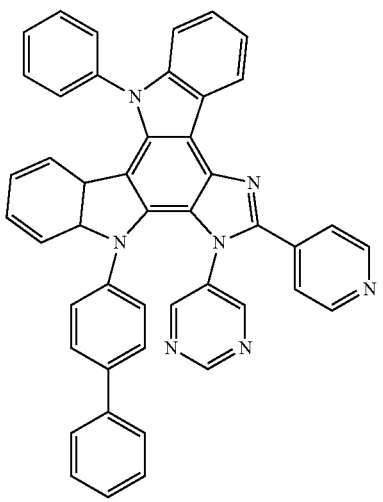
[5-16]
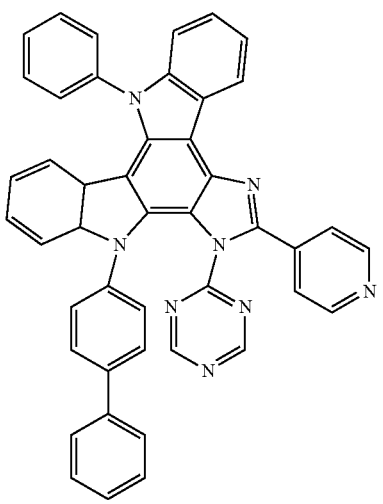
[5-17]
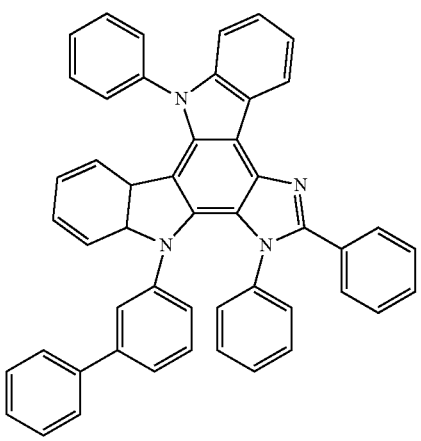
[5-18]
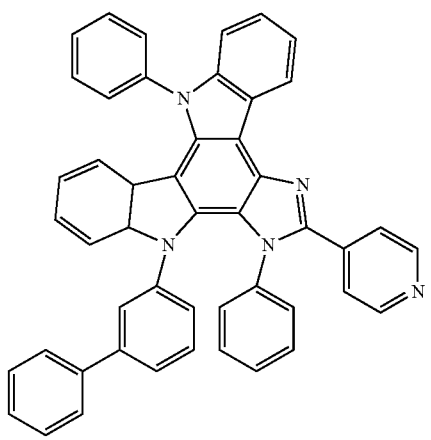
[5-19]
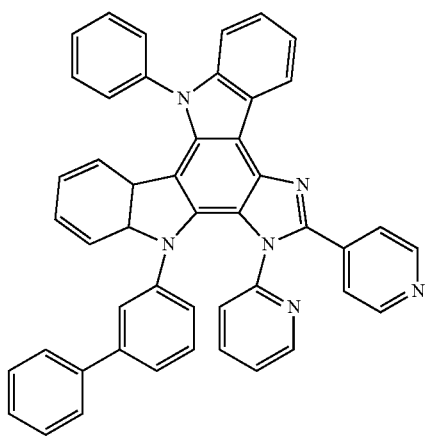
[5-20]
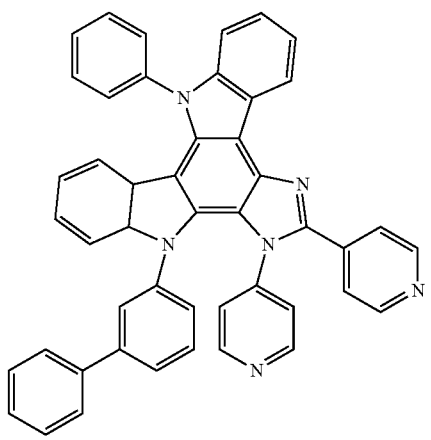

[5-21]
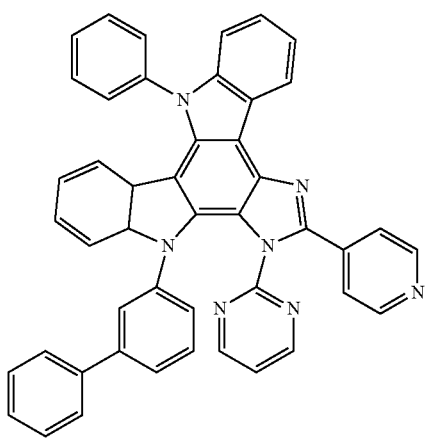
[5-22]
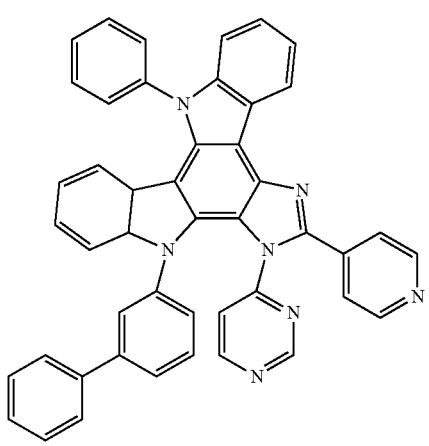
[5-23]
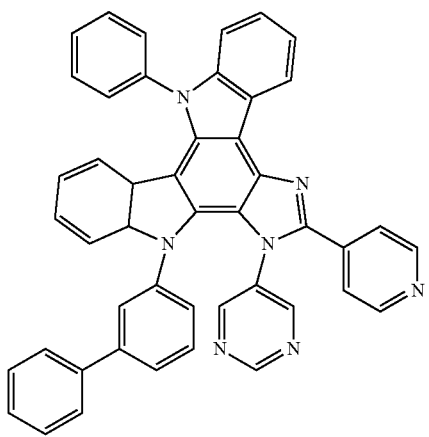
[5-24]
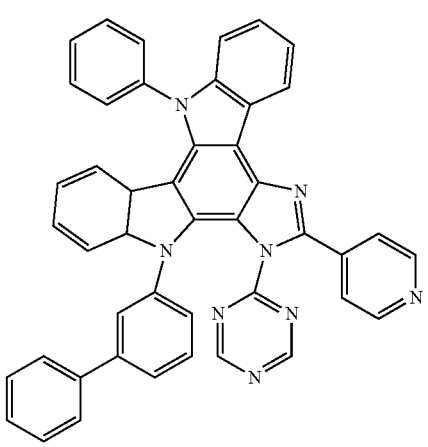
[5-25]
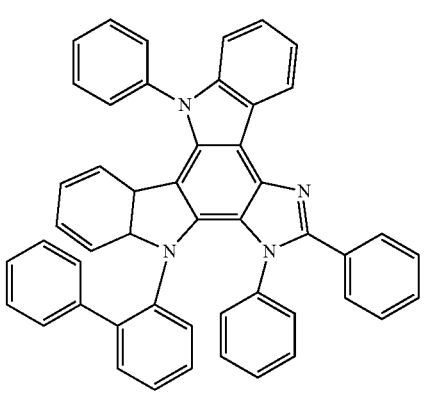
[5-26]
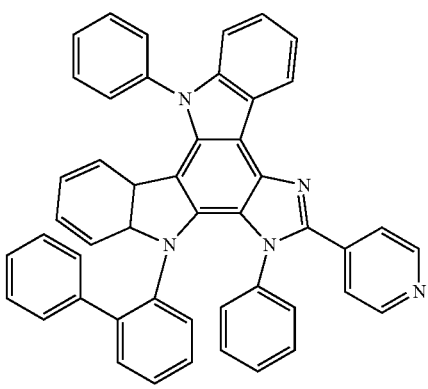
[5-27]
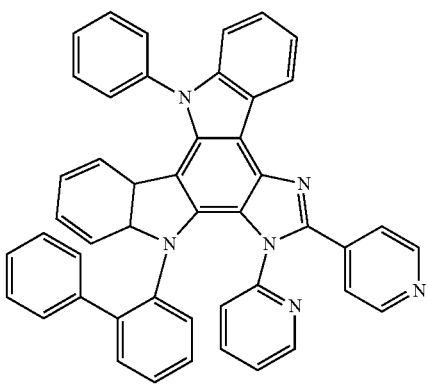

[5-28]
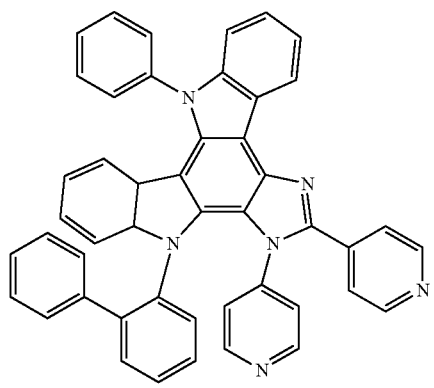
[5-29]
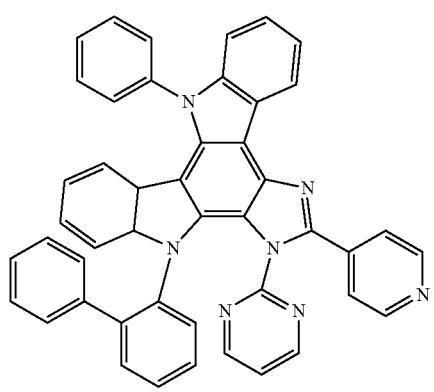
[5-30]
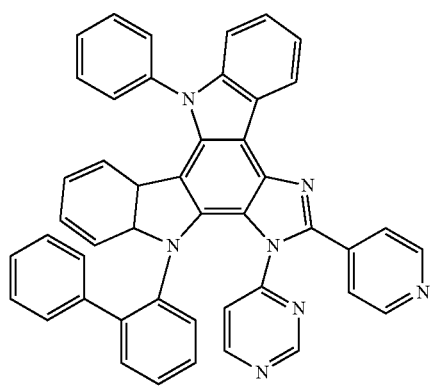
[5-31]
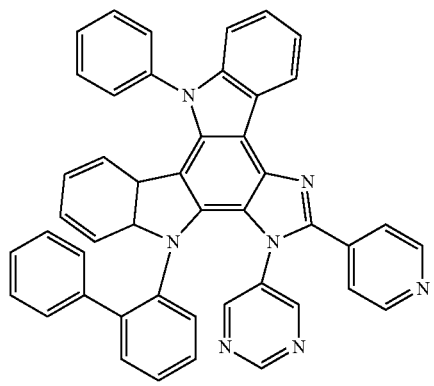
[5-32]
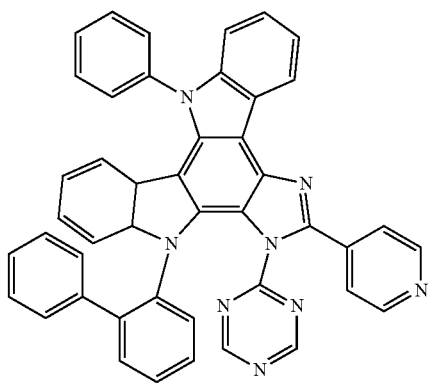
[5-33]
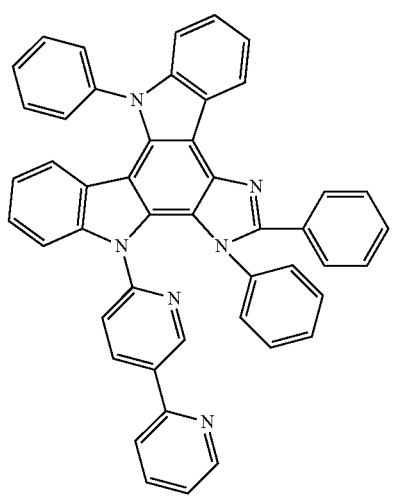
[5-34]
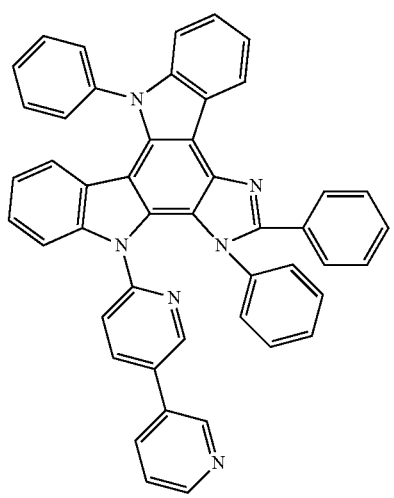

[5-35]
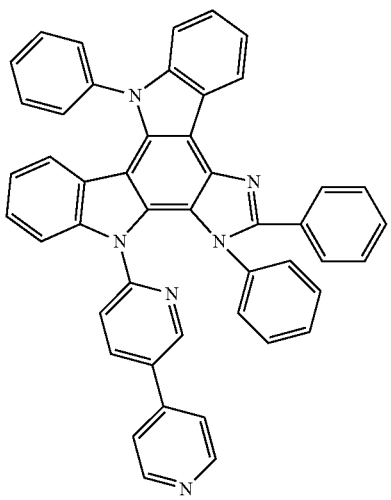
[5-38]
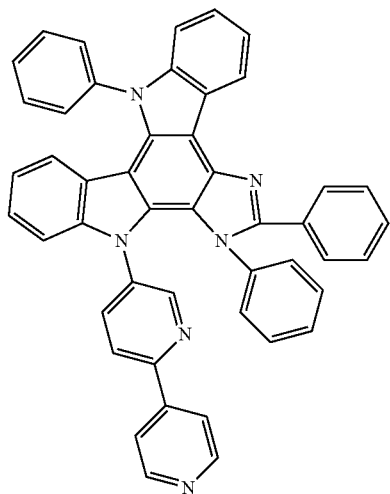
[5-36]
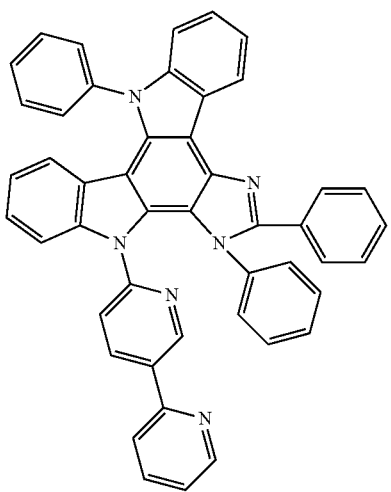
[5-39]
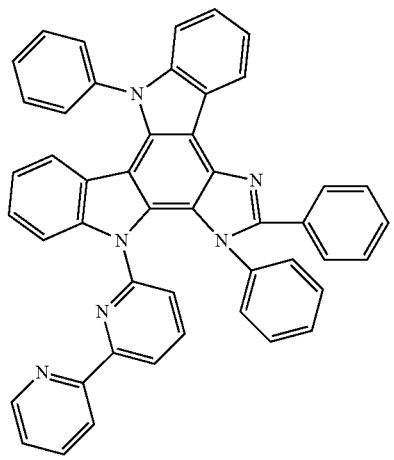
[5-37]
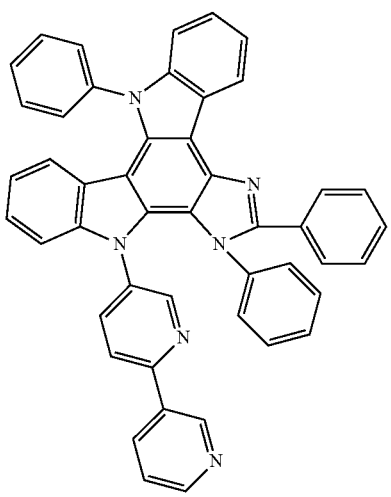
[5-40]
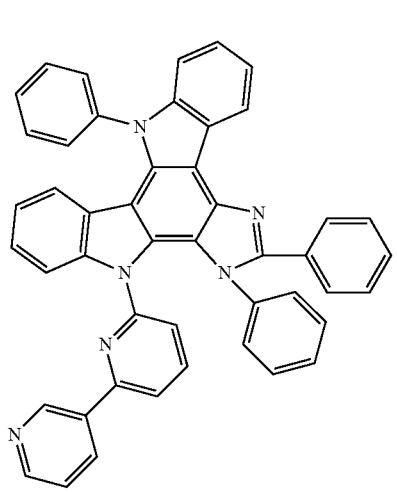

[5-41]
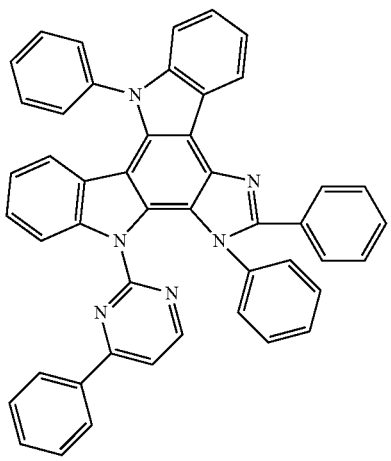
[5-42]
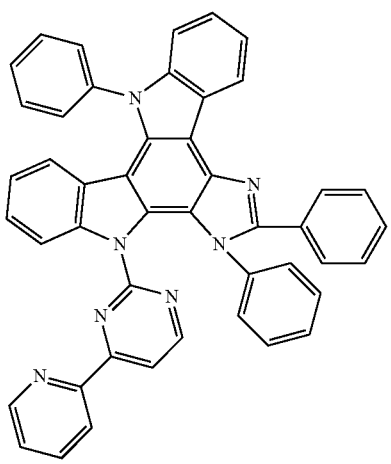
[5-43]
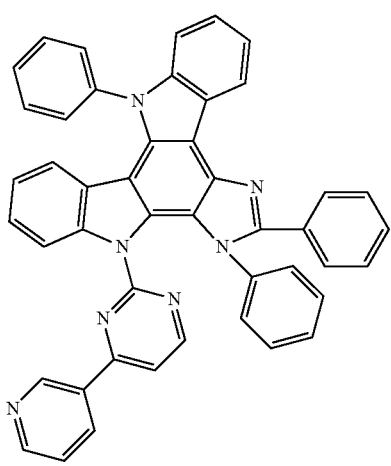
[5-44]
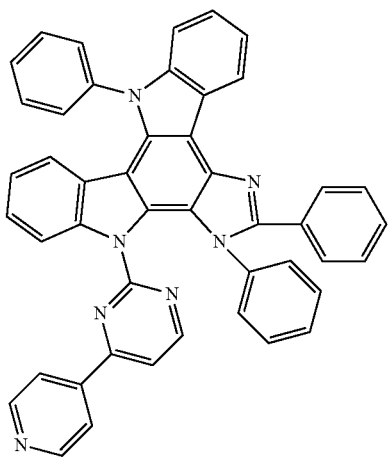
[5-45]
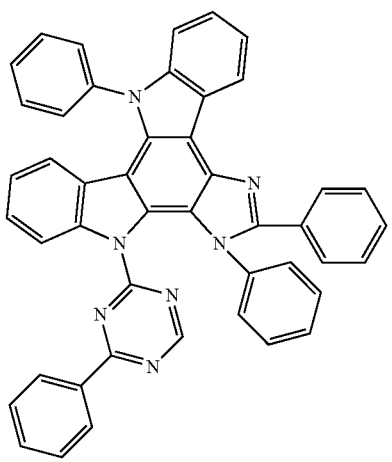
[5-46]
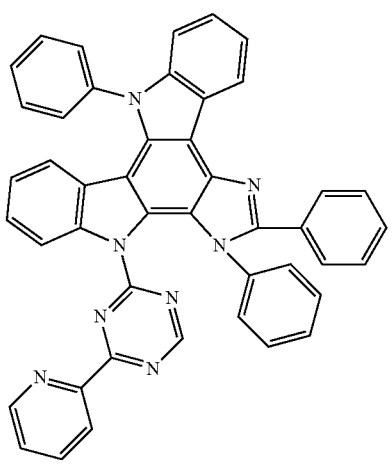

[5-47]
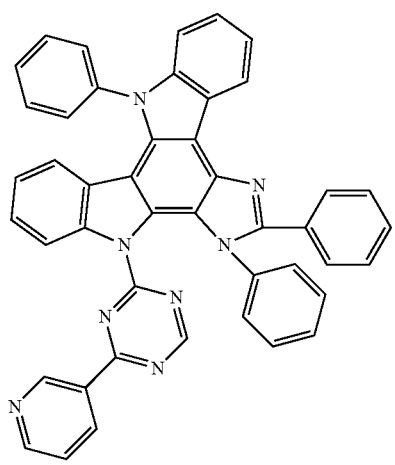
[5-50]
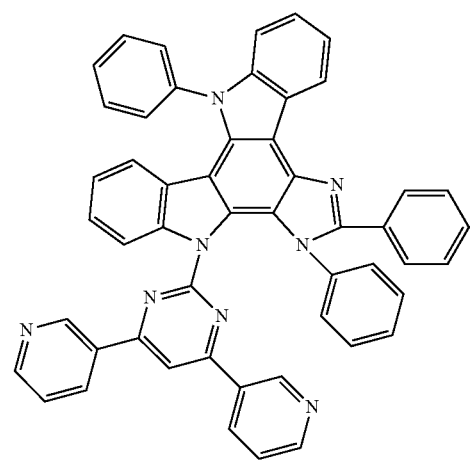
[5-48]
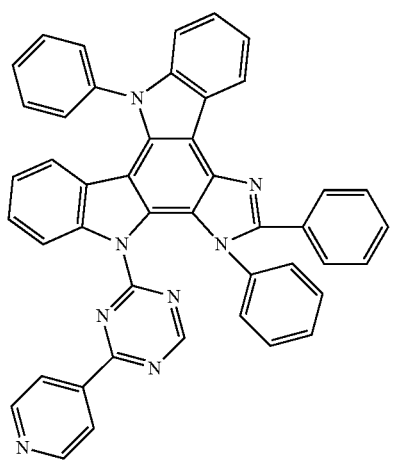
[5-51]
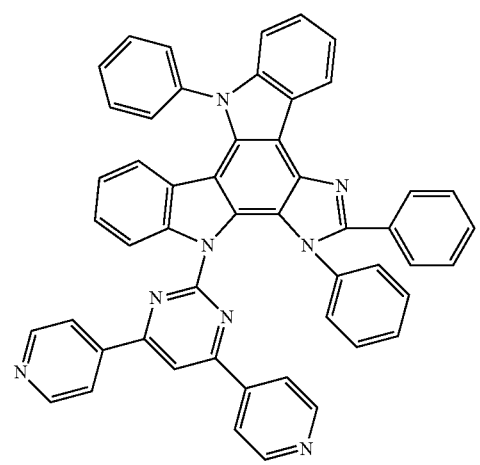
[5-49]
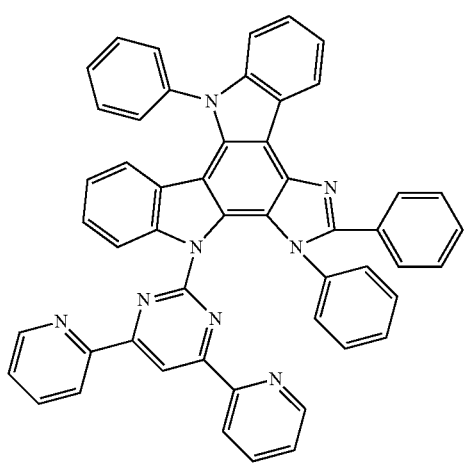
[5-52]
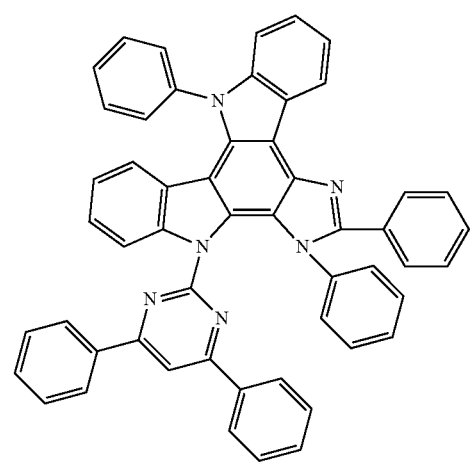

[5-53]
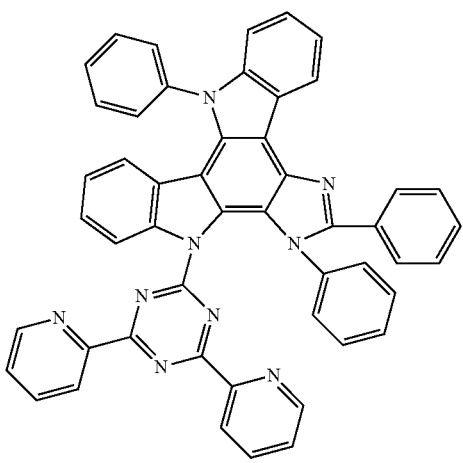

[5-54]
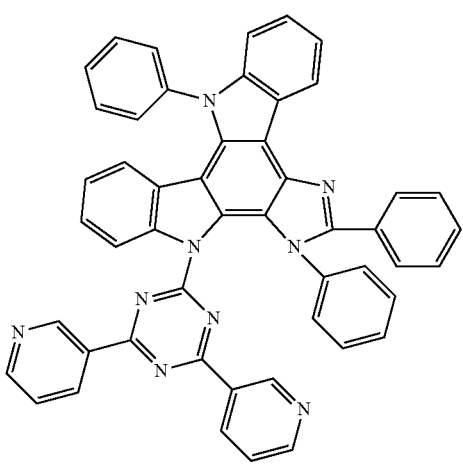

[5-55]
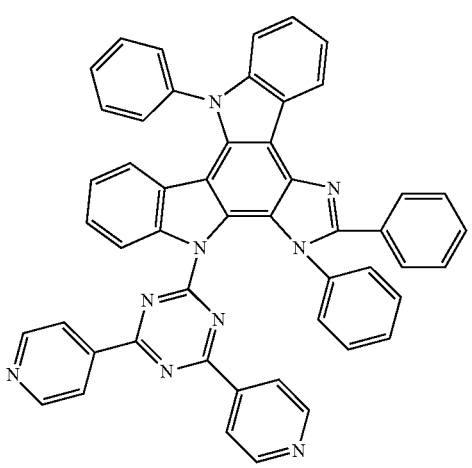

[5-56]
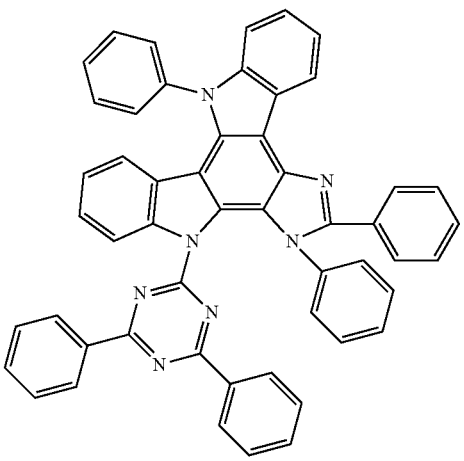

Hereinafter, an organic optoelectric device including the organic compound for an organic optoelectric device according to an example embodiment is described.

According to the present example embodiment, the organic optoelectric device may be a device to convert electrical energy into photo energy or vice versa, e.g., an organic photoelectric device, an organic light emitting diode, an organic solar cell, an organic photo-conductor drum, etc.

Herein, an organic light emitting diode as one example of an organic optoelectric device is described referring to drawings.

Figure 2:
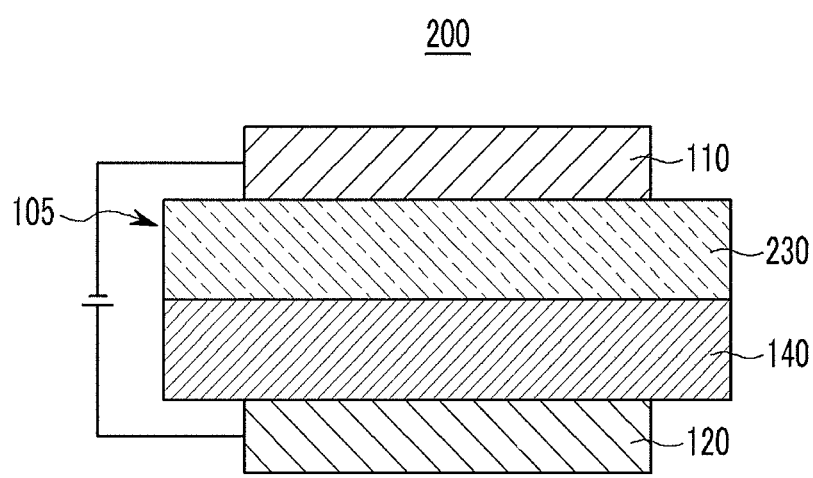

FIGS. 1 and 2 illustrate cross-sectional views of organic light emitting diodes according to example embodiments.

Referring to FIGS. 1 and 2, organic optoelectric devices 100 and 200 according to an example embodiment include an anode 120 and a cathode 110 facing each other, and an organic layer 105 interposed between the anode 120 and cathode 110.

The anode 120 may include an anode material having a large work function to help hole injection into an organic thin layer. The anode material may include: a metal such as nickel, platinum, vanadium, chromium, copper, zinc, and gold, or alloys thereof; a metal oxide such as zinc oxide, indium oxide, indium tin oxide (ITO), and indium zinc oxide (IZO); a combined metal and oxide such as ZnO:Al or $SnO_2$:Sb; or a conductive polymer such as poly(3-methylthiophene), poly[3,4-(ethylene-1,2-dioxy)thiophene](PEDT), polypyrrole, and polyaniline; etc. In an implementation a transparent electrode including indium tin oxide (ITO) is included as an anode.

The cathode 110 may include a cathode material having a small work function to help electron injection into an organic thin layer. The cathode material may include: a metal such as magnesium, calcium, sodium, potassium, titanium, indium, yttrium, lithium, gadolinium, aluminum, silver, tin, and lead, or alloys thereof; or a multi-layered material such as LiF/Al, Liq/Al, $LiO_2$/Al, LiF/Ca, LiF/Al, and $BaF_2$/Ca; etc. In an implementation, a metal electrode including aluminum is included as a cathode.

In the example embodiment shown in FIG. 1, the organic light emitting diode 100 includes an organic thin layer 105 including only an emission layer 130.

The organic thin layer may also function as a hole injection layer (HIL) or a hole transport layer (HTL).

In the example embodiment shown in FIG. 2, an organic light emitting diode 200 includes a hole auxiliary layer 140 as well as an emission layer 230. The hole auxiliary layer 140 may increase hole injection and/or hole mobility between the anode 120 and the emission layer 230, and my block electrons. The hole auxiliary layer 140 may be, for example, a hole transport layer (HTL), a hole injection layer (HIL), and/or an electron blocking layer, and may include at least one layer. The compound according to an embodiment may be included in the emission layer 230 and/or the hole auxiliary layer 140. As an organic thin layer 105, an electron injection layer (EIL), an electron transport layer (ETL), an auxiliary electron transport layer (ETL), an auxiliary hole transport layer (HTL), hole transport layer (HTL), a hole injection layer (HIL), or a combination thereof may be further included, although they are not shown in FIG. 1 or 2.

In FIGS. 1 and 2, at least one selected from the emission layer 130 and 230, the hole transport layer (HTL) 140, the electron injection layer (EIL), the electron transport layer (ETL), the auxiliary electron transport layer (ETL), the auxiliary hole transport layer (HTL), the hole injection layer (HIL), and a combination thereof, may include the compound the organic thin layer 105.

For example, the compound may be used in the hole injection layer (HIL) or the hole transport layer (HTL).

The compound for an organic optoelectric device according to an embodiment may be used in the emission layer, and may be used as a host in an emission layer. For example, it may be used as a green phosphorescent host in an emission layer.

The organic light emitting diodes 100 and 200 may be manufactured by, e.g.,: forming an anode or a cathode on a substrate; forming an organic thin layer in accordance with a dry coating method (such as evaporation, sputtering, plasma plating, and ion plating) or a wet coating method (such as spin coating, dipping, and flow coating); and providing a cathode or an anode thereon.

In another example embodiment, a display device including the organic optoelectric device is provided.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

(Preparation of Compound for Organic Optoelectric Device)

Synthesis of Compound for Organic Optoelectric Device

[General Formula 1]

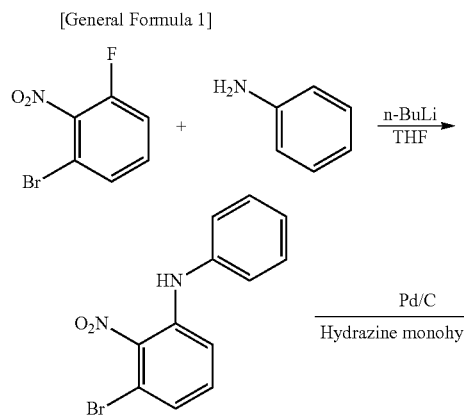

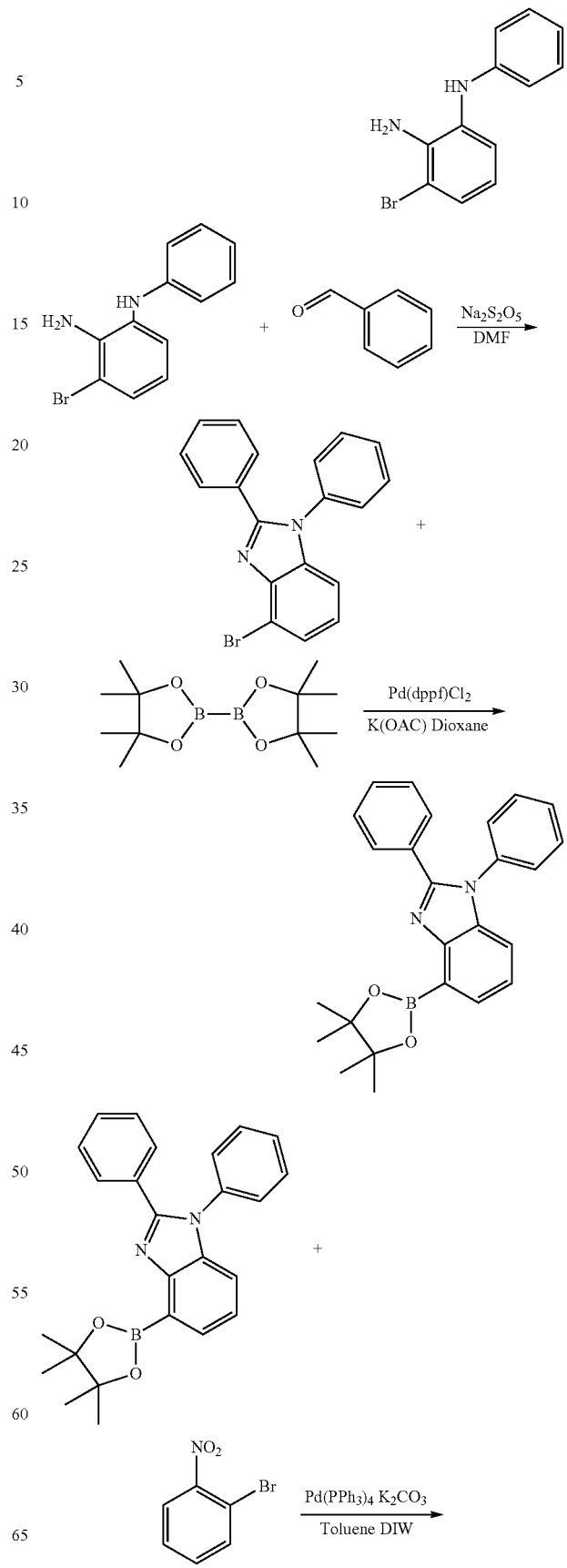

77
-continued
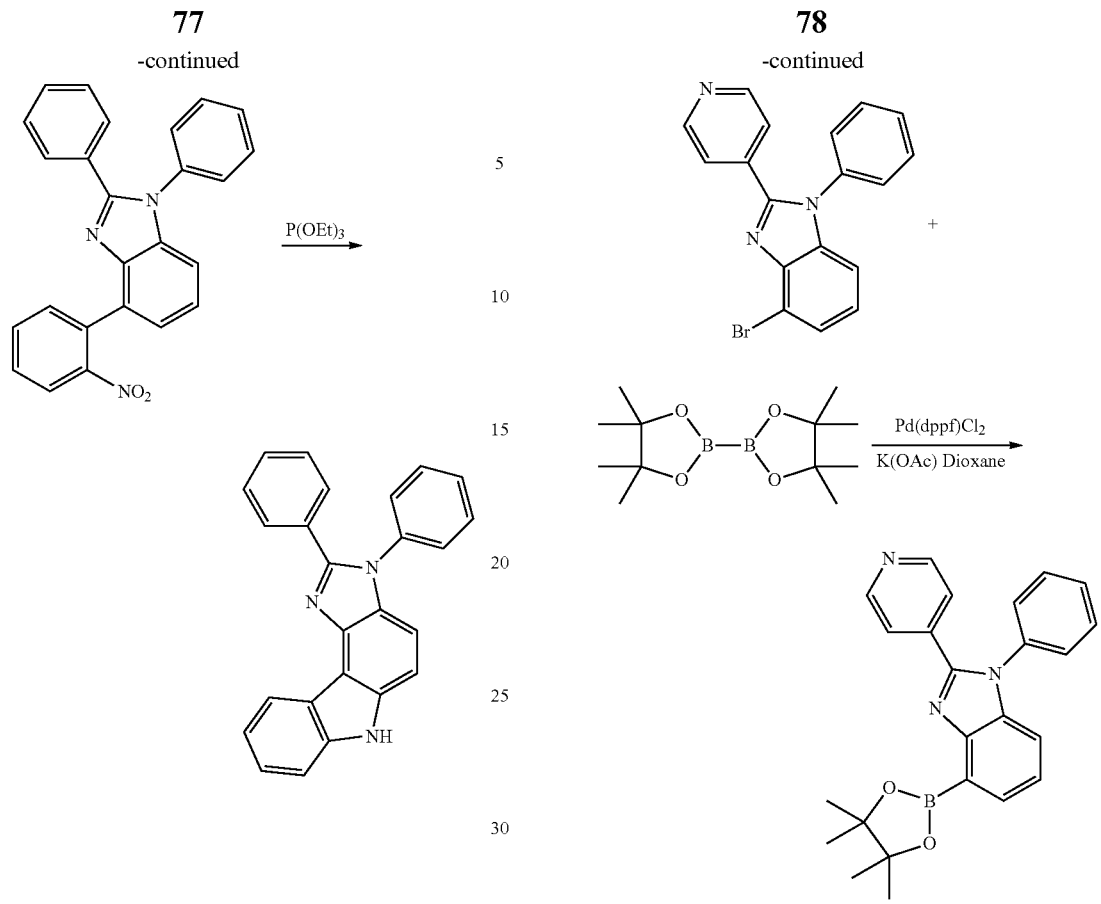
[General Formula 2]
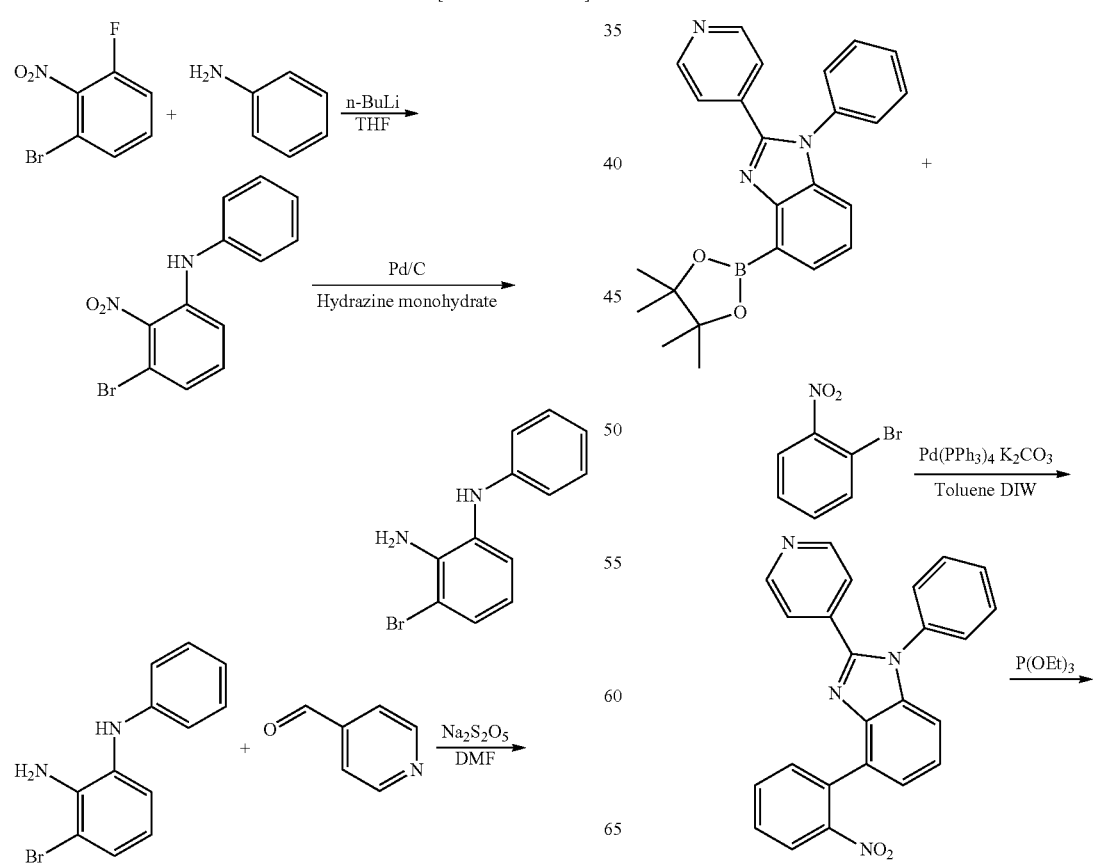
78
-continued

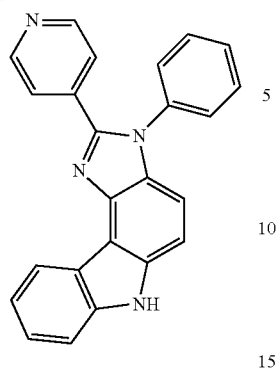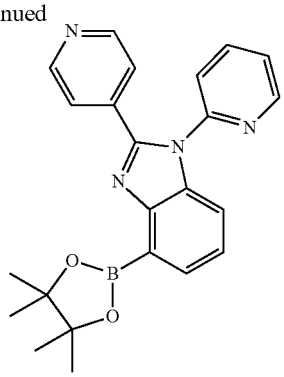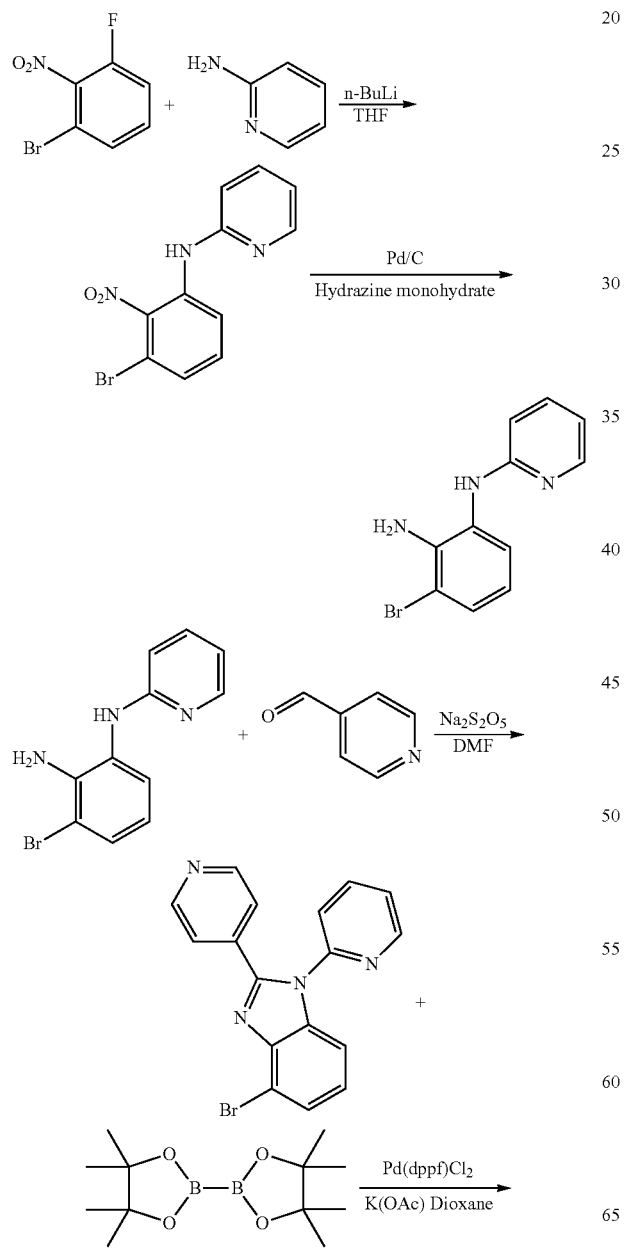
[General Formula 3]
The compounds prepared in the above synthesis method according to example embodiments are described in the following Table 1.

TABLE 1
| Compound | Reaction intermediate 1 | Reaction intermediate 2 | Yield (%) | MS data |
|---|---|---|---|---|
| 3-1 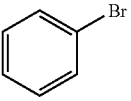 | 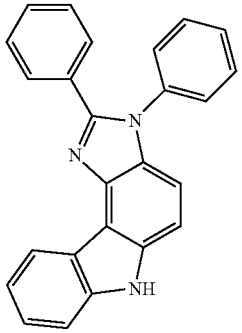 [SMILES: c1ccc(-c2nc3c4c(ccc3n2-c2ccccc2)[nH]c2ccccc24)cc1] | 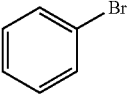 | 89 | 435.52 g/mol |
| 3-13 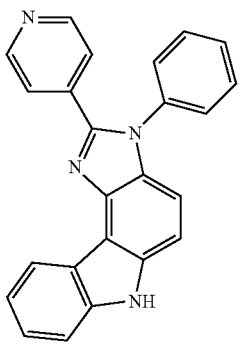 [SMILES: c1ccc(-n2c(-c3ccncc3)nc3c4c(ccc32)[nH]c2ccccc24)cc1] | 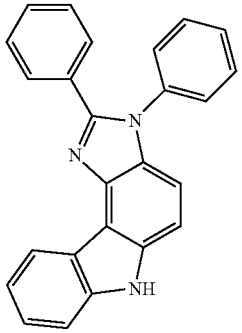 [SMILES: c1ccc(-c2nc3c4c(ccc3n2-c2ccccc2)[nH]c2ccccc24)cc1] | 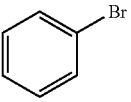 | 91 | 436.51 g/mol |
| 3-37 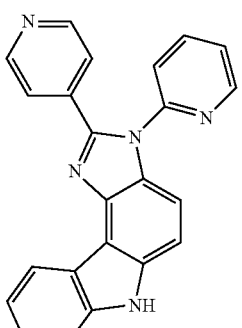 | 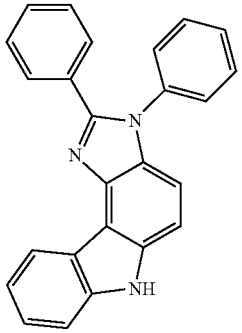 [SMILES: c1ccc(-c2nc3c4c(ccc3n2-c2ccccc2)[nH]c2ccccc24)cc1] | 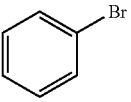 | 93 | 437.49 g/mol |

TABLE 1-continued
| Compound | Reaction intermediate 1 | Reaction intermediate 2 | Yield (%) | MS data |
|---|---|---|---|---|
| 3-49 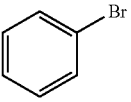 | 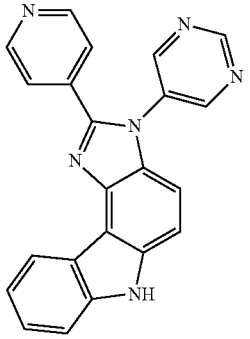 [SMILES: c1ccc2c(c1)[nH]c1ccc3c(nc(-c4ccncc4)n3-c3cncnc3)c12] | 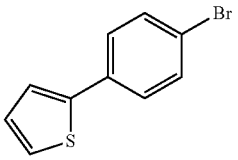 [SMILES: Brc1ccc(-c2cccs2)cc1] | 89 | 438.48 g/mol |
| 3-93 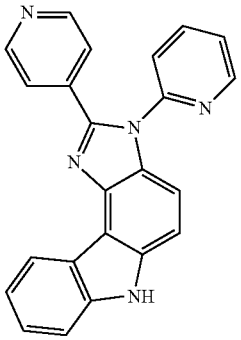 [SMILES: c1ccc(-n2c(-c3ccncc3)nc3c4c(ccc32)[nH]c2ccccc24)nc1] | 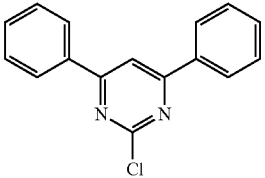 [SMILES: Clc1nc(-c2ccccc2)cc(-c2ccccc2)n1] | 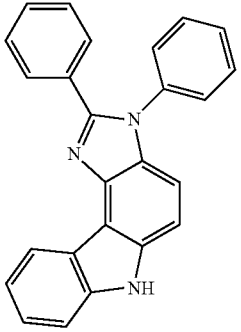 [SMILES: c1ccc(-c2nc3c4c(ccc3n2-c2ccccc2)[nH]c2ccccc24)cc1] | 85 | 519.62 g/mol |
| 3-137 | | | 90 | 589.69 g/mol |

TABLE 1-continued
| Compound | Reaction intermediate 1 | Reaction intermediate 2 | Yield (%) | MS data |
|---|---|---|---|---|
| 3-139 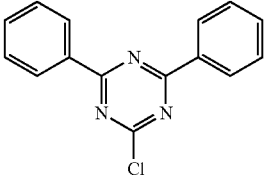 | 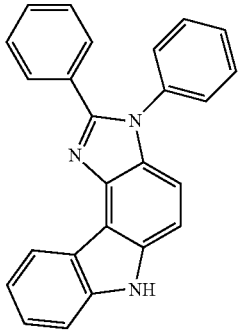 [SMILES: c1ccc(-c2nc3c4c(ccc3n2-c2ccccc2)[nH]c2ccccc24)cc1] | 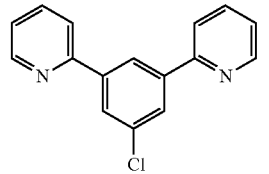 [SMILES: Clc1cc(-c2ccccn2)cc(-c2ccccn2)c1] | 92 | 590.67 g/mol |
| 3-141 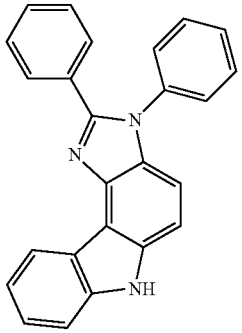 [SMILES: c1ccc(-c2nc3c4c(ccc3n2-c2ccccc2)[nH]c2ccccc24)cc1] | 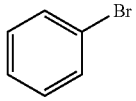 | 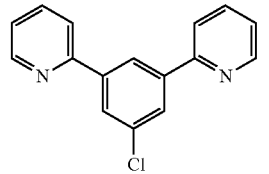 [SMILES: Clc1cc(-c2ccccn2)cc(-c2ccccn2)c1] | 87 | 589.69 g/mol |
| 5-1 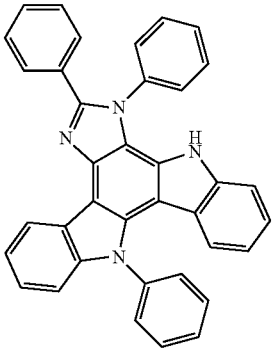 [SMILES: c1ccc(-c2nc3c4c5ccccc5n(-c5ccccc5)c4c4c5ccccc5[nH]c4c3n2-c2ccccc2)cc1] | Br–Ph | | 89 | 600.71 g/mol |

TABLE 1-continued
| Compound | Reaction intermediate 1 | Reaction intermediate 2 | Yield (%) | MS data |
|---|---|---|---|---|
| 5-52 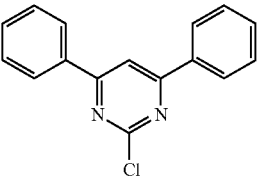 [SMILES: Clc1nc(-c2ccccc2)cc(-c2ccccc2)n1] | 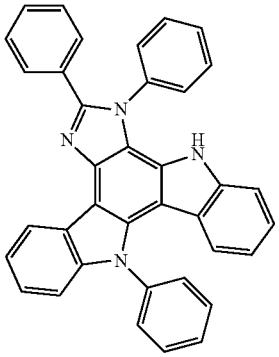 [SMILES: c1ccc(-c2nc3c4c5ccccc5n(-c5ccccc5)c4c4c5ccccc5[nH]c4c3n2-c2ccccc2)cc1] | 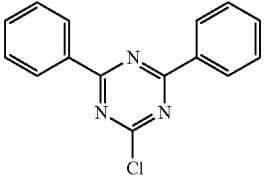 [SMILES: Clc1nc(-c2ccccc2)nc(-c2ccccc2)n1] | 85 | 754.88 g/mol |
| 5-56 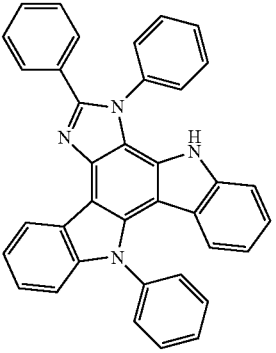 [SMILES: c1ccc(-c2nc3c4c5ccccc5n(-c5ccccc5)c4c4c5ccccc5[nH]c4c3n2-c2ccccc2)cc1] | 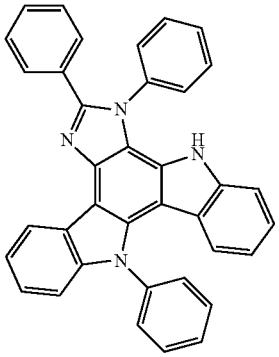 [SMILES: c1ccc(-c2nc3c4c5ccccc5n(-c5ccccc5)c4c4c5ccccc5[nH]c4c3n2-c2ccccc2)cc1] | 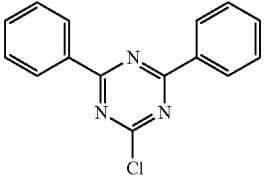 [SMILES: Clc1nc(-c2ccccc2)nc(-c2ccccc2)n1] | 87 | 755.87 g/mol |
Synthesis Example 1
Synthesis of Compound 3-1
[Reaction Scheme 1]
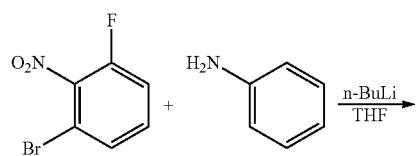
-continued
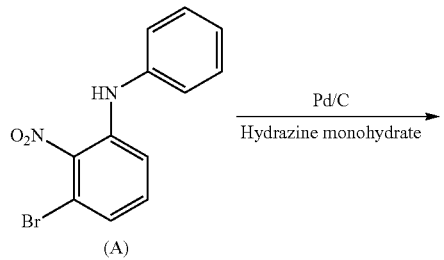
(A)

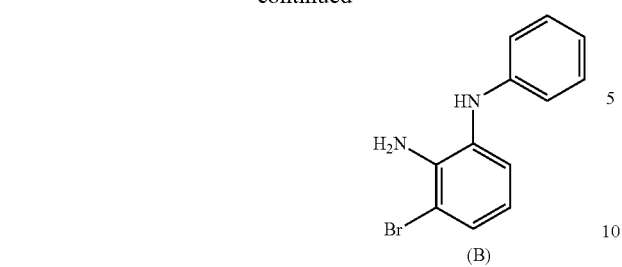
(B)
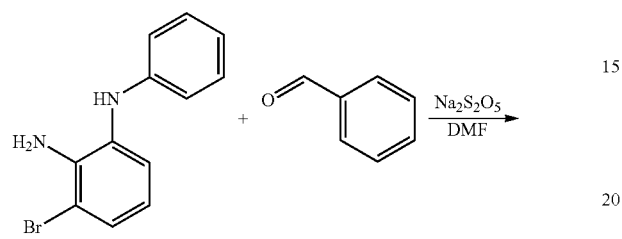
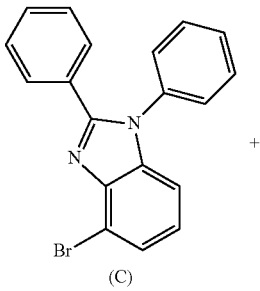
(C)
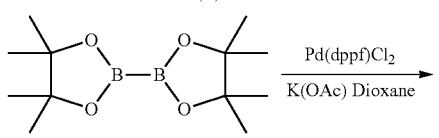
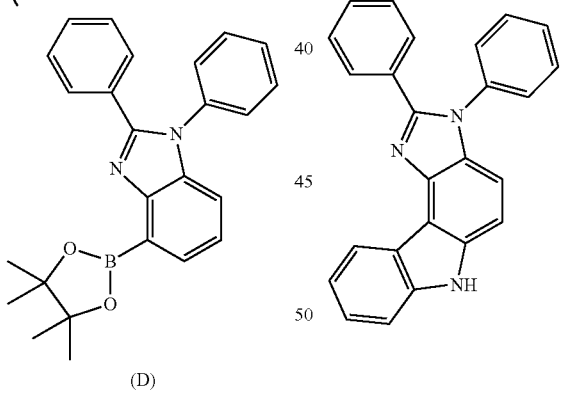
(D)
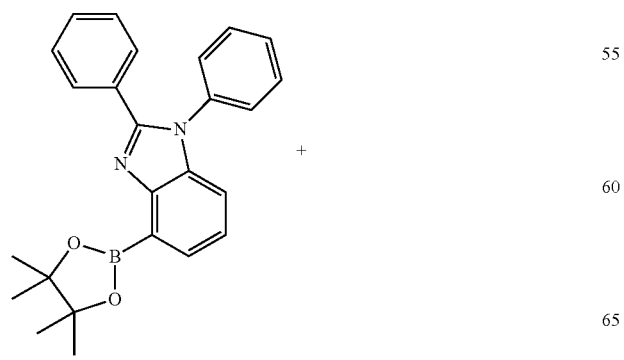
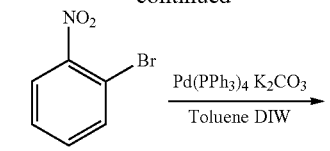
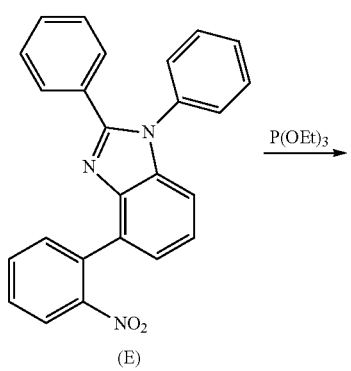
(E)
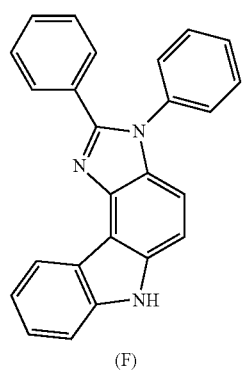
(F)
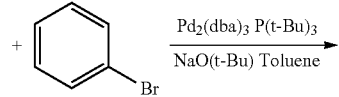
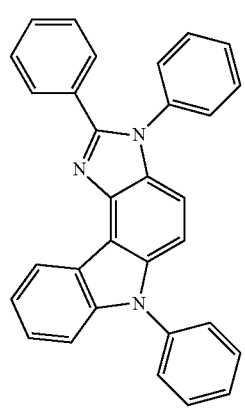 [SMILES: c1ccc(-c2nc3c4c5ccccc5n(-c5ccccc5)c4ccc3n2-c2ccccc2)cc1]

First Step: Synthesis of Intermediate Product (A)

10.0 g (107.38 mmol) of aniline was dissolved in 400 mL of THF, and 55.84 mL (139.59 mmol) of n-BuLi was slowly added thereto at −78° C. After agitating the mixture at −78° C. for 1 hour, 25.99 g (118.11 mmol) of 2-bromo-6-fluoro nitro benzene was slowly added thereto, and the resulting mixture was agitated under a nitrogen stream for 24 hours at room temperature The resultant was extracted with dichloromethane and distilled water, and an organic layer produced therein was filtered with silica gel. The organic solution was removed therefrom, and a silica gel column chromatography was performed with a mixture of hexane:dichloromethane=7:3(v/v), obtaining 15.5 g of an intermediate product A (yield: 49%).

Second Step; Synthesis of Intermediate Product (B)

15.5 g (52.88 mmol) of the intermediate product A and 0.31 g (2 wt %) of Pd/C were suspended in a mixture of 200 mL of THF and 300 mL of ethanol, and 25.65 mL (528.79 mmol) of hydrazine monohydrate was slowly added thereto at 0° C. The mixture was agitated under a nitrogen stream for 24 hours at room temperature. The reaction material was filtered with a silica gel filter, and an organic solution was removed therefrom, obtaining 13.5 g of an intermediate product (B) (yield: 97%).

Third Step; Synthesis of Intermediate Product (C)

15.0 g (68.59 mmol) of the intermediate product (B) and 7.28 g (68.59 mmol) of benzaldehyde were suspended in 200 mL of DMF, 15.65 g (82.31 mmol) of $Na_2S_2O_5$ was slowly added thereto room temperature, and the mixture was slowly agitated under a nitrogen stream for 8 hours. The resultant was extracted with dichloromethane and distilled water, and an organic layer produced therein was filtered with silica gel. After removing an organic solution therefrom, silica gel column chromatography was performed by using a mixture of hexane:dichloromethane=7:3 (v/v), obtaining 15.81 g of an intermediate product (B) (yield: 66%).

Fourth Step: Synthesis of Intermediate Product (D)

11.0 g (31.50 mmol) of the intermediate product (C), 10.40 g (40.95 mmol) of bis(pinacolato)diboron, 9.27 g (94.50 mmol) of K(OAc), and 0.51 g (0.63 mmol) of Pd(dppf)$Cl_2$ were suspended in 150 mL of toluene, and the suspended solution was refluxed and agitated under a nitrogen stream for 24 hours. The reactant was extracted with dichloromethane and distilled water, and an organic layer produced therein was filtered with silica gel. After removing an organic solution therefrom, a silica gel column chromatography was performed by using a mixture of hexane:dichloromethane=6:4 (v/v), obtaining 10.3 g of an intermediate product (D) (yield: 83%).

Fifth Step: Synthesis of Intermediate Product (E)

10.3 g (25.99 mmol) of the intermediate product (D), 5.78 g (28.59 mmol) of 2-bromonitrobenzene, 5.39 g (38.99 mmol) of $K_2CO_3$, and 0.30 g (0.26 mmol) of Pd(PPh$_3$)$_4$ were suspended in a mixture of 100 ml of toluene and 50 ml of distilled water, and the suspended solution was refluxed and agitated under a nitrogen stream for 12 hours. When reaction was complete, the reaction solution was extracted with dichloromethane and filtered with silica gel and then, distilled under a reduced pressure and silica gel column chromatography was performed with a mixture of hexane:ethyl acetate=9:1 (v/v), obtaining 7.5 g of an intermediate product (E) (yield: 74%).

Sixth step: Synthesis of Intermediate Product (F)

7.5 g (19.16 mmol) of the intermediate product (E) and 16.67 mL (95.81 mmol) of triethyl phosphite were refluxed and agitated under a nitrogen stream for 4 hours. When the reaction was complete, a reaction solvent was removed from the reactant, and the remnant was subjected to silica gel column chromatography with hexane:dichloromethane=6:4 (v/v), obtaining 5.1 g of an intermediate product (F) (yield: 74%).

Seventh Step: Synthesis of Compound of Chemical Formula 3-1

14.0 g (38.95 mmol) of the intermediate product (F), 7.34 g (46.74 mmol) of bromobenzene, 4.49 g (46.74 mmol) of NaO(t-Bu), and 0.36 g (0.39 mmol) of Pd$_2$(dba)$_3$ were suspended in 150 mL of toluene, 0.19 mL (0.78 mmol) of P(t-Bu)$_3$ was added thereto, and the mixture was refluxed and agitated under a nitrogen stream for 24 hours. The resultant was extracted with dichloromethane and distilled water, and an organic layer produced therein was filtered with silica gel. After removing an organic solution therefrom, a silica gel column chromatography was performed with hexane:dichloromethane=7:3 (v/v) and recrystallization was performed with dichloromethane and acetone, obtaining 15.1 g of a compound 3-1 (yield: 89%).

Synthesis Example 2

Synthesis of Compound 3-13

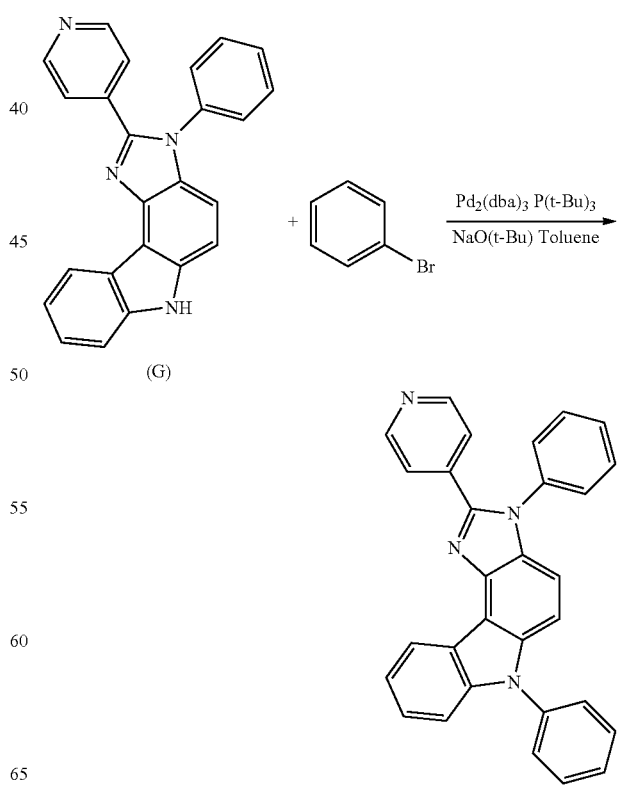

15.0 g (41.62 mmol) of the intermediate product (G) prepared according to the same method as Synthesis Example 1 except for using pyridine-4-carboaldehyde instead of the benzaldehyde in the third step of Synthesis Example 1, 7.84 g (49.94 mmol) of bromobenzene, 4.80 g (49.94 mmol) of NaO(t-Bu), 0.38 g (0.42 mmol) of Pd$_2$(dba)$_3$ were suspended in 120 mL of toluene, and 0.20 mL (0.83 mmol) of P(t-Bu)$_3$ was added thereto, and the mixture was refluxed and agitated under a nitrogen stream for 24 hours. The resultant was extracted with dichloromethane and distilled water, and an organic layer was filtered with silica gel. After removing an organic solution therefrom, a silica gel column chromatography was performed with hexane:dichloromethane=7:3 (v/v) and recrystallization was performed with dichloromethane and acetone, obtaining 16.5 g of a compound 3-13 (yield: 91%).

Synthesis Example 3

Synthesis of Compound 3-37

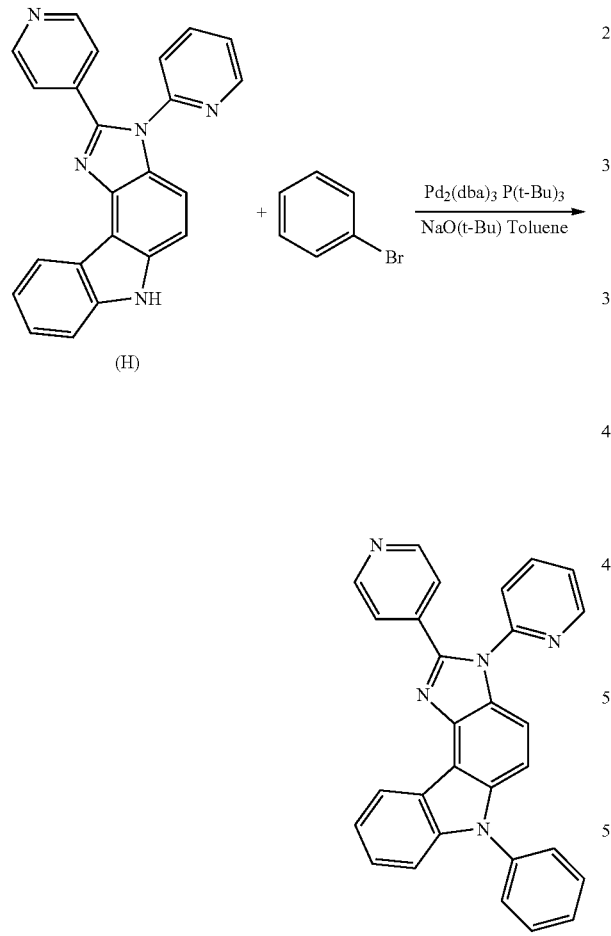

(H)

10.0 g (27.67 mmol) of an intermediate product (H) synthesized according to the same method as Synthesis Example 2 except for using pyridinyl-2-amine instead of the aniline in the first step of Synthesis Example 1, 5.21 g (33.20 mmol) of bromobenzene, 3.19 g (33.20 mmol) of NaO(t-Bu), and 0.25 g (0.28 mmol) of Pd$_2$(dba)$_3$ were suspended in 100 mL of toluene, 0.13 mL (0.55 mmol) of P(t-Bu)$_3$ was added thereto, and the mixture was refluxed and agitated under a nitrogen stream for 24 hours. The resultant was extracted with dichloromethane and distilled water, and an organic layer produced therein was filtered with silica gel. After removing an organic solution therefrom, silica gel column chromatography was performed with hexane:dichloromethane=7:3 (v/v) and recrystallization was performed with dichloromethane and acetone, obtaining 11.3 g of a compound 3-37 (yield: 93%).

Synthesis Example 4

Synthesis of Compound 3-49

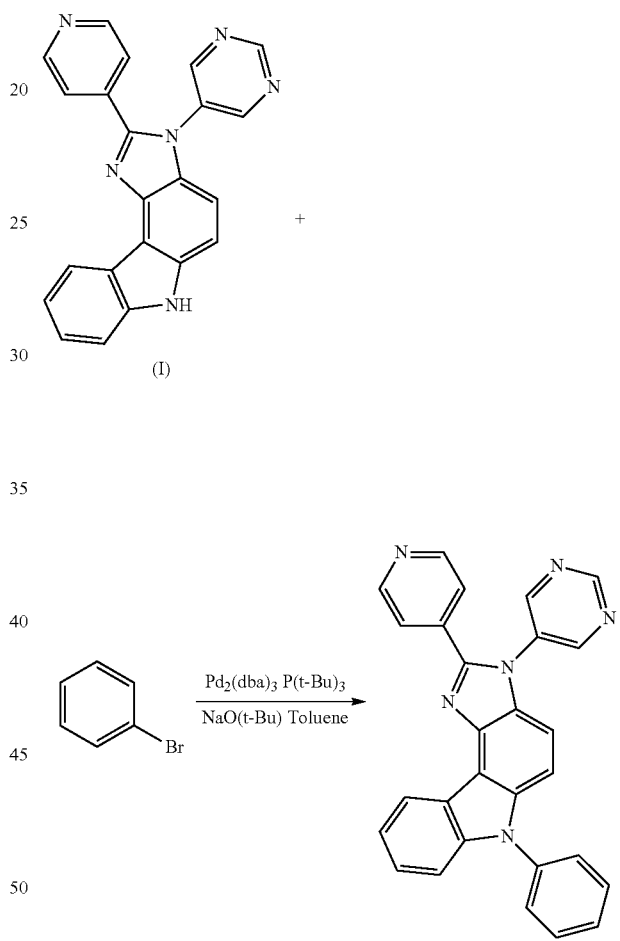

10.0 g (27.59 mmol) of an intermediate product (I) prepared according to the same method as Synthesis Example 1 except for using pyrimidinyl-5-amine instead of the aniline in the first step of Synthesis Example 2, 5.20 g (33.11 mmol) of bromobenzene, 3.18 g (33.11 mmol) of NaO(t-Bu), and 0.25 g (0.28 mmol) of Pd$_2$(dba)$_3$ were suspended in 100 mL of toluene, 0.13 mL (0.55 mmol) of P(t-Bu)$_3$ was added thereto, and the mixture was refluxed and agitated under a nitrogen stream for 24 hours. The resultant was extracted with dichloromethane and distilled water, and an organic layer produced therein was filtered with silica gel. After removing an organic solution therefrom, a silica gel column chromatography was performed with hexane:dichloromethane=7:3 (v/v) and recrystallization was performed with dichloromethane and acetone, obtaining 10.8 g of a compound 3-49 (yield: 89%).

Synthesis Example 5

Synthesis of Compound 3-93

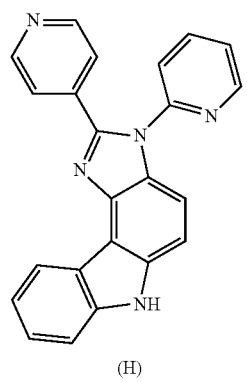
(H)

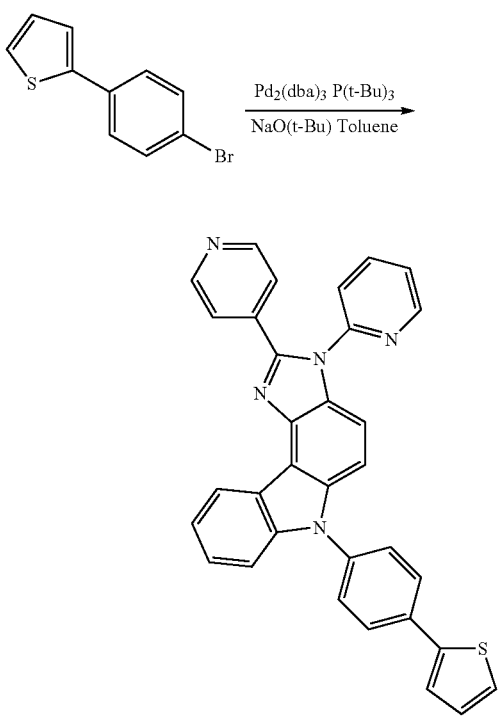

romethane=7:3 (v/v) and recrystallization was performed with dichloromethane and acetone, obtaining 12.2 g of a compound 3-93 (yield: 85%).

Synthesis Example 6

Synthesis of Compound 3-137

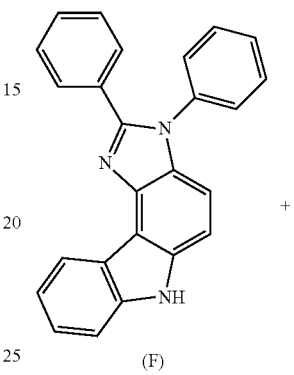
(F)

10.0 g (27.67 mmol) of the intermediate product (H) according to Synthesis Example 3, 7.94 g (33.20 mmol) of 2-(4-bromophenyl)-thiophene, 3.19 g (33.20 mmol) of NaO(t-Bu), and 0.25 g (0.28 mmol) of Pd$_2$(dba)$_3$ were suspended in 100 mL of toluene, 0.13 mL (0.55 mmol) of P(t-Bu)$_3$ was added thereto, and the mixture was refluxed and agitated under a nitrogen stream for 24 hours. The resultant was extracted with dichloromethane and distilled water, and an organic layer produced therein was filtered with silica gel. After removing an organic solution therefrom, a silica gel column chromatography was performed with hexane:dichlo- 10.0 g (27.82 mmol) of the intermediate product (F) according to Synthesis Example 1 and 8.16 g (30.60 mmol) of 2-chloro-4,6-diphenylpyrimidine were suspended in 100 mL of DMF, 0.80 g (33.39 mmol) of NaH was added thereto at 0° C., and the mixture was agitated under a nitrogen stream at room temperature for 6 hours. The resultant was extracted with dichloromethane and distilled water, and an organic layer produced therein was filtered with silica gel. After removing an organic solution therefrom, a silica gel column chromatography was performed with hexane:dichloromethane=6:4 (v/v) and recrystallization was performed with dichloromethane and ethyl acetate, obtaining 14.7 g of a compound 3-137 (yield: 90%).

Synthesis Example 7

Synthesis of Compound 3-139

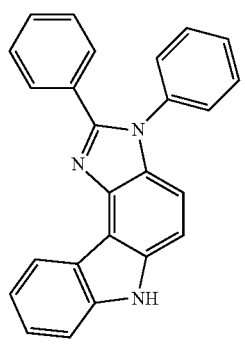
(F)

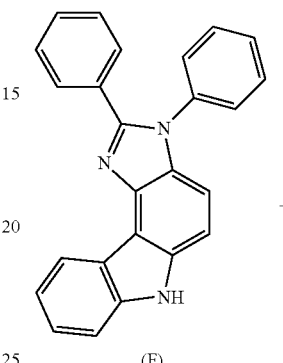

10.0 g (27.82 mmol) of the intermediate product (F) according to Synthesis Example 1 and 8.19 g (30.60 mmol) of 2-chloro-4,6-diphenyltriazine were suspended in 100 mL of DMF, 0.80 g (33.39 mmol) of NaH was added thereto at 0° C., and the mixture was agitated under a nitrogen stream at room temperature for 6 hours. The resultant was extracted with dichloromethane and distilled water, and an organic layer produced therein was filtered with silica gel. After removing an organic solution therefrom, a silica gel column chromatography was performed with hexane:dichloromethane=6:4 (v/v) and recrystallization was performed with dichloromethane and ethyl acetate, obtaining 15.1 g of a compound 3-139 (yield: 92%).

Synthesis Example 8

Synthesis of Compound 3-141

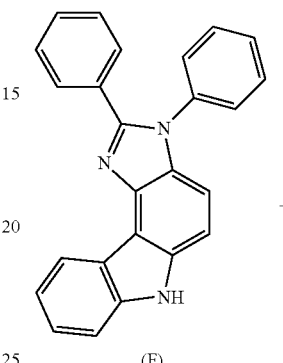
(F)

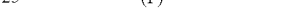

10.0 g (27.82 mmol) of an intermediate product (F) prepared in the same method as Synthesis Example 1 and 8.16 g (30.60 mmol) of 5-chloro-1,3-(2,2'-dipyridyl)benzene was suspended in 100 mL of DMF, 0.80 g (33.39 mmol) of NaH was added thereto at 0° C., and the mixture was agitated under a nitrogen stream at room temperature for 6 hours. The resultant was extracted with dichloromethane and distilled water, and an organic layer produced therein was filtered with silica gel. After removing an organic solution therefrom, a silica gel column chromatography was performed with hexane:dichloromethane=6:4 (v/v) and then, recrystallization was performed with dichloromethane and ethyl acetate, obtaining 14.3 g of a compound 3-141 (yield: 87%).

[Reaction Scheme 2]
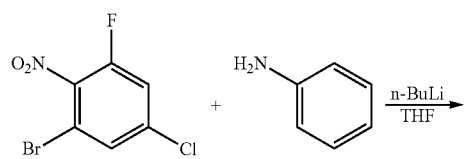
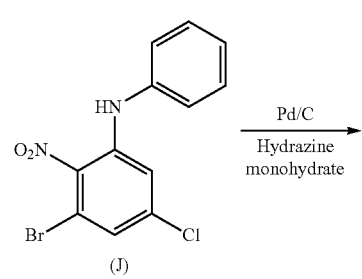
(J)
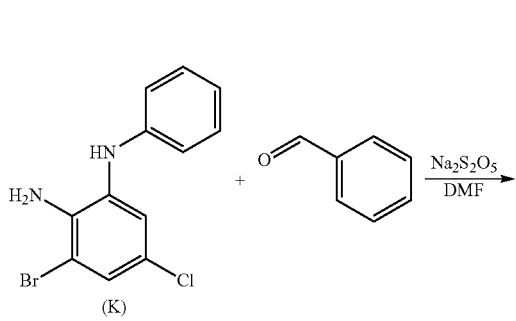
(K)
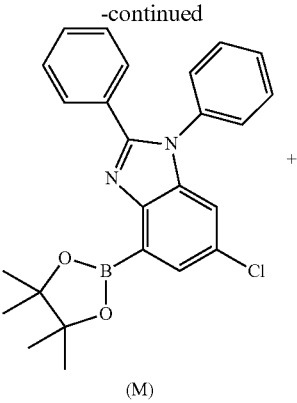
(M)
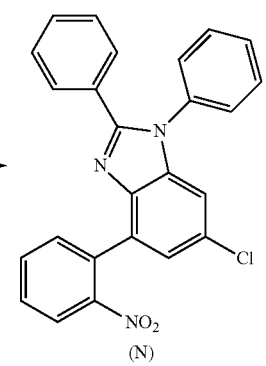
(N)
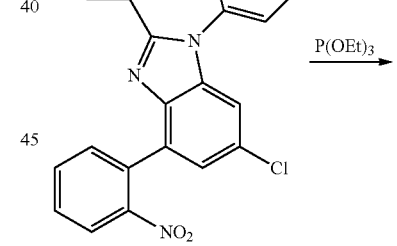
(L)
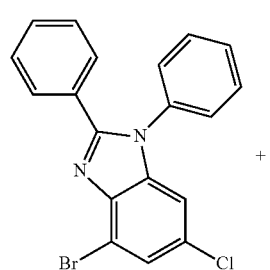
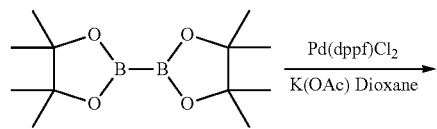
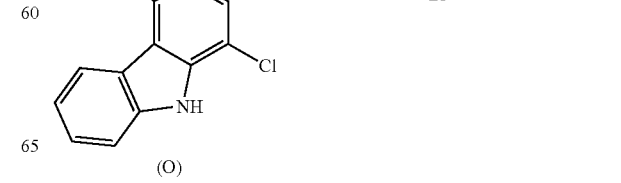
(O)

-continued

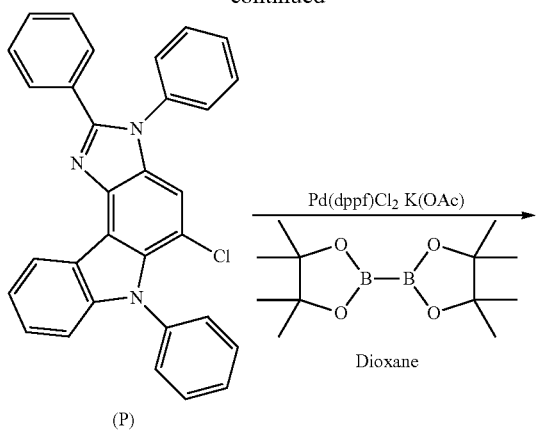

(P)

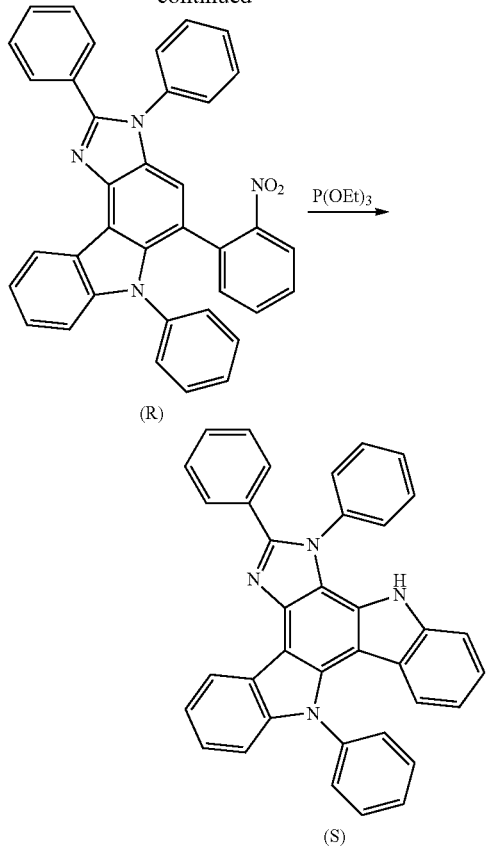

(R)

(S)

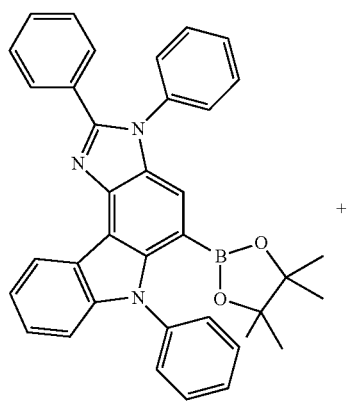

(Q)

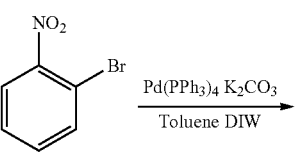

First Step; Synthesis of Intermediate Product (J)

10.0 g (107.38 mmol) of aniline was dissolved in 400 mL of THF, and 55.84 mL (139.59 mmol) of n-BuLi was slowly added thereto at −78° C. The mixture was agitated at −78° C. for 1 hour, 30.05 g (118.11 mmol) of 2-bromo-4-chloro-6-fluoro nitro benzene was slowly added thereto, and the mixture was agitated under a nitrogen stream for 24 hours at room temperature. The resultant was extracted with dichloromethane and distilled water, and an organic layer produced therein was filtered with silica gel. After removing an organic solution therefrom, a silica gel column chromatography was performed with hexane:dichloromethane=7:3 (v/v), obtaining 15.1 g of an intermediate product (J) (yield: 43%).

Second Step; Synthesis of Intermediate Product (K)

15.0 g (45.79 mmol) of the intermediate product (J) and 0.30 g (2 wt %) of Pd/C were suspended in 200 mL of THF and 300 mL of ethanol, and 22.21 mL (457.93 mmol) of hydrazine monohydrate was slowly added thereto at 0° C. The mixture was agitated under a nitrogen stream for 24 hours at room temperature. The reaction material was filtered with silica gel, and an organic solution was removed therefrom, obtaining 12.8 g of an intermediate product (K) (yield: 94%).

Third Step; Synthesis of Intermediate Product (L)

12.0 g (40.33 mmol) of the intermediate product (K) and 7.28 g (48.39 mmol) of benzaldehyde were suspended in 160 mL of DMF, and 13.44 g (56.46 mmol) of $Na_2S_2O_5$ was slowly added thereto at room temperature, and the mixture was agitated under a nitrogen stream for 8 hours. The resultant was extracted with dichloromethane and distilled water, and an organic layer was filtered with silica gel. After removing an organic solution therefrom, a silica gel column chromatography was performed with hexane:dichloromethane=7:3 (v/v), obtaining 10.6 g of an intermediate product (L) (yield: 68%).

Fourth Step: Synthesis of Intermediate Product (M)

10.0 g (26.06 mmol) of the intermediate product (L), 7.28 g (28.67 mmol) of bis(pinacolato)diboron, 7.67 g (78.19 mmol) of K(OAc), and 0.43 g (0.52 mmol) of Pd(dppf)Cl$_2$ were suspended in 100 mL of toluene, and the suspended solution was refluxed and agitated under a nitrogen stream for 24 hours. The resultant was extracted with dichloromethane and distilled water, and an organic layer was filtered with silica gel. After removing an organic solution therefrom, a silica gel column chromatography was performed with hexane:dichloromethane=6:4 (v/v), obtaining 9.0 g of an intermediate product (M) (yield: 80%).

Fifth Step: Synthesis of Intermediate Product (N)

12.0 g (27.86 mmol) of the intermediate product (M), 0.19 g (30.65 mmol) of 2-bromonitrobenzene 6, 5.78 g (41.79 mmol) of K$_2$CO$_3$, and 0.32 g (0.28 mmol) of Pd(PPh$_3$)$_4$ were suspended in 100 ml of toluene and 50 ml of distilled water, and the suspended solution was refluxed and agitated under a nitrogen stream for 12 hours. When the reaction was complete, the reaction solution was extracted with dichloromethane and filtered with silica gel and then, distilled under a reduced pressure, and a silica gel column chromatography was performed with hexane:ethyl acetate=9:1 (v/v), obtaining 8.4 g of an intermediate product (N) (yield: 71%).

Sixth Step: Synthesis of Intermediate Product (O)

10.0 g (23.48 mmol) of the intermediate product (N) and 20.43 mL (117.41 mmol) of triethyl phosphate were refluxed and agitated under a nitrogen stream for 4 hours. When the reaction was complete, a reaction solvent was removed therefrom, and a silica gel column chromatography was performed with hexane:dichloromethane=6:4 (v/v), obtaining 6.5 g of an intermediate product (O) (yield: 70%).

Seventh Step: Synthesis of Intermediate Product (P)

10.0 g (25.39 mmol) of the intermediate product (O), 4.01 mL (38.08 mmol) of bromobenzene, 3.66 g (38.08 mmol) of NaO(t-Bu), and 0.93 g (1.02 mmol) of Pd$_2$(dba)$_3$ were suspended in 100 mL of toluene, 0.48 mL (2.03 mmol) of P(t-Bu)$_3$ was added thereto, and the mixture was refluxed and agitated under a nitrogen stream for 24 hours. The resultant was extracted with dichloromethane and distilled water, and an organic layer produced therein was filtered with silica gel. After removing an organic solution therefrom, a silica gel column chromatography was performed with hexane:dichloromethane=7:3 (v/v) and recrystallization was performed with dichloromethane and acetone, obtaining 10.6 g of an intermediate product (P) (yield: 89%).

Eighth Step: Synthesis of Intermediate Product (O)

10.0 g (21.28 mmol) of the intermediate product (P), 7.02 g (27.66 mmol) of bis(pinacolato)diboron, 6.26 g (63.84 mmol) of K(OAc), and 0.35 g (0.43 mmol) of Pd(dppf) Cl$_2$ were suspended in 100 mL of toluene, and the suspended solution was refluxed and agitated under a nitrogen stream for 24 hours. The resultant was extracted with dichloromethane and distilled water, and an organic layer was filtered with silica gel. After removing an organic solution therefrom, silica gel column chromatography was performed with hexane:dichloromethane=6:4 (v/v), obtaining 9.0 g of an intermediate product (O) (yield: 75%).

Ninth Step: Synthesis of Intermediate Product (R)

10.0 g (17.81 mmol) of the intermediate product (O), 3.96 g (19.59 mmol) of 2-bromonitrobenzene, 3.69 g (26.72 mmol) of K$_2$CO$_3$, and 0.21 g (0.18 mmol) of Pd(PPh$_3$)$_4$ were suspended in 80 ml of toluene and 40 ml of distilled water, and the suspended solution was refluxed and agitated under a nitrogen stream for 12 hours. When the reaction was complete, the reaction solution was extracted with dichloromethane and filtered with silica gel and then, distilled under a reduced pressure and silica gel column chromatography was performed with hexane:ethyl acetate=9:1 (v/v), obtaining 7.9 g of an intermediate product (R) (yield: 85%).

Tenth Step: Synthesis of Intermediate product (S)

10.0 g (17.97 mmol) of the intermediate product (R) and 15.63 mL (89.83 mmol) of triethyl phosphite were refluxed and agitated under a nitrogen stream for 4 hours. When the reaction was complete, a reaction solvent was removed therefrom, and a silica gel column chromatography was performed with hexane:dichloromethane=6:4 (v/v), obtaining 6.1 g of an intermediate product (S) (yield: 65%).

Synthesis Example 9

Synthesis of Compound 5-1

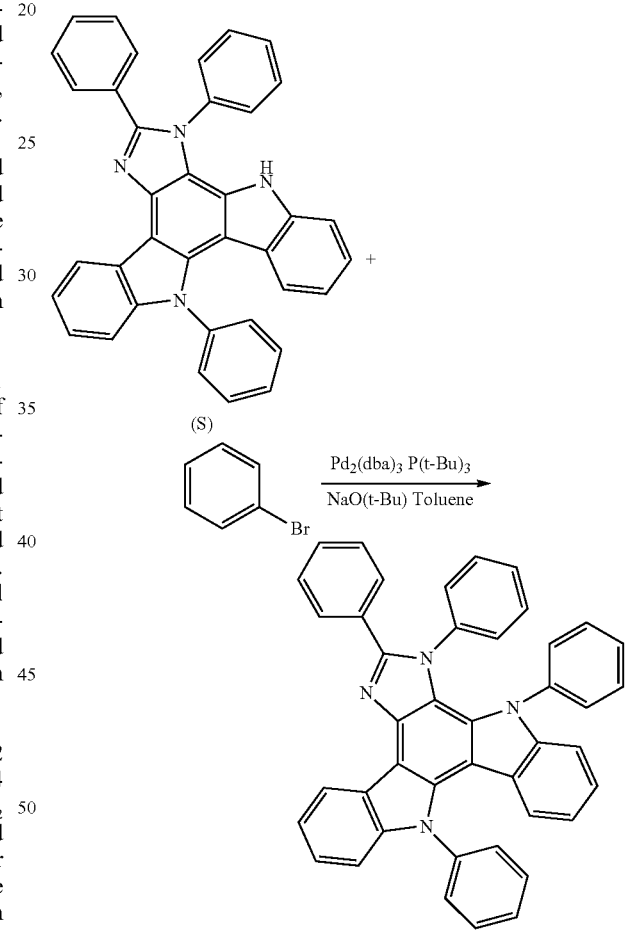

15.0 g (28.59 mmol) of the intermediate product (S) prepared according to Reaction Scheme 2, 4.52 mL (42.89 mmol) of bromobenzene, 5.50 g (57.19 mmol) of NaO(t-Bu), and 0.79 g (0.86 mmol) of Pd$_2$(dba)$_3$ were suspended in 140 mL of toluene, 0.42 mL (1.72 mmol) of P(t-Bu)$_3$ was added thereto, and the mixture was refluxed and agitated under a nitrogen stream for 24 hours. The resultant was extracted with dichloromethane and distilled water, and an organic layer was filtered with silica gel. After removing an organic solution therefrom, silica gel column chromatography was performed with hexane:dichloromethane=7:3 (v/v) and recrystallization was performed with dichloromethane and acetone, obtaining 15.3 g of a compound 5-1 (yield: 89%).

Synthesis Example 10

Synthesis of Compound 5-52

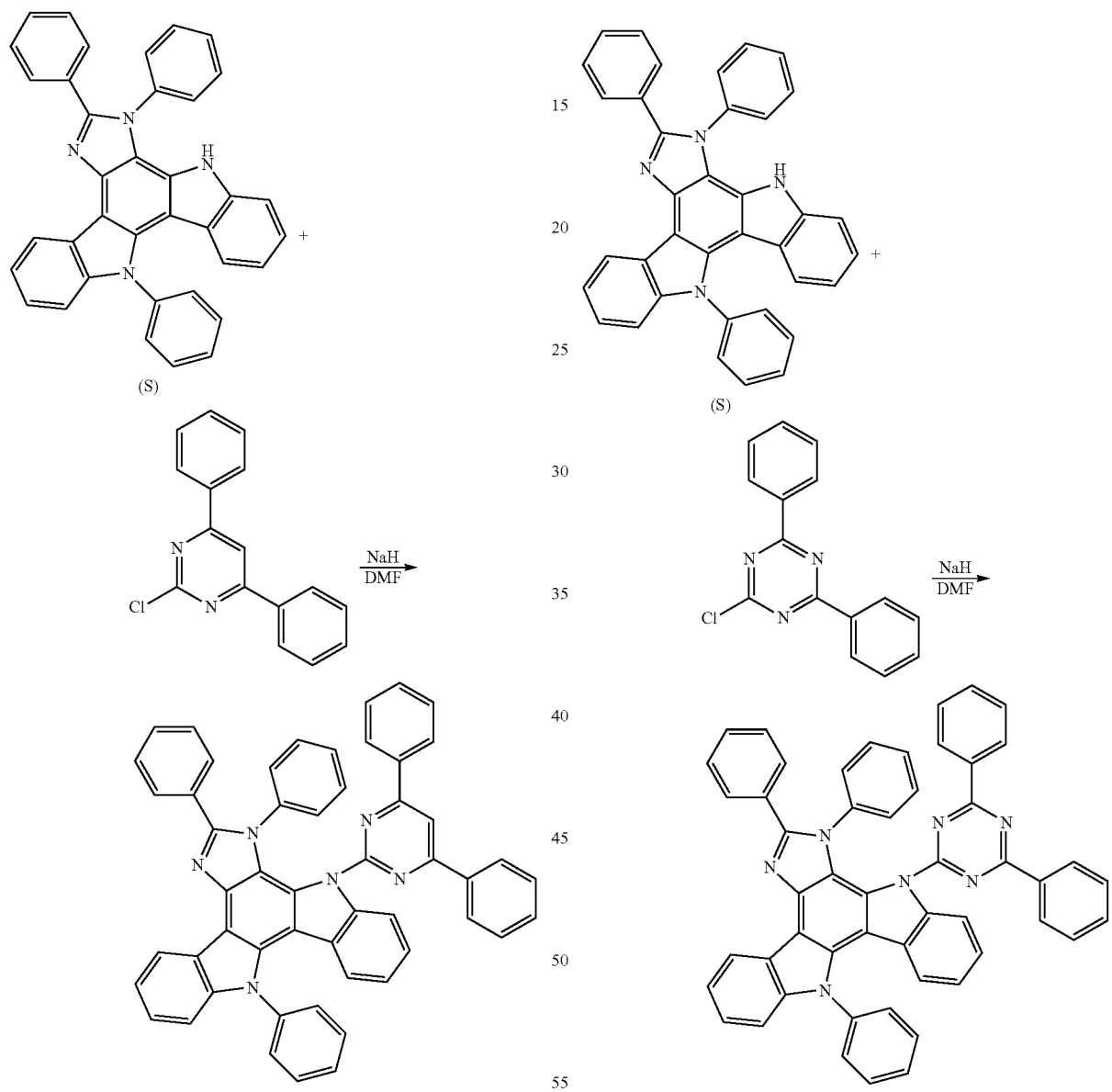

Synthesis Example 11

Synthesis of Compound 5-56

10.0 g (19.06 mmol) of the intermediate product (S) according to Reaction Scheme 2 and 5.59 g (20.97 mmol) of 2-chloro-4.6-diphenylpyrimidine were suspended in 100 mL of DMF, 0.55 g (22.87 mmol) of NaH was added thereto at 0° C., and the mixture was agitated under a nitrogen stream at room temperature for 6 hours. The reactant was extracted with dichloromethane and distilled water, and an organic layer produced therein was filtered with silica gel. After removing an organic solution, silica gel column chromatography was performed with hexane:dichloromethane=6:4 (v/v) and recrystallization was performed with dichloromethane and ethyl acetate, obtaining 12.2 g of a compound 5-52 (yield: 85%).

10.0 g (19.06 mmol) of the intermediate product (S) according to Reaction Scheme 2 and 5.61 g (20.97 mmol) of 2-chloro-4.6-diphenylpyrimidine were suspended in 100 mL of DMF, 0.55 g (22.87 mmol) of NaH was added thereto at 0° C., and the mixture was agitated under a nitrogen stream at room temperature for 6 hours. The resultant was extracted with dichloromethane and distilled water, and an organic layer was filtered with silica gel. After removing an organic solution therefrom, silica gel column chromatography was performed with hexane:dichloromethane=6:4 (v/v) and recrystallization was performed with dichloromethane and ethyl acetate, obtaining 12.5 g of a compound 5-56 (yield: 87%).

Manufacture of Organic Light Emitting Diode

Example 1

ITO (indium tin oxide) was coated to be 1500 Å thick on a glass substrate, and the coated glass was ultrasonic wave-washed with a distilled water. After washing with distilled water, the washed glass substrate was ultrasonic wave-washed with a solvent such as isopropyl alcohol, acetone, methanol, and the like was moved to a plasma cleaner to clean the substrate by using oxygen plasma for 5 minutes and moved to a vacuum depositor. This ITO transparent electrode was used as an anode, HTM (refer to the following formula regarding the structure of the material) was vacuum-deposited to form a 1200 Å-thick hole injection layer (HIL) on the ITO substrate.

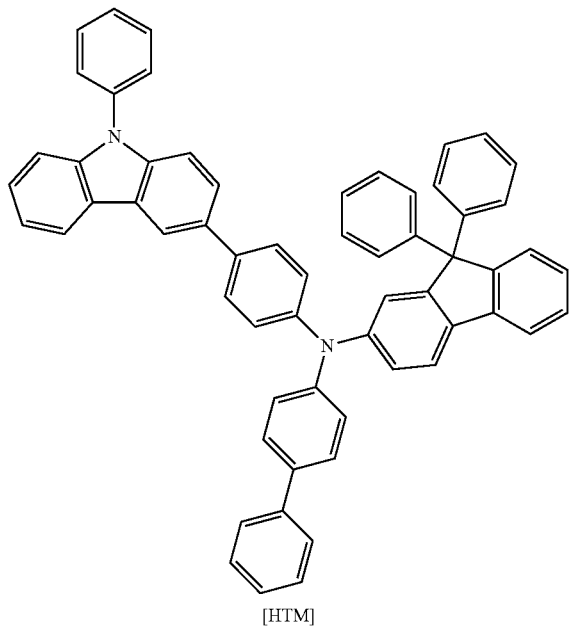

[HTM]

On the hole transport layer (HTL), a 300 Å-thick emission layer was formed by vacuum-depositing the doped compound of Synthesis Example 1 as a host doped with 7 wt % of PhGD as a green phosphorescent dopant (refer to the following formula).

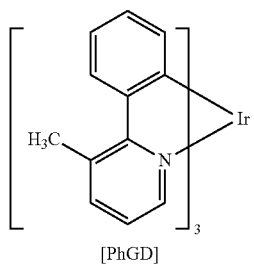

[PhGD]

On the emission layer upper, a 50 Å-thick BAlq [bis(2-methyl-8-quinolinolato-N1,O8)-(1,1'-biphenyl-4-olato)aluminum] and a 250 Å-thick Alq3 [tris(8-hydroxyquinolinato)aluminum] were sequentially stacked to form an electron transport layer (ETL). On the electron transport layer (ETL), 5 Å-thick LiF and 1000 Å-thick Al were sequentially vacuum-deposition to form a cathode, manufacturing an organic light emitting diode.

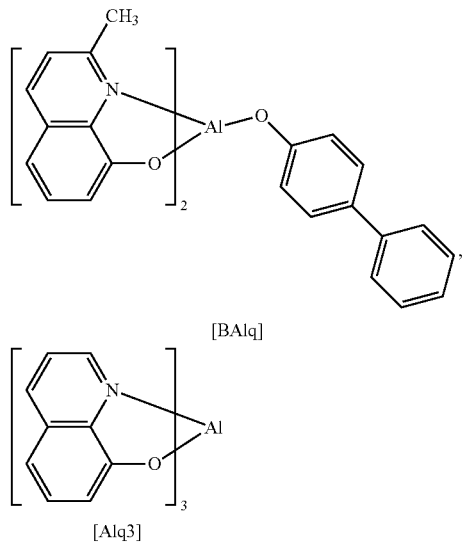

Example 2

An organic light emitting diode was manufactured according to the same method as Example 1 except for using the compound 3-13 according to Synthesis Example 2 to form an emission layer.

Example 3

An organic light emitting diode was manufactured according to the same method as Example 1 except for using the compound 3-37 according to Synthesis Example 3 to form an emission layer.

Example 4

An organic light emitting diode was manufactured according to the same method as Example 1 except for using the compound 3-49 according to Synthesis Example 4 to form an emission layer.

Example 5

An organic light emitting diode was manufactured according to the same method as Example 1 except for using the compound 3-93 according to Synthesis Example 5 to form an emission layer.

Example 6

An organic light emitting diode was manufactured according to the same method as Example 1 except for using the compound 3-137 according to Synthesis Example 6 to form an emission layer.

Example 7

An organic light emitting diode was manufactured according to the same method as Example 1 except for using the compound 3-139 according to Synthesis Example 7 to form an emission layer.

Example 8

An organic light emitting diode was manufactured according to the same method as Example 1 except for using the compound 3-141 according to Synthesis Example 8 to form an emission layer.

Example 9

An organic light emitting diode was manufactured according to the same method as Example 1 except for using the compound 5-1 according to Synthesis Example 9 to form an emission layer.

Example 10

An organic light emitting diode was manufactured according to the same method as Example 1 except for using the compound 5-52 according to Synthesis Example 10 to form an emission layer.

Example 11

An organic light emitting diode was manufactured according to the same method as Example 1 except for using the compound 5-56 according to Synthesis Example 11 to form an emission layer.

Comparative Example 1

An organic light emitting diode was manufactured according to the same method as Example 1 except for using the following to form an emission layer:

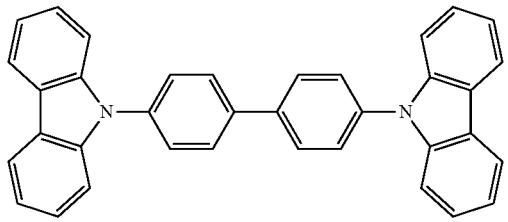 [SMILES: c1ccc2c(c1)c1ccccc1n2-c1ccc(-c2ccc(-n3c4ccccc4c4ccccc43)cc2)cc1]

(Performance Measurement of Organic Light Emitting Diode)

Current density and luminance changes depending on a voltage and luminous efficiency of each organic light emitting diode according to Examples 1 to 11 and Comparative Example 1 were measured. The measurements were specifically performed in the following method, and the results are provided in the following Table 2.

1) Measurement of Current density Change depending on Voltage Change

The organic light emitting diodes manufactured according to Examples 1 to 11 and Comparative Example 1 were measured for current value flowing in the unit device, while increasing the voltage using a current-voltage meter (Keithley 2400), and the measured current value was divided by an area to provide the results.

2) Measurement of Luminance Change depending on Voltage Change

The organic light emitting diodes according to Examples 1 to 11 and Comparative Example 1 were measured for luminance, while increasing the voltage using a luminance meter (Minolta Cs-1000A).

3) Measurement of Luminous Efficiency

Current efficiency (cd/A) and power efficiency (lm/W) at the same current density (10 mA/cm$^2$) were calculated by using the luminance, current density, and voltages (V) from the items 1) Current density Change depending on Voltage Change and 2) Luminance Change depending on Voltage Change.

TABLE 2

| | Luminance 500 cd/m$^2$ | | | | |
|---|---|---|---|---|---|
| | Driving voltage (V) | Luminous efficiency (cd/A) | Power Efficiency (lm/W) | CIE x | y |
| Example 1 | 4.81 | 52.23 | 34.10 | 0.341 | 0.612 |
| Example 2 | 4.32 | 53.43 | 38.84 | 0.349 | 0.622 |
| Example 3 | 4.21 | 53.98 | 40.26 | 0.347 | 0.619 |
| Example 4 | 4.07 | 54.01 | 41.67 | 0.340 | 0.630 |
| Example 5 | 3.94 | 55.47 | 44.21 | 0.336 | 0.628 |
| Example 6 | 3.67 | 57.88 | 49.52 | 0.339 | 0.631 |
| Example 7 | 3.58 | 59.27 | 51.98 | 0.340 | 0.623 |
| Example 8 | 3.79 | 56.35 | 46.69 | 0.337 | 0.620 |
| Example 9 | 4.75 | 53.14 | 35.13 | 0.351 | 0.619 |
| Example 10 | 3.50 | 56.39 | 50.59 | 0.331 | 0.631 |
| Example 11 | 3.59 | 58.42 | 51.10 | 0.329 | 0.629 |
| Comparative Example 1 | 6.90 | 49.53 | 22.54 | 0.333 | 0.623 |

As shown in Table 2, the organic light emitting diodes according to Examples 1 to 11 showed improved characteristics in terms of driving voltage, luminous efficiency, and/or power efficiency compared with the organic light emitting diodes according to Comparative Example 1.

By way of summation and review, an organic light emitting diode (OLED) has recently drawn attention due to an increase in demand for flat panel displays. The organic light emitting diode converts electrical energy into light by applying current to an organic light emitting material, and has a structure in which an organic layer is interposed between an anode and a cathode. The organic layer may include an emission layer. The organic layer may also include, e.g., an auxiliary layer, and the auxiliary layer may include at least one layer selected from, for example, a hole injection layer, a hole transport layer, an electron blocking layer, an electron transport layer, an electron injection layer, and a hole blocking layer. Such a structure may improve efficiency and stability of an organic light emitting diode.

Performance of an organic light emitting diode may be affected by characteristics of the organic layer, and among them, may be significantly affected by characteristics of an organic material of the organic layer. An organic material that increases hole and electron mobility, and simultaneously increases electrochemical stability, may be useful for an organic light emitting diode applied to a large-size flat panel display.

As described above, embodiments may provide a compound for an organic optoelectric device. Embodiments may provide an organic optoelectric device having characteristics such as high efficiency, long life-span, and the like. An organic optoelectric device including the compound for an organic optoelectric device according to an embodiment may have excellent electrochemical and thermal stability and improved life-span characteristics, and high luminous efficiency at a low driving voltage. The compound for an organic optoelectric device according to an embodiment may be appropriate for a solution process.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope as set forth in the following claims.

DESCRIPTION OF SYMBOLS

100: organic light emitting diode 200: organic light emitting diode
110: cathode 120: anode
105: organic thin layer 140: hole transport layer (HTL)
130: emission layer 230: emission layer

What is claimed is:

1. A compound, represented by the following Chemical Formula 1, for an organic optoelectric device:

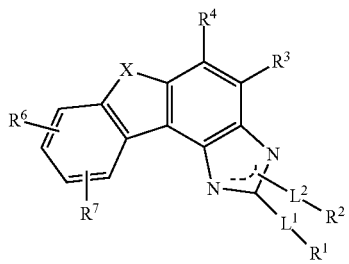

[Chemical Formula 1]

wherein, in the above Chemical Formula 1,
$R^1$ and $R^2$ are each independently a substituted or unsubstituted C6 to C30 aryl group, a substituted or unsubstituted C2 to C30 heteroaryl group, or a combination thereof,
X is O, S, $SO_2$ (O=S=O), PO(P=O), N-$L^3$-$R^5$, CR'R'', or SiR'R'',
$L^1$ to $L^3$ are each independently a single bond, a substituted or unsubstituted C1 to C30 alkylene group, a substituted or unsubstituted C3 to C30 cycloalkylene group, a substituted or unsubstituted C3 to C30 heterocycloalkylene group, a substituted or unsubstituted C6 to C30 arylene group, or a substituted or unsubstituted C2 to C30 heteroarylene group, a substituted or unsubstituted C6 to C30 aryleneamine group, a substituted or unsubstituted C2 to C30 heteroaryleneamine group, a substituted or unsubstituted C1 to C30 alkoxylene group, a substituted or unsubstituted C6 to C30 aryloxylene group, a substituted or unsubstituted C2 to C30 alkenylene group, a substituted or unsubstituted C2 to C30 alkynylene group, or a combination thereof,
$R^3$ to $R^7$, R', and R'' are each independently hydrogen, deuterium, a halogen, a cyano group, a hydroxyl group, an amino group, a substituted or unsubstituted C1 to C20 amine group, a nitro group, a carboxyl group, a ferrocenyl group, a substituted or unsubstituted C1 to C20 alkyl group, a substituted or unsubstituted C6 to C30 aryl group, a substituted or unsubstituted C2 to C30 heteroaryl group, a substituted or unsubstituted C1 to C20 alkoxy group, a substituted or unsubstituted C6 to C20 aryloxy group, a substituted or unsubstituted C3 to C40 silyloxy group, a substituted or unsubstituted C1 to C20 acyl group, a substituted or unsubstituted C2 to C20 alkoxycarbonyl group, a substituted or unsubstituted C2 to C20 acyloxy group, a substituted or unsubstituted C2 to C20 acylamino group, a substituted or unsubstituted C2 to C20 alkoxycarbonylamino group, a substituted or unsubstituted C7 to C20 aryloxycarbonylamino group, a substituted or unsubstituted C1 to C20 sulfamoylamino group, a substituted or unsubstituted C1 to C20 sulfonyl group, a substituted or unsubstituted C1 to C20 alkylthiol group, a substituted or unsubstituted C6 to C20 arylthiol group, a substituted or unsubstituted C1 to C20 heterocyclothiol group, a substituted or unsubstituted C1 to C20 ureide group, a substituted or unsubstituted C3 to C40 silyl group, or a combination thereof,
$R^3$ and $R^4$ are each independently present or are fused to each other to form a ring, and
the dotted line represents a single bond or a double bond.

2. The compound for an organic optoelectric device as claimed in claim 1, wherein the above Chemical Formula 1 is represented by the following Chemical Formula 2 or 3:

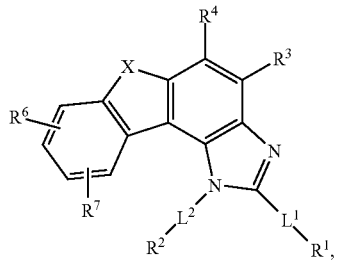

[Chemical Formula 2]

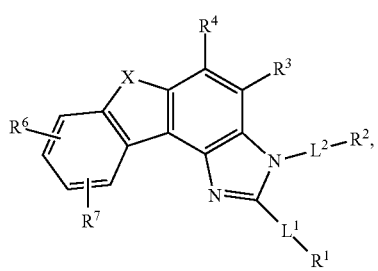

[Chemical Formula 3]

wherein, in the above Chemical Formula 2 or 3,
$R^1$ and $R^2$ are each independently a substituted or unsubstituted C6 to C30 aryl group, a substituted or unsubstituted C2 to C30 heteroaryl group, or a combination thereof,
X is O, S, $SO_2$ (O=S=O), PO(P=O), or N-$L^3$-$R^5$,
$L^1$ to $L^3$ are each independently a single bond, a substituted or unsubstituted C1 to C30 alkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, $R^3$ to $R^7$ are each independently hydrogen, deuterium, a halogen, a cyano group, a hydroxyl group, an amino group, a substituted or unsubstituted C1 to C20 amine group, a substituted or unsubstituted C1 to C20 alkyl group, a substituted or unsubstituted C6 to C30 aryl group, a substituted or unsubstituted C2 to C30 heteroaryl group, a substituted or unsubstituted C3 to C40 silyloxy group, a substituted or unsubstituted C3 to C40 silyl group, or a combination thereof, and $R^3$ and $R^4$ are each independently present or are fused to each other to form a ring.

3. The compound for an organic optoelectric device as claimed in claim 1, wherein, in the above Chemical Formula 1, $R^3$ and $R^4$ are fused to each other to form a ring, and the ring is a substituted or unsubstituted indolyl group, a substituted or unsubstituted phenyl group, a substituted or unsubstituted naphthyl group, a substituted or unsubstituted anthracenyl group, a substituted or unsubstituted phenanthryl group, a substituted or unsubstituted quinolinyl group, or a substituted or unsubstituted triphenylene group.

4. The compound for an organic optoelectric device as claimed in claim 1, wherein, in the above Chemical Formula 1, $R^3$ and $R^4$ are fused to each other, and the above Chemical Formula 1 is represented by the following Chemical Formula 4 or 5:

[Chemical Formula 4]

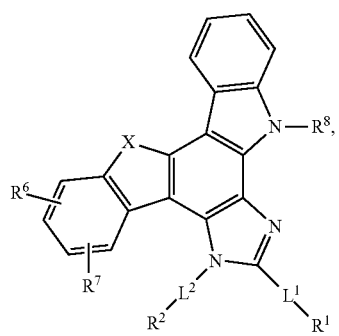

[Chemical Formula 5]

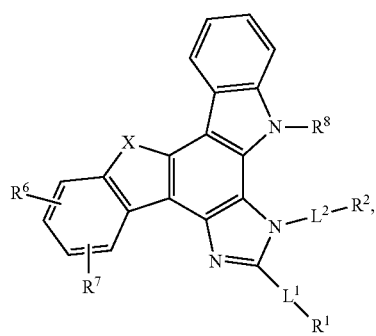

wherein, in the above Chemical Formula 4 or 5, $R^1$, $R^2$, and $R^8$ are each independently a substituted or unsubstituted C6 to C30 aryl group, a substituted or unsubstituted C2 to C30 heteroaryl group, or a combination thereof, X is O, S, $SO_2$ (O=S=O), PO(P=O), or N-$L^3$-$R^5$, $L^1$ to $L^3$ are each independently a single bond, a substituted or unsubstituted C1 to C30 alkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof, and $R^5$ to $R^7$ are each independently hydrogen, deuterium, a halogen, a cyano group, a hydroxyl group, an amino group, a substituted or unsubstituted C1 to C20 amine group, a substituted or unsubstituted C1 to C20 alkyl group, a substituted or unsubstituted C6 to C30 aryl group, a substituted or unsubstituted C2 to C30 heteroaryl group, a substituted or unsubstituted C3 to C40 silyloxy group, a substituted or unsubstituted C3 to C40 silyl group, or a combination thereof.

5. The compound for an organic optoelectric device as claimed in claim 4, wherein the $R^8$ is a substituted or unsubstituted phenyl group, a substituted or unsubstituted biphenyl group, a substituted or unsubstituted pyridyl group, a substituted or unsubstituted pyrimidyl group, or a substituted or unsubstituted triazinyl group.

6. The compound for an organic optoelectric device as claimed in claim 4, wherein the $R^8$ is one of the substituted or unsubstituted functional groups listed in Group I,

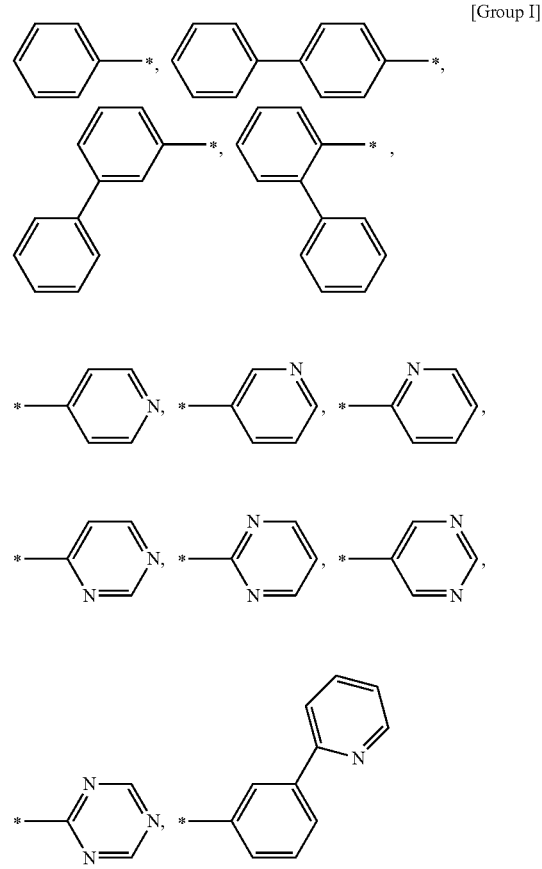

wherein, in the Group 1,

* is a linking point.

7. The compound for an organic optoelectric device as claimed in claim 1, wherein the above Chemical Formula 1 is represented by one of the following Chemical Formulae 6 to 8:

[Chemical Formula 6]

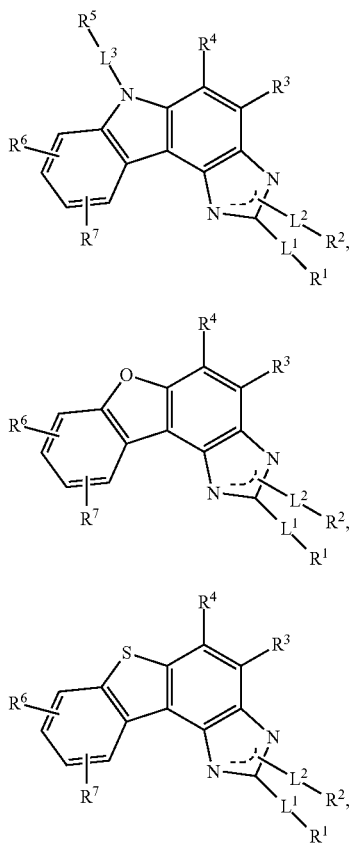

[Chemical Formula 7]

[Chemical Formula 8]

wherein, in the above Chemical Formulae 6 to 8,
R¹ and R² are each independently a substituted or unsubstituted C6 to C30 aryl group, a substituted or unsubstituted C2 to C30 heteroaryl group, or a combination thereof,
L¹ to L³ are each independently a single bond, a substituted or unsubstituted C1 to C30 alkylene group, a substituted or unsubstituted C6 to C30 arylene group, a substituted or unsubstituted C2 to C30 heteroarylene group, a substituted or unsubstituted C2 to C30 alkenylene group, a substituted or unsubstituted C2 to C30 alkynylene group, or a combination thereof,
R³ to R⁷ are each independently hydrogen, deuterium, a halogen, a cyano group, a hydroxyl group, an amino group, a substituted or unsubstituted C1 to C20 amine group, a substituted or unsubstituted C1 to C20 alkyl group, a substituted or unsubstituted C6 to C30 aryl group, a substituted or unsubstituted C2 to C30 heteroaryl group, a substituted or unsubstituted C3 to C40 silyloxy group, a substituted or unsubstituted C3 to C40 silyl group, or a combination thereof,
R³ and R⁴ are each independently present or are fused to each other to form a ring, and
the dotted line represents a single bond or a double bond.

8. The compound for an organic optoelectric device as claimed in claim 7, wherein the R³ to R⁵ are each independently hydrogen, deuterium, or one of the substituted or unsubstituted functional groups listed in the following Group II,
in the above Chemical Formula 6, at least one of R³ to R⁵ is a substituted or unsubstituted functional group listed in the Group II, and in the above Chemical Formulae 7 to 8, at least one of R³ to R⁴ is a substituted or unsubstituted functional group listed in the Group II,

[Group II]

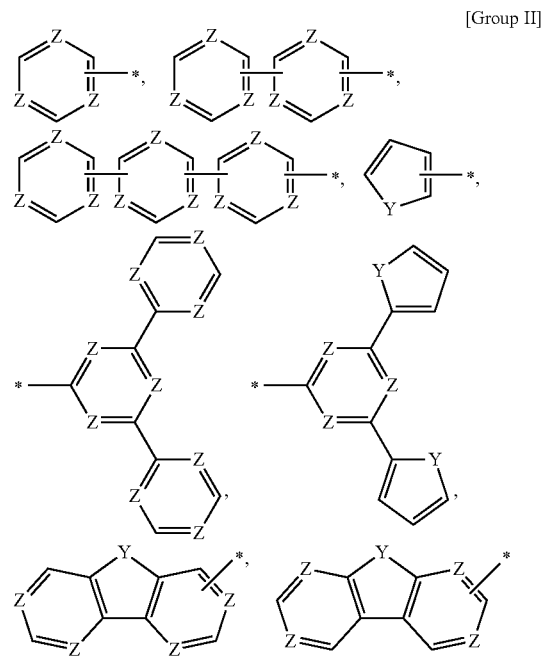

wherein, in the Group II,
each Z is independently N or CR,
each Y is independently O, S, SO, SO₂, NR', CR'R", or SiR'R",
wherein R, R', and R" are each independently hydrogen, deuterium, a substituted or unsubstituted C1 to C30 alkyl group, a substituted or unsubstituted C3 to C30 cycloalkyl group, a substituted or unsubstituted C3 to C30 heterocycloalkyl group, a substituted or unsubstituted C6 to C30 aryl group, a substituted or unsubstituted C2 to C30 heteroaryl group, a substituted or unsubstituted amine group, a substituted or unsubstituted C6 to C30 arylamine group, a substituted or unsubstituted C2 to C30 heteroarylamine group, a substituted or unsubstituted C1 to C30 alkoxy group, a substituted or unsubstituted C2 to C30 alkoxycarbonyl group, a substituted or unsubstituted C2 to C30 alkoxycarbonylamino group, a substituted or unsubstituted C7 to C30 aryloxycarbonylamino group, a substituted or unsubstituted C1 to C30 sulfamoylamino group, a substituted or unsubstituted C2 to C30 alkenyl group, a substituted or unsubstituted C2 to C30 alkynyl group, a substituted or unsubstituted silyl group, a substituted or unsubstituted silyloxy group, a substituted or unsubstituted C1 to C30 acyl group, a substituted or unsubstituted C1 to C20 acyloxy group, a substituted or unsubstituted C1 to C20 acylamino group, a substituted or unsubstituted C1 to C30 sulfonyl group, a substituted or unsubstituted C1 to C30 alkylthiol group, a substituted or unsubstituted C1 to C30 heterocyclothiol group, a substituted or unsubstituted C6 to C30 arylthiol group, a substituted or unsubstituted C1 to C30 heteroarylthiol group, a substituted or unsubstituted C1 to C30 ureide group, a halogen, a halogen-containing group, a cyano group, a hydroxyl group, an amino group, a nitro group, a carboxyl group, a ferrocenyl group, or a combination thereof, and

* is a linking point, and is positioned at one of an element constituting the functional group.

9. The compound for an organic optoelectric device as claimed in claim 7, wherein the $R^3$ to $R^5$ are each independently hydrogen, deuterium, or one of the substituted or unsubstituted functional groups listed in the following Group III, in the above Chemical Formula 6, at least one of $R^3$ to $R^5$ is a substituted or unsubstituted functional group listed in the Group III, and in the above Chemical Formulae 7 to 8, at least one of $R^3$ to $R^4$ is a substituted or unsubstituted functional group listed in the Group III,

[Group III]

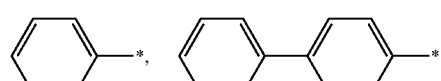
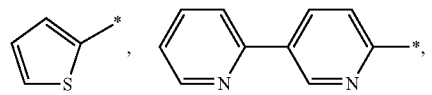
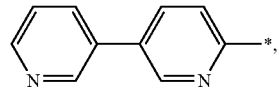
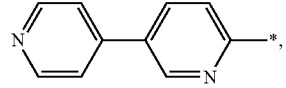
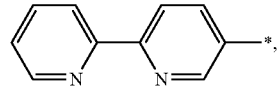
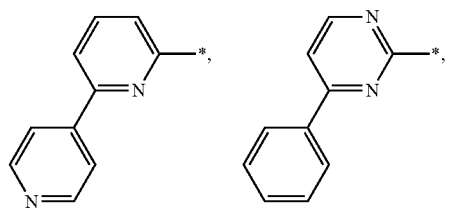
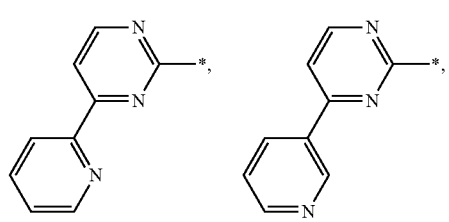
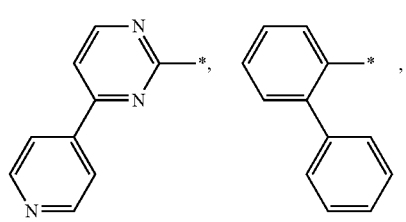
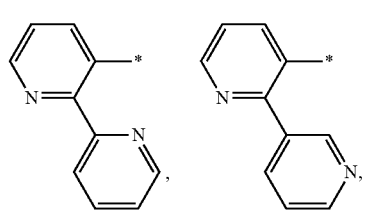
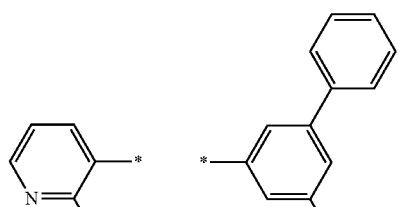
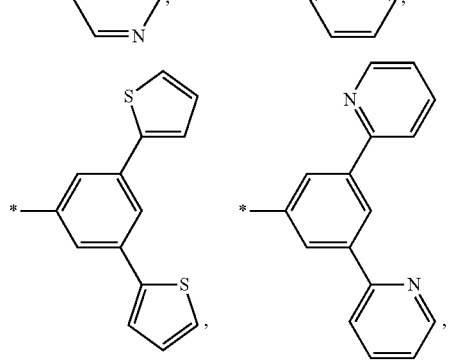

119
-continued

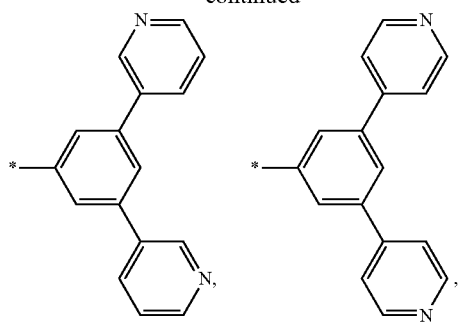

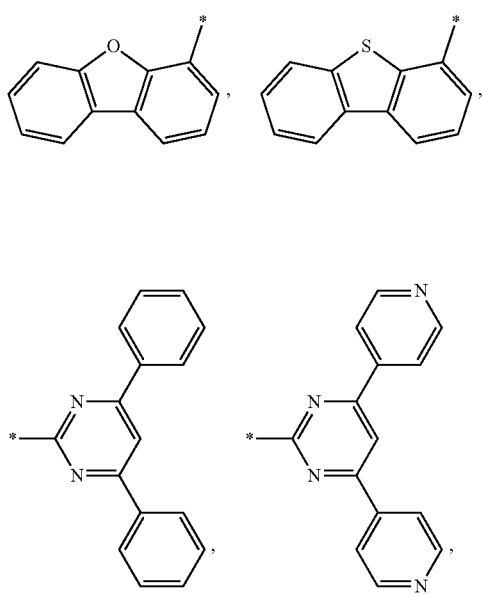

120
-continued

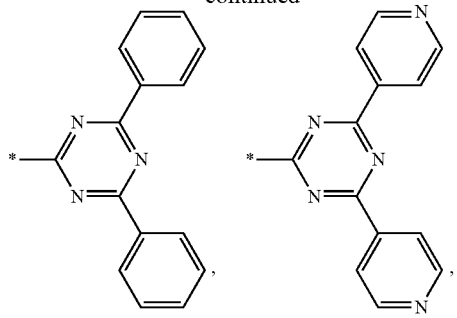

wherein, in the Group III,
* indicates a linking point.

10. An organic optoelectric device, comprising:
an anode and a cathode facing each other, and
at least one organic layer interposed between the anode and the cathode,
wherein the organic layer includes the compound for an organic optoelectric device as claimed in claim 1.

11. The organic optoelectric device as claimed in claim 10, wherein:
the organic layer includes an emission layer, and
the emission layer includes the compound for an organic optoelectric device.

12. The organic optoelectric device as claimed in claim 11, wherein the compound for an organic optoelectric device is included in the emission layer as a host.

13. The organic optoelectric device as claimed in claim 10, wherein:
the organic layer includes at least one auxiliary layer selected from a hole injection layer, a hole transport layer, an electron blocking layer, an electron transport layer, an electron injection layer, and a hole blocking layer, and
the auxiliary layer includes the compound for an organic optoelectric device.

14. A display device comprising the organic optoelectric device as claimed in claim 10.

* * * * *